US009202600B2

(12) United States Patent
Ravn et al.

(10) Patent No.: US 9,202,600 B2
(45) Date of Patent: Dec. 1, 2015

(54) METHOD FOR PRODUCTION OF RADIOISOTOPE PREPARATIONS AND THEIR USE IN LIFE SCIENCE, RESEARCH, MEDICAL APPLICATION AND INDUSTRY

(75) Inventors: Helge Leif Ravn, Vernier (CH); Gerd Juergen Beyer, Challex (FR); Ulli Koester, Geneva (CH); Jacques Lettry, Geneva (CH); Richard Catherall, Geneva (CH); Alexander Hohn, Leibstadt (CH); Joerg Neuhausen, Auenstein (CH); Luca Zanini, Böttstein (CH); Andreas Tuerler, Ismaning (DE)

(73) Assignees: PAUL SCHERRER INSTITUT, Villegen (CH); CERN, Geneva (CH)

( * ) Notice: Subject to any disclaimer, the term of this patent is extended or adjusted under 35 U.S.C. 154(b) by 1572 days.

(21) Appl. No.: 11/814,035

(22) PCT Filed: Jan. 16, 2006

(86) PCT No.: PCT/EP2006/000324
§ 371 (c)(1), (2), (4) Date: Jan. 21, 2009

(87) PCT Pub. No.: WO2006/074960
PCT Pub. Date: Jul. 20, 2006

(65) Prior Publication Data

US 2009/0162278 A1 Jun. 25, 2009

Related U.S. Application Data

(60) Provisional application No. 60/644,182, filed on Jan. 14, 2005.

(51) Int. Cl.

| | |
|---|---|
| ***A61K 51/00*** | (2006.01) |
| ***A61M 36/14*** | (2006.01) |
| ***G21G 1/00*** | (2006.01) |
| ***G21G 1/10*** | (2006.01) |

(52) U.S. Cl.
CPC .................. *G21G 1/001* (2013.01); *G21G 1/10* (2013.01); *G21G 1/00* (2013.01)

(58) Field of Classification Search
CPC ............................... A61K 51/00; A61K 36/14
USPC ........................................................ 424/1.11
See application file for complete search history.

(56) References Cited

U.S. PATENT DOCUMENTS

| | | | | |
|---|---|---|---|---|
| 4,454,233 | A | 6/1984 | Wang et al. | |
| 4,613,553 | A * | 9/1986 | Risen et al. | 430/2 |
| 5,898,178 | A * | 4/1999 | Bunker | 250/423 R |
| 2004/0115207 | A1 | 6/2004 | Irwin et al. | |
| 2005/0232387 | A1* | 10/2005 | Padgett et al. | 376/194 |

OTHER PUBLICATIONS

Snegursky et al. (Nucl. Instr. Methods Phys. Res. B 1997, 26, 301-304).*

Cui et al. (Nucl. Instr. Methods Phys. Res. B 2003, 204, 58-61).*

Beyer, G.J., et al. "Fast Isobaric Separation at the Collector of ISOL-Facilities" *Nuclear Instruments and Methods*, Jul. 1, 1981, pp. 401-407, vol. 186, No. 1-2.

Bricault, P.G., "Review of Radioactive Ion Beam Accelerators" *Proceedings of the 1997 Particle Accelerator Conference*, 1998, pp. 925-929, vol. 1.

Henriksen, G., et al. "Optimisation of Cyclotron Production Parameters for the $^{209}Bi(\alpha, 2n)\,^{211}At$ Reaction Related to Biomedical Use of $^{211}At$" *Applied Radiation and Isotopes*, May 5, 2001, pp. 839-844, vol. 54, No. 5.

Köster, U., "ISOLDE Target and Ion Source Chemistry" *Radiochimica. Acta*, Jan. 10, 2001, pp. 749-756, vol. 89, No. 11-12.

Patel, H.B., et al. "Study of (α, xn) Reactions on $^{169}Tm$, $^{181}Ta$ and $^{209}Bi$ up to 70 MeV" *Il Nuovo Cimento*, Dec. 1999, pp. 1439-1452, vol. 112A, No. 12.

Schmor, P.W. "Initial Commissioning of the ISAC RIB Facility" *Proceedings of the 1999 Particle Accelerator Conference*, 1999, pp. 508-512, vol. 1.

Stracener, D.W., et al. "Targets Used in the Production of Radioactive Ion Beams" *Nuclear Instruments and Methods in Physics Research A*, Mar. 21, 2004, pp. 126-135, vol. 521, No. 1.

Villari, A.C.C. "The Accelerated ISOL Technique and the SPIRAL Project" *Nuclear Physics A*, Oct. 8, 2001, pp. 465-476, vol. A693, No. 1-2.

* cited by examiner

*Primary Examiner* — Michael G Hartley
*Assistant Examiner* — Melissa Perreira
(74) *Attorney, Agent, or Firm* — Saliwanchik, Lloyd & Eisenschenk

(57) ABSTRACT

The present invention relates to an universal method for the large scale production of high-purity carrier free or non carrier added radioisotopes by applying a number of "unit operations" which are derived from physics and material science and hitherto not used for isotope production. A required number of said unit operations is combined, selected and optimized individually for each radioisotope production scheme. The use of said unit operations allows a batch wise operation or a fully automated continuous production scheme. The radioisotopes produced by the inventive method are especially suitable for producing radioisotope-labelled bioconjugates as well as particles, in particular nanoparticles and microparticles.

13 Claims, 18 Drawing Sheets

Batch-wise extraction from liquid targets

16.7% α ← $^{149}$Tb 4.118 h → EC + ß+

| $^{149}$Tb | 4.118 h |
|---|---|
| 165.0 keV | 27.8 % |
| 352.2 keV | 33.0 % |
| 388.3 keV | 20.4 % |
| 651.7 keV | 16.7 % |
| 816.7 keV | 12.3 % |
| 852.8 keV | 16.2 % |

| $^{145}$Eu | 5.93 d |
|---|---|
| 653.5 keV | 15.0 % |
| 893.7 keV | 66.0 % |
| 1658.5 keV | 14.9 % |
| 1972.0 keV | 7.2 % |

| $^{145}$Sm | 340 d |
|---|---|
| 61.3 keV | 12.0 % |

| $^{145}$Pm | 17.7 y |
|---|---|
| 67 + 72 keV | 1.9 + 2.5 % |

| $^{149}$Gd | 9.28 d |
|---|---|
| 149.7 keV | 48.2 % |
| 298.6 keV | 28.6 % |
| 346.7 keV | 23.9 % |
| 748.6 keV | 8.2 % |
| 788.9 keV | 7.3 % |

| $^{149}$Eu | 93.1 d |
|---|---|
| 277.1 keV | 3.6 % |
| 327.5 keV | 4.0 % |

a b

METHOD FOR PRODUCTION OF RADIOISOTOPE PREPARATIONS AND THEIR USE IN LIFE SCIENCE, RESEARCH, MEDICAL APPLICATION AND INDUSTRY

This application is a National Stage Application of International Application Number PCT/EP2006/000324, filed Jan. 16, 2006; which claims the benefit of U.S. Provisional Application No. 60/644,182, filed Jan. 14, 2005, in its entirety.

SUMMARY OF THE INVENTION

The present invention relates to an universal method for the large scale production of high-purity carrier free or non carrier added radioisotopes by applying a number of "unit operations" which are derived from physics and material science and hitherto not used for isotope production. A required number of said unit operations is combined, selected and optimised individually for each radioisotope production scheme. The use of said unit operations allows a batch wise operation or a fully automated continuous production scheme. The radioisotopes produced by the inventive method are especially suitable for producing radioisotope-labelled bioconjugates as well as particles, in particular nanoparticles and microparticles.

BACKGROUND OF THE INVENTION

Radioisotopes are widely used in the fields of life science, research and medicine, for example, in nuclear medicine, diagnosis, radiotherapy, biochemical analysis, as well as diagnostic and therapeutic pharmaceuticals.

One such important application for radioisotopes is the diagnosis and therapy of diseases, such as cancer. For example, there has been considerable progress during the last two decades in the use of radio-labelled tumor-selective monoclonal antibodies in the diagnosis and therapy of cancer. The concept of localizing the cytotoxic radionuclide to the cancer cell is an important supplement to conventional forms of radiotherapy. In theory the intimate contract between a radioactive antibody conjugate and a target cell enables the absorbed radiation dose to be concentrated at the site of abnormality with minimal injury to the normal surrounding cells and tissues [Bruland O S. Cancer therapy with radiolabelled antibodies. An overview. *Acta Oncol.* 1995; 34(8): 1085-94].

Furthermore, the use of monoclonal antibodies to deliver radioisotopes directly to tumor cells has become a promising strategy to enhance the antitumor effects of native antibodies. Since the alpha- and beta-particles emitted during the decay of radioisotopes differ in significant ways, proper selection of isotope and antibody combinations is crucial to making radioimmunotherapy a standard therapeutic modality. Because of the short path length (50-80 microm) and high linear energy transfer (approximately 100 keV/microm) of alpha-emitting radioisotopes, targeted alpha-particle therapy offers the potential for more specific tumor cell killing with less damage to surrounding normal tissues than beta-emitters. These properties make targeted alpha-particle therapy ideal for the elimination of minimal residual or micrometastatic disease. Radioimmunotherapy using alpha-emitters such as (213)Bi, (211) At, and (225)Ac has shown activity in several in vitro and in vivo experimental models as well as in clinical trials. Further advances will require investigation of more potent isotopes, new sources and methods of isotope production, improved chelation techniques, better methods for pharmacokinetic and dosimetric modeling, and new methods of isotope delivery such as pretargeting. [Mulford D A, Scheinberg D A, Jurcic J G. The promise of targeted alpha-particle therapy. *J Nucl Med.* 2005 January; 46 Suppl 1:199 S-204S.]

In addition, radioimmunotherapy (RIT) combines the advantages of targeted radiation therapy and specific immunotherapy using monoclonal antibodies. RIT can be used either to target tumor cells or to specifically suppress immunocompetent host cells in the setting of allogeneic transplantation. The choice of radionuclide used for RIT depends on its distinct radiation characteristics and the type of malignancy or cells targeted. In general, beta-emitters with their lower energy and longer path length are more suitable to target bulky, solid tumors whereas alpha-emitters with their high linear energy transfer and short path length are better suited to target hematopoietic cells (normal or malignant). Different approaches of RIT such as the use of stable radioimmunoconjugates or of pretargeting strategies are available. [Bethge W A, Sandmaier B M. Targeted cancer therapy using radiolabeled monoclonal antibodies. *Technol Cancer Res Treat.* 2005 August; 4(4):393-405.

Also the method SIRT (selective internal radiation therapy) or radioembolization has been developed which is similar to chemoembolization but uses radioactive microspheres (microscopic particles or beads). Thereby, radioisotopes are incorporated directly into the microspheres in order to deliver radiation directly to its destination, e.g. the tumor. The loaded spheres/beads are e.g. injected through a catheter into the blood vessel supplying the tumor. The spheres/beads become lodged within the tumor vessels where they deliver local radiation that causes tumor death. This technique allows for a higher dose of radiation to be used to kill the tumor without subjecting adjacent healthy tissue to harmful levels of radiation. Radioembolization has been described utilizing, for example, $^{90}$Y (Herba M J, Thirlwell M P. Radioembolization for hepatic metastases. *Semin Oncol.* 2002 April; 29(2):152-9.) or $^{188}$Re (Wunderlich G, Pinkert J, Stintz M, Kotzerke J. Labeling and biodistribution of different particle materials for radioembolization therapy with 188Re. *Appl Radiat Isot.* 2005 May; 62(5):745-50.)

However, the presently used methods in radioisotope production have reached their limits and there is a strong need for improved methods. This applies in particular to the isotopic purity, the specific activity and the range of available radionuclides.

With the growing complexity of positron emission tomography (PET)/single photon emission computed tomography (SPECT) imaging and the developments in systemic radionuclide therapy there is a growing need for radioisotope preparations with higher radiochemical and radionuclic purity that has not been achievable before. Especially important for the new applications is the specific activity of the radiotracer.

Furthermore, an implementation of the break-through in development of the drug target delivery systems of new methods of cancer therapy is limited due to the lack of availability of the existing radionuclides with optimal decay characteristics for such an application.

DETAILED DESCRIPTION OF THE INVENTION

An object of the present invention is, thus, to provide a method for the large scale production of high-purity radioisotopes, especially of carrier free or non carrier added radioisotopes.

Another object of the present invention is, thus, to provide uses of these radioisotopes.

The invention relates to a general method for industrial scale production of radioisotope preparations for life science research, medical application and industry. In particular it opens up for mass production of a number of rare isotopes that hitherto have not been available on the market and now are much in demand. By combining a number of physics unit operations with radiochemical unit operations the method allows to extract and refine any useful radioisotope from a suitable activated material in a non destructive and reusable way that generates a minimum of waste and almost no liquid waste. According to the method of the present invention target material activated by any method can be used as raw material.

A number of the isotopes of interest are abundantly produced by the high energy nuclear reactions that occur as by product in present and future high energy particle accelerators, experiments and other accelerator driven systems. In those facilities the method of the present invention permits to harvest the radioisotopes from their various waste products, their molten metal target and cooling media and spent beam absorbers or if needed from dedicated target stations sharing the primary particle beam.

According to the method of the present invention extraction of radionuclides from the irradiated material and their subsequent concentration and purification into monoisotopic samples is achieved by application of a number of innovative "unit operations" (see below, units 1-14) derived from physics and material science and hitherto not used for isotope production.

The required number of these unit operations of the present invention are combined, selected, put in the required order and optimised individually for each radioisotope production scheme. They allow a batch wise operation or a fully automated continuous production scheme.

In the following a list is given of these unit operations that also can be further combined if needed with more conventional radiochemical methods in order to obtain a given product:

Unit 1: Activation (i.e. irradiation with charged particles, neutrons, electrons or gamma-rays) of target materials that allow pyrochemical or pyrometallurgical treatment to produce the radioisotopes of interest or their predecessors.

Unit 2: Transport of the element in question to the surface of the target material is accomplished by means of high temperature diffusion in the solid or liquid target matrix.

Unit 3: Separation of the element in question from the bulk target material can be achieved by high temperature desorption from the target surface under vacuum or in inert atmosphere (e.g. He, Ar, . . . ).

Unit 4: Separation of the element in question from the bulk target material can be achieved by removing the target material by high temperature sublimation under vacuum or in inert atmosphere if the element in question is less volatile than the target material.

Unit 5: Separation of the element in question from the bulk target material can be achieved by adsorption on suitable substrates located in the flow of a liquid metal target and coolant medium.

Unit 6: Desorption of the element in question from the bulk target material can be assisted by means of the chemical evaporation technique, i.e. the addition of chemical reactive gases that form in-situ more volatile compounds of the element in question.

Unit 7: Transport of the element or chemical compound in question to further purification steps is accomplished by molecular flow at high temperature or by a gas flow.

Unit 8: Condensation or adsorption on a surface compatible with the purity requirement of an accelerator ion-source.

Unit 9: Conditioning for ionisation in the ion sources by addition of suitable chemicals that either allow pyrochemical reduction to the elementary state or oxidation/molecule formation on the other hand and controlling the mass separation process i.e. mass marking.

Unit 10: Introduction of the sample into an oven from where the sample is fed into the ion source by raising the oven temperature in a controlled way.

Unit 11: Use of various types of ion-sources optimised for an isotope of the element in question, e.g. surface ionisation, resonant laser ionisation or plasma ionisation.

Unit 12: Acceleration of the radioactive ion-beam extracted from the ion source with a dc or ac acceleration voltage.

Unit 13: Separation of the ion beam in a suitable mass selective device, e.g. a magnetic sector field, a Wien-filter or a radio-frequency multipole.

Unit 14: Use is made of the momentum imparted to the mass separated nuclides in order to collect them by implantation into a suitably prepared chemical substrate, e.g. nanoparticles or microparticles, macromolecules, microspheres, macroaggregates, ion exchange resins or other matrices used in chromatographic systems.

Application unit: Application of the obtained isotopes in research and medicine, for diagnosis and/or therapy of diseases, such as in vivo and in vitro applications, e.g. RIT, biodistribution studies, PET imaging, SPECT, gamma-spectrometry, TAT, radioembolization, Auger-therapy etc.

Unit operation 1 is also called the "production" unit operation.

Unit operations 2-14 are also called the "separation" unit operations.

Although the method of the invention (units 1-14) allows harvesting the radioisotopes independent on the mode of activation the synergy with present and future high energy particle accelerators, experiments and other accelerator driven systems is obvious. A number of the isotopes of interest are abundantly produced by the high energy nuclear reactions that occur as by-product in various locations:

1. Target of the type where a circulating molten metal is used as combined target and heat transfer medium. In a bypass line of this metal flow the radio isotopes of interest can be continuously extracted.
2. Any sufficiently irradiated structure disposed of as waste.
3. Dedicated targets and ion-source units irradiated in the primary particle beam or in its spent beam absorber.

Finally the method of the present invention lends itself to build a radioisotope factory in which the radioisotopes are produced on-line in a continuous process where dedicated target and mass separator stations share the primary beam.

Improvements and Advantages

- The mass separating step of the method according to the invention fulfils the newly formulated higher quality standards by producing mono isotopic samples without any stable isotope of the element in question. This form features the highest possible and achievable specific activity of a radionuclide, also called "carrier free".
- Almost all useable nuclides in the chart of nuclides can be produced so that radionuclides that are better adapted to their applications can be selected in amounts that also allow widespread use of the upcoming methods for radiotherapy.
- The method is independent of the nuclear reaction used to produce the radioactivity.
- The method allows a cost efficient extraction of the wanted nuclei from a number of by products available in present and future accelerator projects and to facilitate the control and disposal of their radioactive waste inventory.

The inclusion of ion-beam formation and acceleration as production stages facilitates the process of labelling of the pharmaceutical end product and production of new isotope generators.

This method uses rather non destructive dry techniques that often allow reusing the target and mainly produces solid waste products with much less liquid waste as in the present production that proceeds via dissolution of the targets.

The radioisotope labelled bioconjugates preferably can be used in radio-immunotherapy of diseases, such as cancer, e.g., in targeted alpha therapy (TAT).

The method which is provided by the present invention preferably comprises the following steps:

(a) Activation of a target by a particle beam,
(b) Separation of the isotope from the irradiated target,
(c) Ionisation of the separated isotope,
(d) Extraction from the ion source and acceleration of the ion beam,
(e) Mass-separation,
(f) Collection of the isotope.

wherein step (a) comprises unit operation 1,
wherein step (b) comprises unit operation 2, 3, 4 and/or 5,
wherein step (c) comprises unit operation 11,
wherein step (d) comprises unit operation 12,
wherein step (e) comprises unit operation 13, and
wherein step (f) comprises unit operation 14.

Thus, one preferred combination of the unit operations utilizes units 1 and 2 (or 3 or 4 or 5) and 11-14.

A combination of units 1, 2, 3 and 11-14 is preferred, such as for the production of carrier-free radioisotopes of the rare earth elements.

A combination of units 1, 2, 3, 7 and 11-14 is preferred, such as for the on- or off-line extraction of radioisotopes from a high power liquid metal target, for the production of radioisotopes relevant for targeted alpha therapy (TAT) via continuous or batch-mode extraction from actinide targets, for the on-line production of carrier-free $^{204\text{-}210}At$ as well as for the production of carrier-free radioisotopes of the rare earth elements.

Furthermore, a combination of units 1, 2, 3, 7, 8, 10 and 11-14 is preferred, such as for the on-line production of carrier-free $^{204\text{-}210}At$.

Also the combination of units 1, 2, 3, 7 and 8 is suitable, such as for the on-line production of carrier-free $^{211}At$ or $^{204\text{-}210}At$ as well as for the production of carrier-free radioisotopes of the rare earth elements.

Further preferred combinations are the combinations of units 1, 2, 4 (or 5), 8, 10 and 11-14; units 1, 7, 8, 10 and 11-14; units 1, 2, 3, 10, and 11-14; units 1, 2, 3, 6, 7 and 11-14.

The combinations of units 1, 9, 10, 11, 12 and 13 as well as units 1, 2, 3, 7, 9, 11, 12 and 13 are also preferred, such as for the fission production of neutron-rich lanthanide and tin isotopes.

Furthermore, for the fission production of isotopes, such as neutron-rich lanthanide and tin isotopes, a method comprising the following steps is preferred:

(a) Activation of a fission target by a particle beam,
(b) Separation of the isotope from the irradiated target, and
optionally, (c) uonisation of the separated isotope,
optionally, (d) Extraction from the ion source and acceleration of the ion beam,
optionally, (e) Mass-separation,
optionally, (f) Collection of the isotope, wherein step (a) comprises unit operation 1,
wherein step (b) comprises unit operation 2, 3, 4 and/or 5,
wherein step (c) comprises unit operation 11,
wherein step (d) comprises unit operation 12,
wherein step (e) comprises unit operation 13, and
wherein step (f) comprises unit operation 14.

Unit operations 10 to 13 of the method of the present invention can also preferably be combined for the mass-separation of radioisotopes that were created and separated in any other way (e.g. commercially available radioisotopes) and hence to increase the specific activity of the resulting radioisotope preparation.

Furthermore, unit operations 10 to 14 can also preferably be used to implant radioisotopes that were created and separated in any other way (e.g. commercially available radioisotopes) into nanoparticles, macromolecules, microspheres, macroaggregates, ion exchange resins or other matrices used in chromatographic systems. In this case, unit 13 is optional if the specific activity of the original radioisotope preparation has already sufficient specific activity and radioisotopic purity for the application. The so marked substrates may either be used directly for in vitro or in vivo applications (e.g. nanoparticles, microspheres, . . . for radioembolization therapy, see e.g. Wunderlich et al. Labeling and biodistribution of different particle materials for radioembolization therapy with $^{188}Re$. *Appl Radiat Isot.* 2005 May; 62(5):745-50.) or for subsequent chemical steps (e.g. ion exchange resins or other matrices used in chromatographic systems) or biochemical steps.

Certain elements can be brought into a chemical form which is already volatile at room temperature and can thus be conveniently injected in gaseous form into an ion source. For metallic elements this method is known under the name MIVOC (metal ions from volatile compounds). E.g. iron can be introduced as ferrocene $Fe(C_5H_5)_2$, zinc as dimethylzinc $C_2H_6Zn$, germanium as tetraethylgermanium $Ge(C_2H_5)_4$, molybdenum as molybdenumhexacarbonyl $Mo(CO)_6$, etc. For all these cases an oven is not absolutely necessary and unit operation 10 can be replaced by unit operation 9.

The isotopes obtained by the method according to the invention are preferably $^{225}Ac$, $^{224}Ra$, $^{223}Ra$, $^{213}Bi$, $^{211}At$, $^{152}Tb$, $^{149}Tb$, $^{44}Sc$, $^{153}Sm$, $^{82}Sr$ or $^{82}Rb$.

The production of the following isotopes is also preferred: $^{28}Mg$, $^{26}Al$, $^{32}Si$, $^{32}P$, $^{33}P$, $^{42}Ar$, $^{42}K$, $^{43}K$, $^{45}Ca$, $^{47}Ca$, $^{44}Sc$, $^{44m}Sc$, $^{46}Sc$, $^{47}Sc$, $^{44}Ti$, $^{52}Mn$, $^{54}Mn$, $^{56}Mn$, $^{52}Fe$, $^{55}Fe$, $^{59}Fe$, $^{55}Co$, $^{56}Co$, $^{57}Co$, $^{58}Co$, $^{62}Cu$, $^{64}Cu$, $^{67}Cu$, $^{62}Zn$, $^{68}Ga$, $^{68}Ge$, $^{72}As$, $^{72}Se$, $^{73}Se$, $^{75}Se$, $^{75}Br$, $^{76}Br$, $^{77}Br$, $^{75}Kr$, $^{76}Kr$, $^{77}Kr$, $^{81}Rb$, $^{82}Rb$, $^{82}Sr$, $^{83}Sr$, $^{85}Sr$, $^{89}Sr$, $^{85}Y$, $^{86}Y$, $^{87}Y$, $^{88}Y$, $^{89}Zr$, $^{90}Nb$, $^{97}Ru$, $^{103}Pd$, $^{103}Cd$, $^{111}Ag$, $^{113}Sn$, $^{117m}Sn$, $^{119}Sb$, $^{121m}Te$, $^{121}I$, $^{122}I$, $^{123}I$, $^{124}I$, $^{125}I$, $^{126}I$, $^{130}I$, $^{121}Xe$, $^{122}Xe$, $^{123}Xe$, $^{125}Xe$, $^{127}Xe$, $^{129m}Xe$, $^{131m}Xe$, $^{131m,g}Xe$, $^{134}Ce/La$, $^{137}Ce$, $^{139}Ce$, $^{141}Ce$, $^{143}Pr$, $^{138}N/Pr$, $^{140}Nd/Pr$, $^{147}Nd$, $^{149}Pm$, $^{142}Sm/Pm$, $^{153}Sm$, $^{155}Eu$, $^{147}Gd$, $^{148}Gd$, $^{149}Gd$, $^{149}Tb$, $^{152}Tb$, $^{155}Tb$, $^{161}Tb$, $^{157}Dy$, $^{159}Dy$, $^{166}Ho$, $^{165}Er$, $^{169}Er$, $^{165}Tm$, $^{167}Tm$, $^{169}Yb$, $^{177}Yb$, $^{172}Lu$, $^{177}Lu$, $^{172}Hf$, $^{175}Hf$, $^{178}Ta$, $^{178}W$, $^{188}W$, $^{186}Re$, $^{188}Re$, $^{192}Ir$, $^{195}Au$, $^{198}Au$, $^{194}Hg$, $^{194}Hg$, $^{197}Hg$, $^{201}Tl$, $^{202}Tl$, $^{211}Pb$, $^{212}Pb$, $^{212}Bi$, $^{213}Bi$, $^{204}At$, $^{205}At$, $^{206}At$, $^{207}At$, $^{208}At$, $^{209}At$, $^{210}At$, $^{211}At$, $^{220}Rn$, $^{221}Rn$, $^{220}Fr$, $^{221}Fr$, $^{223}Ra$, $^{224}Ra$, $^{225}Ra$, $^{225}Ac$, $^{227}Ac$, $^{227}Th$ or $^{228}Th$.

Preferably, radioisotopes in carrier-free or non-carrier added form are produced by the method of the present invention.

Preferred is a method according to the invention, wherein the target that is activated by a particle beam is a metal or alloy or another high temperature compound (preferably carbide, oxide, etc). Preferred targets suitable in the present invention are Ta foil, Hg, Pb, Bi, Pb/Bi alloy, Ti, Th, U, Nb, Mo, Hf, W, $ThC_x$, $UC_x$ $ThO_2$ or an isotopically enriched target material, such as $^{152}Gd$, $^{144}Sm$ or others.

Preferably, the target is heated during or after the activation step (unit 1). In one embodiment, the target is heated above 2,000° C. However, the temperature depends on the target material and the element to be released. In one embodiment, the target is kept in a molten state, in particular elements like Hg, Pb or Bi. In other embodiments, the target is kept solid, in particular refractory elements like Nb, Mo, Hf. Ta, W or refractory compounds like $ThC_x$, $UC_x$.

Preferably, the particles in the particle beam used to activate the target are charged or neutral particles, protons, electrons, neutrons, photons. Preferably, the particle beam has an energy in the range of a few or several ten MeV to several GeV. In few cases it is necessary to restrict the particle energy to a more narrow range to avoid production of disturbing contaminations, e.g. an alpha energy <30 MeV is preferred for the production of $^{211}At$ via $^{209}Bi$(alpha,2n). Preferably, the particle beam is provided by a particle accelerator, such as cyclotron, LINAC, synchrotron.

Preferably, the separation of the isotopes from the irradiated target is carried out by bringing the target to high temperature, e.g. solid targets to 60-95% of their melting point, under vacuum, e.g. in the order of $10^{-5}$ mbar or better, or suitable gas atmosphere. A preferred suitable gas atmosphere is a noble gas (He, Ne, Ar, . . . ) that is not reacting with the hot target. Occasionally reactive gases like $O_2$, $CF_4$, . . . are added in an amount not deleterious for the target but sufficiently high to favour the release of the wanted isotopes, e.g. at a partial pressure in the order of $10^{-4}$ mbar.

Step (b) preferably comprises

- the transport of the isotope of interest to the surface of the target material by means of high temperature diffusion, and/or
- the separation of the isotope of interest from the bulk target material by high temperature desorption from the target surface under vacuum or in inert atmosphere, and/or
- the separation of the isotope of interest from the bulk target material by removing the target material by high temperature sublimation under vacuum or in inert atmosphere, and/or
- the separation of the isotope of interest from the bulk target material by adsorption on suitable substrates located in the flow of a liquid metal target and coolant medium, and/or
- the desorption of the isotope of interest from the bulk target material by means of chemical evaporation.

Between steps (b) and (c) the isotope of interest is preferably transported by molecular flow at high temperature or by a gas flow.

Between steps (b) and (c) the isotope of interest is preferably condensed or adsorbed on a surface compatible with the purity requirement of an accelerator ion source.

The isotope of interest is preferably conditioned for ionisation in the ion source by adding chemicals that allow pyrochemical reduction to the elementary state, oxidation or molecule formation. The mass separation process is preferably controlled by mass marking.

Before step (c) the isotope of interest is preferably introduced into an oven from where the sample is fed into the ion source.

Preferably, the ionisation in step (c) is surface ionisation, laser ionisation or plasma ionisation. Elements or compounds with low ionization potential, i.e. elements of the chemical groups 1 and 3 (including many lanthanides) and heavier elements of the group 2, are most easily ionized by surface ionization. Resonant laser ionisation provides an efficient and selective ionization mode for most metallic elements. Plasma ionisation is intrinsically less selective, but compatible with practically all elements and compounds.

Preferably, the mass separation step is an on-line or off-line mass separation. On-line mass separation is preferred for short-lived isotopes where a longer delay would cause unacceptable decay losses. Off-line mass separation is preferred for longer-lived isotopes where a delay is less important and in cases where technical reasons prevent a direct coupling of the production target to an on-line mass separator.

Step (f) preferably comprises that the isotope of interest is collected by implantation into a prepared chemical substrate. Preferably, a further purification step follows the collection of the isotope in step (f).

Preferably, all steps (a) to (f) are repeated or the irradiated target material of step (a) is reused. The steps can be repeated, one time, two times, three times or as often as necessary to obtain the required purity.

The radioisotopes produced by the method of the present invention are preferably used for producing radioisotope-labelled bioconjugates or radioisotope-labelled nanoparticles, microspheres or macroaggregates.

Preferred bioconjugates are immuno-conjugates, antibodies, antibody fragments, such Fv, Fab, scFv, heavy and light chains, chimeric antibodies or antibody fragments, humanized antibodies or antibody fragments proteins, peptides, nucleic acids, such as RNA, DNA and modifications thereof, such as PNA, and oligonucleotides or fragments of any of them.

Bioconjugates are any wildtype or recombinant protein (such as monoclonal antibodies, their fragments, human serum albumin (HSA)) as well as microspheres or macroaggregates made from said proteins, peptides and/or oligonucleotides.

Bioconjugates further comprise nanoparticles, microspheres or macroaggregates that are conjugated with or covalently or noncovalently attached to said immuno-conjugates, antibodies, proteins, peptides, nucleic acids, oligonucleotides or fragments thereof.

Bioconjugates can carry linker molecules or tags for molecular recognition, purification and/or handling purposes, such as avidin, streptavidin, biotin, protein A or G, fluorophores, dyes, chromophores. However, such linker molecules and tags are well known to the person of skill in the art.

Preferably, the bioconjugates further comprise chelating groups, such as derivatives of DTPA or DOTA, with or without linking molecules for the labelling with the isotopes.

The radioisotope-labelled bioconjugates can preferably used for diagnostic procedures or therapeutic protocols, such as SPECT, quantitative PET imaging for individual in vivo dosimetry, RIT, TAT, Auger-therapy or radioembolization.

The radioisotopes produced by the method of the present invention, preferably $^{204}At$, $^{205}At$, $^{206}At$, $^{207}At$, $^{708}At$, $^{209}At$ or $^{210}At$, can be used for in vitro or in vivo biodistribution studies or dosimetry via PET, gamma-spectrometry or SPECT.

The mass-separated ion-beam is preferably implanted into an implantation substrate (unit operation 14).

The implantation energy is preferably selected in order to adjust the implantation depth. By selecting the implantation energy, the implantation depth can be adjusted that alpha-recoils can either be ejected and emanate (implantation energy typically <100 keV leads to a low implantation depth), thus representing an open source, or that alpha-recoils cannot leave the matrix (implantation energy typically >150 keV leads to a deeper implantation depth), hence representing a closed source.

The implantation is preferably performed through a thin cover layer into the implantation substrate.

Thus the source can be transported as "closed". The end user can easily remove the cover layer by dissolving, evaporating, burning, mechanically removing, etc. to obtain an open source with well-defined depth profile.

The implantation substrate is preferably a salt layer, a water-soluble substance, such as sugars, a thin ice layer of frozen water or another liquid or a solid matrix, such as a metal foil.

The separation from the salt layer containing the radioisotopes preferably comprises subsequent dissolving in a small volume of water or the eluting agent, and/or as such direct injection into the chromatographic system.

The separation from the thin ice layer containing the radioisotopes preferably comprises subsequent melting by heating, with any suitable method (Ohmic heating, infrared heating, radio-frequency heating, . . . ).

The separation from the solid matrix, such as a metal foil, preferably requires additional chemical separation from the matrix material.

Instead of a soluble matrix, the ion beam can also be implanted into any other solid matrix, e.g. a metal foil. In this case one needs additionally a chemical separation of the desired isotope from the matrix material that usually disturbs the chromatographic process.

It is furthermore preferred that conventional radio-chemical and radio-chromatographical processes are performed, such as precipitation, electrochemical separations, extraction, cation exchange chromatography, anion exchange chromatography, extraction chromatography, thermo chromatography, gas chromatography.

The separation from the implantation substrate preferably comprises thermal release from a refractory matrix.

A particularly simple and efficient separation from the implantation substrate can be achieved by thermal release from a refractory matrix.

The present invention further provides a method for direct radioisotope-labelling of bioconjugates, comprising (i) performing the method for the production of high-purity isotopes according to the invention as described above, (ii) obtaining the product fraction containing the radioisotope of interest in a small volume, and (ii) direct radioisotope-labelling of bioconjugates and/or direct injection into a chromatographic system for further purification, wherein the bioconjugates are as defined above.

The bioconjugates further preferably comprise nanoparticles, microspheres or macroaggregates that are conjugated with or covalently or noncovalently attached to said immunoconjugates, antibodies, proteins, peptides, nucleic acids, oligonucleotides or fragments thereof.

The radioisotope-labelled bioconjugates obtained by the bioconjugate-labelling method (see above) are preferably used in radio-immunotherapy (RIT) of diseases, such as cancer. Said radioisotope-labelled bioconjugates are preferably used for diagnostic procedures, such as SPECT, quantitative PET imaging for individual in vivo dosimetry, or for therapeutic protocols, such as RIT, TAT or Auger-therapy.

Further preferred implantation substrates are nanoparticles, macromolecules, microspheres, macroaggregates, ion exchange resins or other matrices used in chromatographic systems.

The present invention further provides a method for direct labelling of nanoparticles, macro-molecules, micro-spheres, macro-aggregates, ion exchange resins or other matrices used in chromatographic systems, comprising (i) performing the method for the production of high-purity isotopes according to the invention as described above, (ii) direct implanting of the radioactive ion beam into said nanoparticles, macro-molecules, micro-spheres, macro-aggregates, ion exchange resins or other matrices used in chromatographic systems.

Preferably, step (ii) of the above method is carried out on-line. Alternatively, after the standard purification steps of step (i) the product is again injected into an ion source, ionized, accelerated and then step (ii) is performed.

Furthermore, unit operations 10 to 14 can also preferably be used to implant radioisotopes that were created and separated in any other way (e.g. commercially available radioisotopes) into nanoparticles, macromolecules, microspheres, macroaggregates, ion exchange resins or other matrices used in chromatographic systems. In this case, unit 13 is optional if the specific activity of the original radioisotope preparation has already sufficient specific activity and radioisotopic purity for the application. The so marked substrates may either be used directly for in vitro or in vivo applications (e.g. nanoparticles, microspheres, . . . for radioembolization therapy, see e.g. Wunderlich et al. Labeling and biodistribution of different particle materials for radioembolization therapy with $^{188}$Re. *Appl Radiat Isot.* 2005 May; 62(5):745-50.) or for subsequent chemical steps (e.g. ion exchange resins or other matrices used in chromatographic systems) or biochemical steps.

Therefore, the present invention further provides a method for direct labelling of nanoparticles, macro-molecules, micro-spheres, macro-aggregates, ion exchange resins or other matrices used in chromatographic systems, comprising the following steps:

(a) Obtaining a sample of an isotope, such as a commercially available isotope, (b) Introduction of said isotope into an oven from where said sample is fed into an ion source, (c) Ionisation of said isotope, (d) Extraction from the ion source and acceleration of the ion beam, (e) optionally, Mass-separation, (f) Collection of the isotope by direct implanting of the radioactive ion beam into said nanoparticles, macro-molecules, micro-spheres, macro-aggregates, ion exchange resins or other matrices used in chromatographic systems.

wherein step (b) comprises unit operation 10,
wherein step (c) comprises unit operation 11,
wherein step (d) comprises unit operation 12,
wherein step (e) comprises unit operation 13, and
wherein step (f) comprises unit operation 14.

The invention further provides a device for performing the method for the production of high-purity isotopes according to the invention, as described above.

The invention further provides the use of said device as a dry-isotope generator, in particular dry $^{62}$Zn/$^{62}$Cu, $^{228}$Th/$^{224}$Ra, $^{224}$Ra/$^{212}$Pb/$^{212}$Bi, $^{228}$Th/$^{212}$Pb/$^{212}$Bi, $^{225}$Ac/$^{213}$Bi, $^{227}$Ac/$^{227}$Th/$^{223}$Ra, $^{44}$Ti/$^{44}$Sc generator.

The invention further provides a device for performing the method for direct radioisotope-labelling of bioconjugates, as described above.

The invention further provides a device for performing the method for direct labelling of nanoparticles, macro-molecules, micro-spheres, macro-aggregates, ion exchange resins or other matrices used in chromatographic systems, as described above.

The present invention also provides a method for the large scale production of high-purity carrier-free or non carrier added radioisotopes comprising the following steps:

(a) Activation of a target by a particle beam,
(b) Separation of the isotope from the irradiated target,
(c) Ionisation of the separated isotope,
(d) Extraction from the ion source and acceleration of the ion beam,
(e) Mass-separation,
(f) Collection of the isotope,
wherein the isotopes are produced by on- or off-line extraction of radioisotopes from a high power liquid metal target.

The present invention also provides a method for the large scale production of high-purity carrier-free or non carrier added radioisotopes comprising the following steps:

(a) Activation of a target by a particle beam,
(b) Separation of the isotope from the irradiated target,
(c) Ionisation of the separated isotope,
(d) Extraction from the ion source and acceleration of the ion beam,
(e) Mass-separation,
(f) Collection of the isotope,
wherein the isotope are produced via continuous or batch-mode extraction from targets.

The present invention also provides a method for the large scale production of high-purity carrier-free radioisotope $^{211}$At comprising the following steps:

(a) Activation of a target by a particle beam,
(b) Separation of the isotope from the irradiated target,
(c) Ionisation of the separated isotope,
(d) Extraction from the ion source and acceleration of the ion beam,
(e) Mass-separation,
(f) Collection of the isotope,
wherein the isotope is produced on-line, and
wherein the produced isotope is the carrier-free radioisotope $^{211}$At.

The present invention also provides a method for the large scale production of high-purity carrier-free radioisotopes comprising the following steps:

(a) Activation of a target by a particle beam,
(b) Separation of the isotope from the irradiated target,
(c) Ionisation of the separated isotope,
(d) Extraction from the ion source and acceleration of the ion beam,
(e) Mass-separation,
(f) Collection of the isotope,
wherein the isotopes are produced on-line, and
wherein the produced isotopes are the carrier-free radioisotopes $^{204-210}$At.

The present invention also provides a method for the large scale production of high-purity carrier-free radioisotopes of the rare earth elements comprising the following steps:

(a) Activation of a target by a particle beam,
(b) Separation of the isotope from the irradiated target,
(c) Ionisation of the separated isotope,
(d) Extraction from the ion source and acceleration of the ion beam,
(e) Mass-separation,
(f) Collection of the isotope,
wherein the produced isotopes are carrier free radioisotopes of the rare earth elements The present invention also provides a method for the large scale production of high-purity carrier-free or non carrier added neutron-rich lanthanide and tin isotopes comprising the following steps:

(a) Activation of a fission target by a particle beam,
(b) Separation of the isotope from the irradiated target, and
optionally, (c) Ionisation of the separated isotope,
optionally, (d) Extraction from the ion source and acceleration of the ion beam,
optionally, (e) Mass-separation,
optionally, (f) Collection of the isotope,
wherein the neutron-rich lanthanide and tin isotopes are produced by fission.

Unit operations 10 to 13 of the method of the present invention can also preferably be combined for the mass-separation of radioisotopes that were created and separated in any other way (e.g. commercially available radioisotopes) and hence to increase the specific activity of the resulting radioisotope preparation.

A preferred method for such mass-separation of isotopes comprises the following steps:

(a) Obtaining a sample of an isotope, such as a commercially available isotope,
(b) Introduction of said isotope into an oven from where said sample is fed into an ion source,
(c) Ionisation of said isotope,
(d) Extraction from the ion source and acceleration of the ion beam,
(e) Mass-separation.
wherein step (b) comprises unit operation 10,
wherein step (c) comprises unit operation 11,
wherein step (d) comprises unit operation 12, and
wherein step (e) comprises unit operation 13.

Other preferable aspects of the invention will become apparent from the detailed description of preferred embodiments and aspects thereof.

The features of the present invention disclosed in the specification, the preferred embodiments and aspects, the examples, the claims and/or in the accompanying figures, may, both separately, and in any combination thereof, be material for realizing the invention in various forms thereof.

For the purposes of the present invention, all references as cited herein are incorporated by reference in their entireties.

Definitions:

The following terms and abbreviations are used throughout the description and examples:

First of all, the terms “radioisotopes” and “radionuclides” are used interchangeably throughout the description.

“Spallation” means a nuclear reaction occurring for incident particle energies >100 MeV. The method of the present invention preferably uses high energy particles (>100 MeV). Because when beams with lower energy are used reduced production cross-sections and also some production of products close-by to the target nuclides can occur. However, the method of the present invention also uses high energy particles with an energy lower than 100 MeV, such as 80 or 90 MeV.

The energy limits used throughout the description, embodiments, aspects, examples and claims of the present invention are not to be considered as sharp but rather indicative, allowing an application of lower-energy beams during the separation (such as unit operations 2-14) and during production (such as unit operation 1).

A preparation of a given radioisotope is “carrier free”, when it is free from other isotopes (both stable and radioactive) of the element in question. However, the term “carrier free” also comprises preparations, where the wanted radioisotope is absolutely dominating the total activity and radiotoxicity over radioisotopes of the same element and where stable isobars of the same element that would cause significant differences in the application to that of a pure radioisotope are not be present.

A preparation of a given radioisotope is "non carrier added", when special attention has been paid to procedures, equipment and material in order to minimize the introduction of other isotopes (both stable and radioactive) of the element in question in the same chemical form or as a species enabling isotopic exchange reactions. In the method of the present invention no stable or radioactive isotopes of the same element are added on purpose, though some amount may be intrinsically present due to the production process.

The "target" is that part of a radioisotope production system which is exposed to the beam inducing nuclear reactions in it. The target "matrix" is more specifically the inner part of the target where the wanted nuclear reactions occur. The target "matrix" does not contain the surrounding target container, etc.

"Effusion" defines diffusion in open space (e.g. under vacuum). Similar to the diffusion in solids or liquids "effusion" is a random walk process described by similar mathematical concepts. Effusing isotopes are those, which have already left the target matrix, i.e. have already desorbed.

"Release" requires the diffusion to the surface of the matrix plus desorption.

In case of an "on-line" mode, the part of a device performing the separation (such as unit operations 2-14) of the method of the invention is directly connected to the part of the device performing the production (such as unit operation 1) and operates simultaneously to the production. Whereas in case of an "off-line" mode, the separation starts after a stop of the production or batch-wise by removing target material from the irradiation region before separation.

"ADS" (Accelerator Driven Systems) are subcritical nuclear reactors where the neutrons necessary to maintain a continuous chain reaction are supplied by an (accelerator driven) spallation neutron source (or by breakup of deuteron beams).

"MEGAPIE" is a demonstrator experiment for a megawatt liquid metal target at the Paul Scherrer Institute.

In the "ISOL" (Isotope Separation On-Line) method thick targets are bombarded with a primary beam to produce nuclear reaction products. The latter are first stopped in the target matrix, then diffuse out of it, desorb from its surface, get to an ion source where they are ionised, extracted, slightly accelerated and mass-separated.

"RIT" (Radio-Immuno Therapy) is an immunotherapy where the agents (monoclonal antibodies, etc.) are conjugated with radioisotopes. The decay of the latter destroys or harms preferentially the environment, i.e. the cancer cells or any other illness related unit in the body.

"TAT" (Targeted Alpha Therapy) is a RIT using alpha emitting radioisotopes.

"PET" (Positron Emission Tomography): A radioactive tracer isotope which decays by emitting a positron, chemically incorporated into a molecule, is injected into the living subject (usually into blood circulation). There is a waiting period while the molecule becomes concentrated in tissues of interest, then the subject is placed in the imaging scanner. The isotope decays, emitting a positron. After traveling up to a few millimeters the positron annihilates with an electron, producing a pair of annihilation photons (511 keV) moving in opposite directions. These are detected when they reach a scintillator material in the scanning device, creating a burst of light which is detected by photomultiplier tubes. The technique depends on coincident detection of the pair of photons; photons which do not arrive in pairs (i.e., within a few nanoseconds) are ignored. By measuring where the annihilation photons end up, their origin in the body can be plotted, allowing the chemical uptake or activity of certain parts of the body to be determined. The scanner uses the pair-detection events to map the density of the isotope in the body, in the form of slice images separated by some millimeters. The resulting map shows the tissues in which the molecular probe has become concentrated, and is read by a nuclear medicine physician or radiologist, to interpret the result in terms of the patient's diagnosis and treatment.

"SPECT" (Single Photon Emission Computed Tomography) is a nuclear medicine tomographic imaging technique using gamma rays. The technique results in a set of image slices through a patient, showing the distribution of a radiopharmaceutical. Firstly a patient is injected with a gamma-emitting radiopharmaceutical. Then a series of projection images are acquired using a gamma camera. The acquisition involves the gamma camera rotating around the patient acquiring images at various positions. The number of images and the rotation angle covered varies depending on the type of investigation required.

The preferred embodiments and preferred aspects as well as the examples of the present invention shall now be further described with reference to the accompanying figures without being limited thereto.

FIGURES

Figure 2:
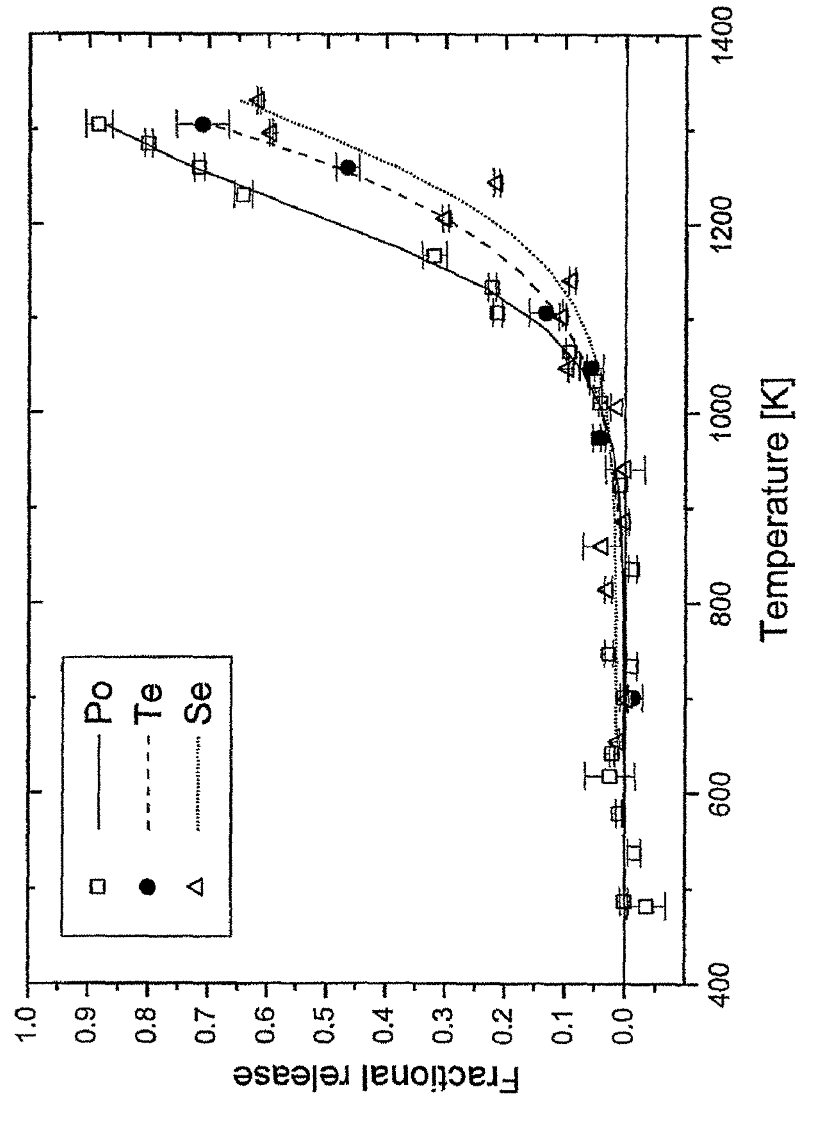

FIG. 2: Comparison of the release behaviour of selenium, tellurium and polonium from LBE (1 h experiments) in an Ar/7%-$H_2$ atmosphere as a function of temperature.

Figure 3:
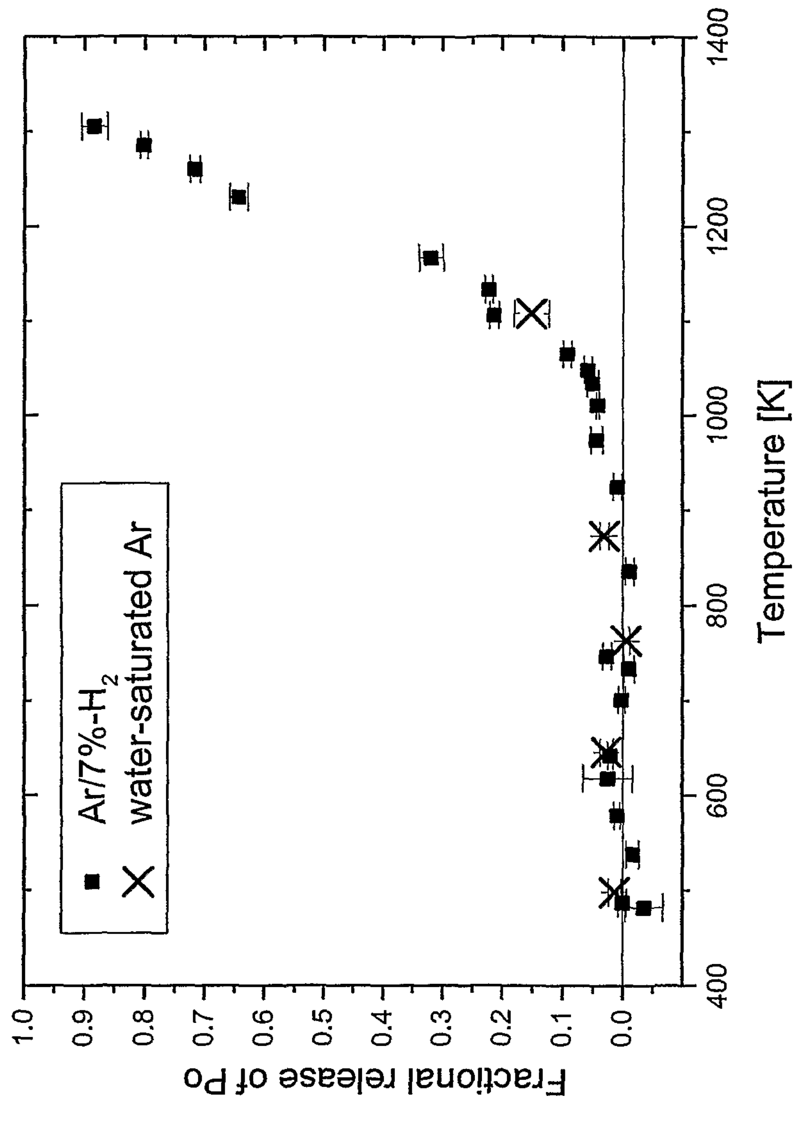

FIG. 3: Comparison of the release of polonium from LBE (1 h experiments) in Ar/7%-$H_2$ and water saturated Ar atmospheres as a function of temperature.

Figure 4:
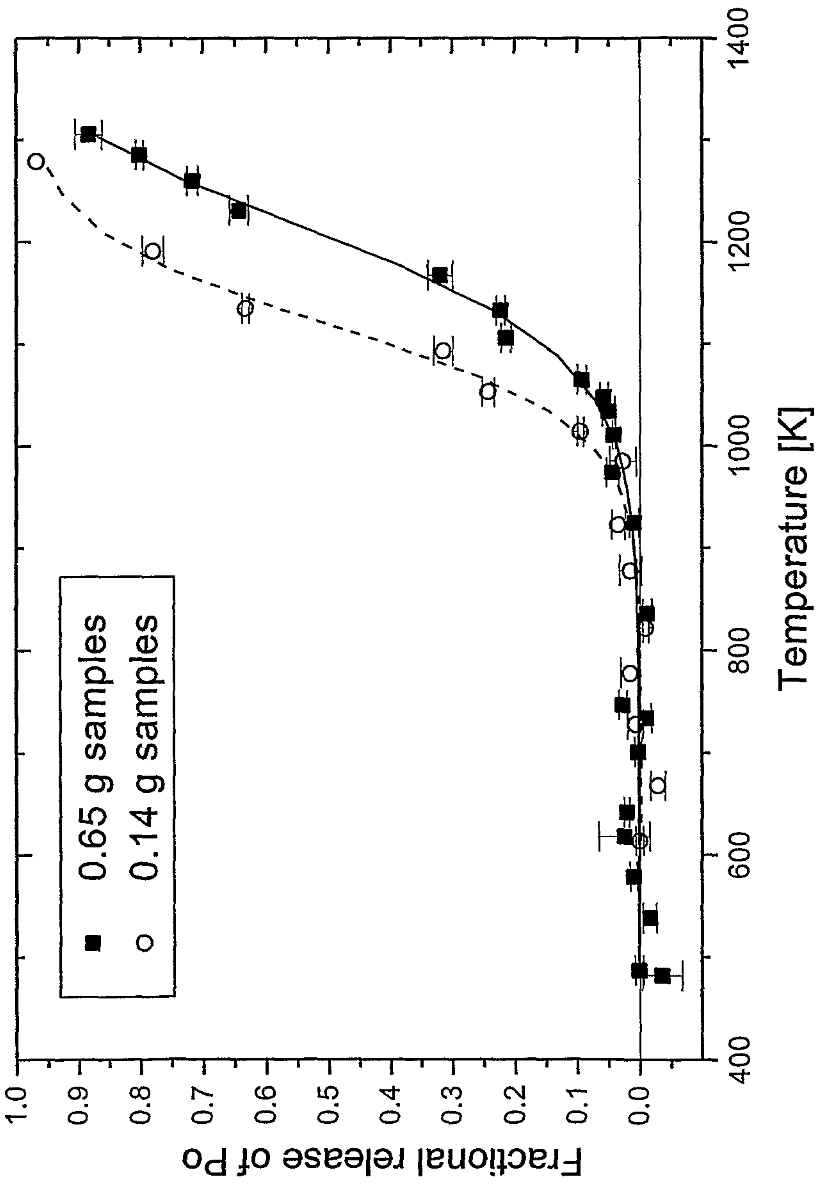

FIG. 4: Comparison of the release behaviour of polonium from LBE (1 h experiments) using different sample sizes in an Ar/7%-$H_2$ atmosphere as a function of temperature.

Figure 5:
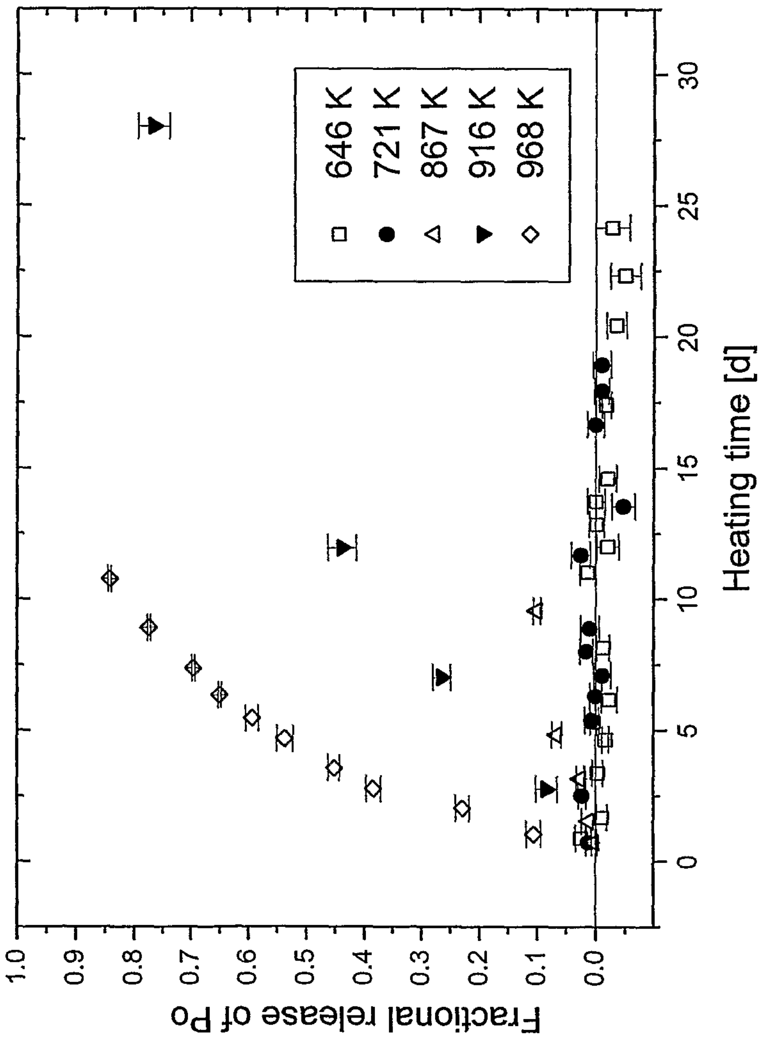

FIG. 5: Comparison of the long-term polonium release from LBE in an Ar/7%-$H_2$ atmosphere at different temperatures as a function of heating time.

Figure 6:
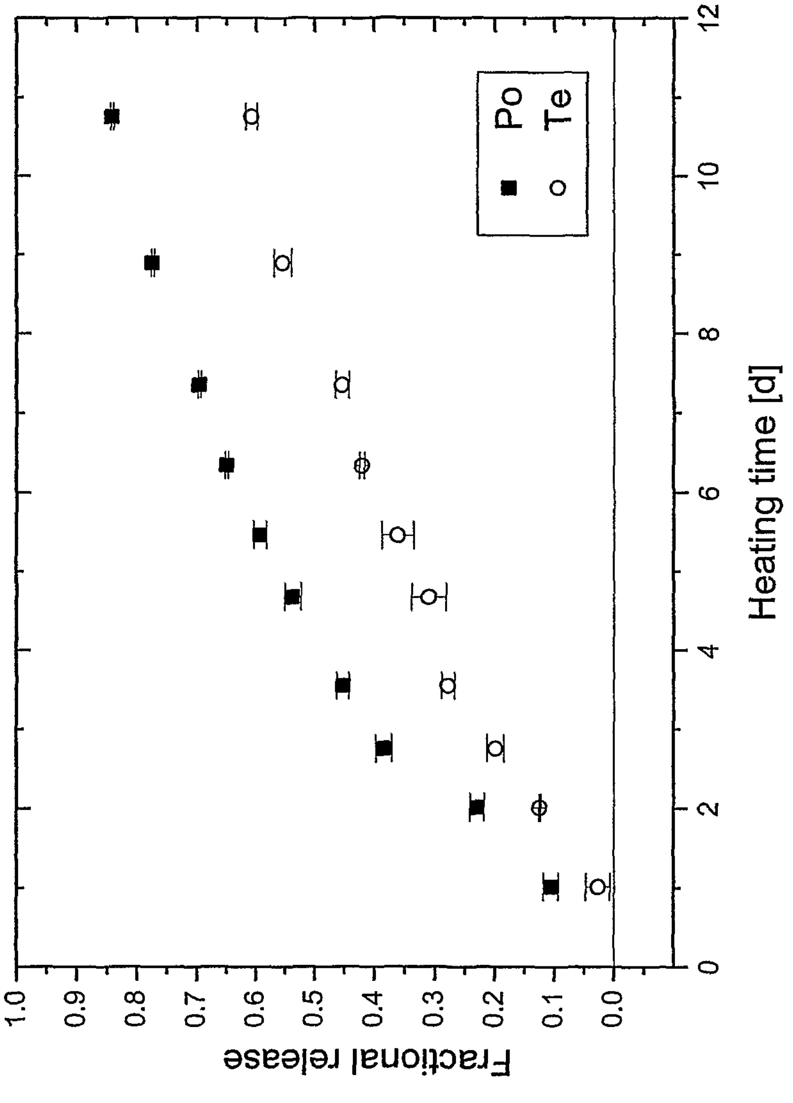

FIG. 6: Comparison of the long-term tellurium and polonium release from LBE in an Ar/7%-$H_2$ atmosphere at 968 K as a function of heating time.

Figure 7:
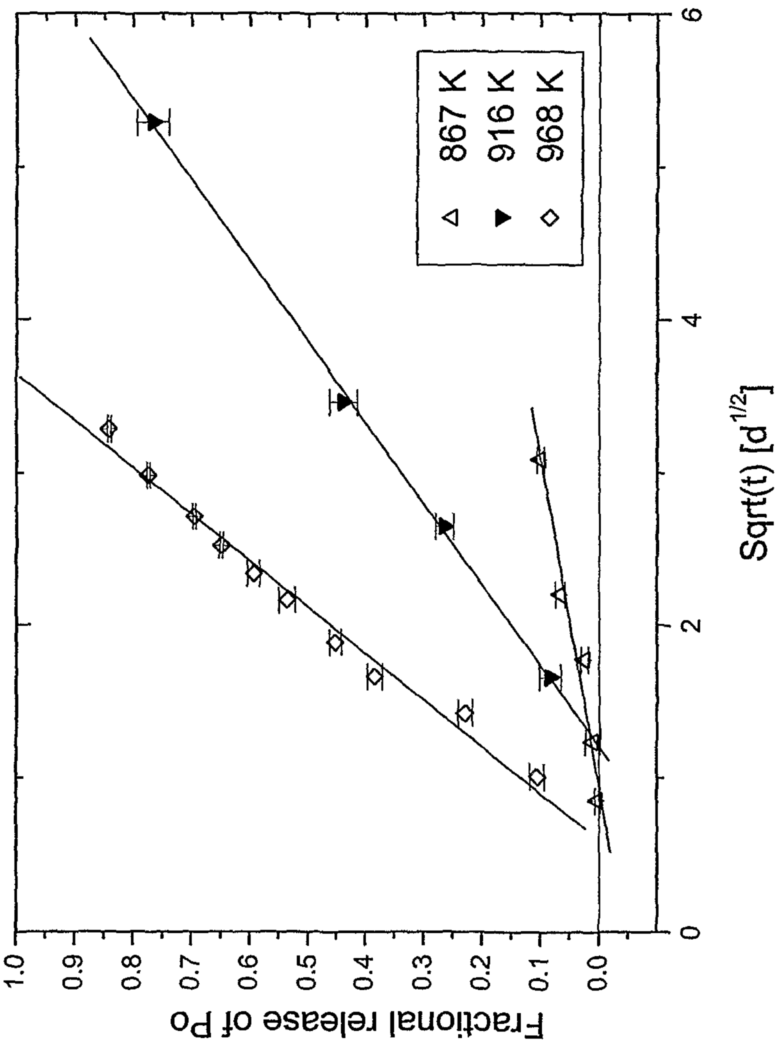

FIG. 7: Approximate linear relationship of polonium release at different temperatures and the square root of heating time.

Figure 8:
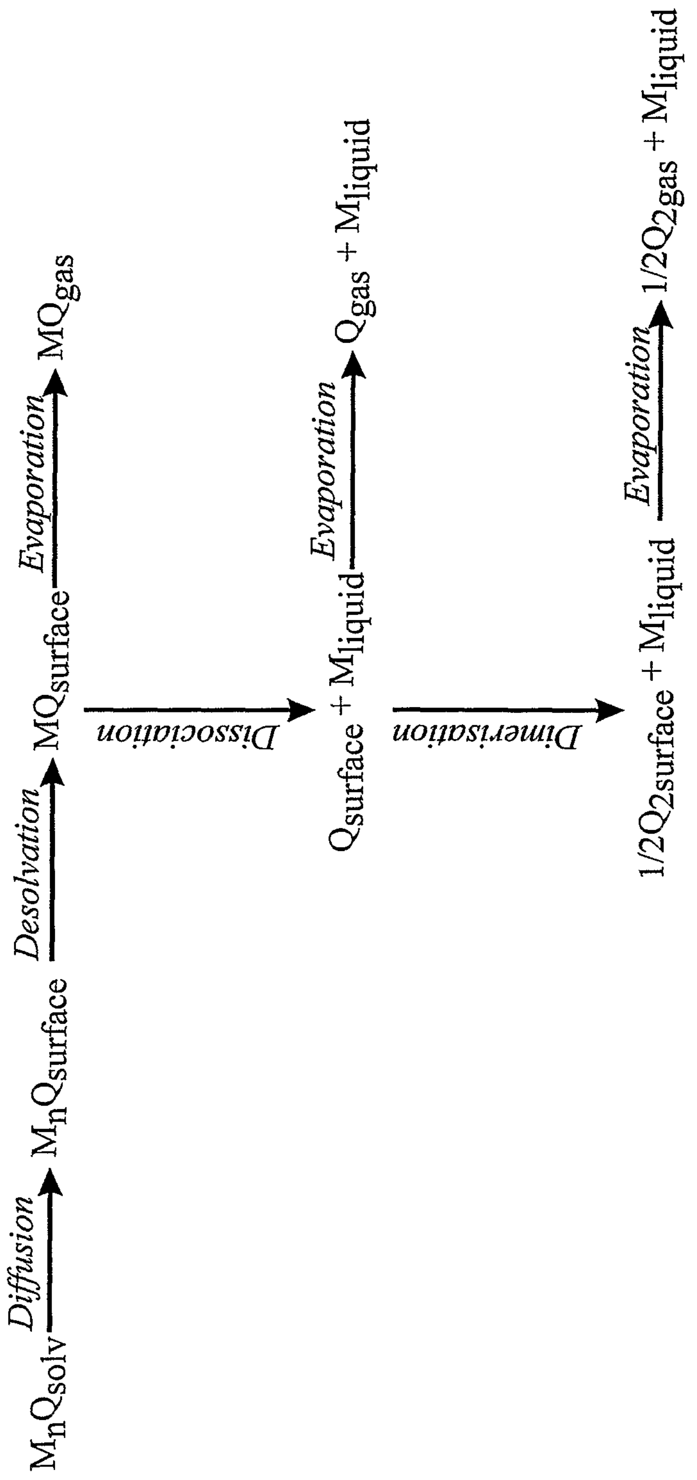

FIG. 8: Scheme of possible reaction steps involved in the release of chalcogens from LBE.

Figure 9:
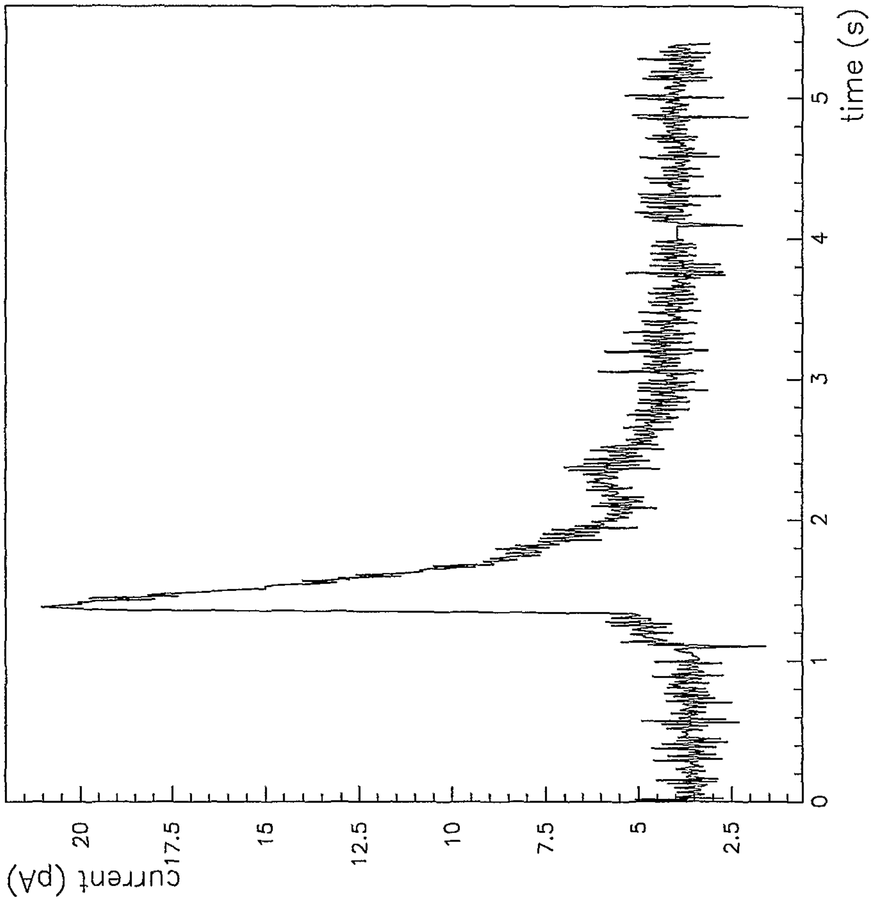

FIG. 9: Current of $^{4}$He (in pA) measured by the Faraday cup.

Figure 10:
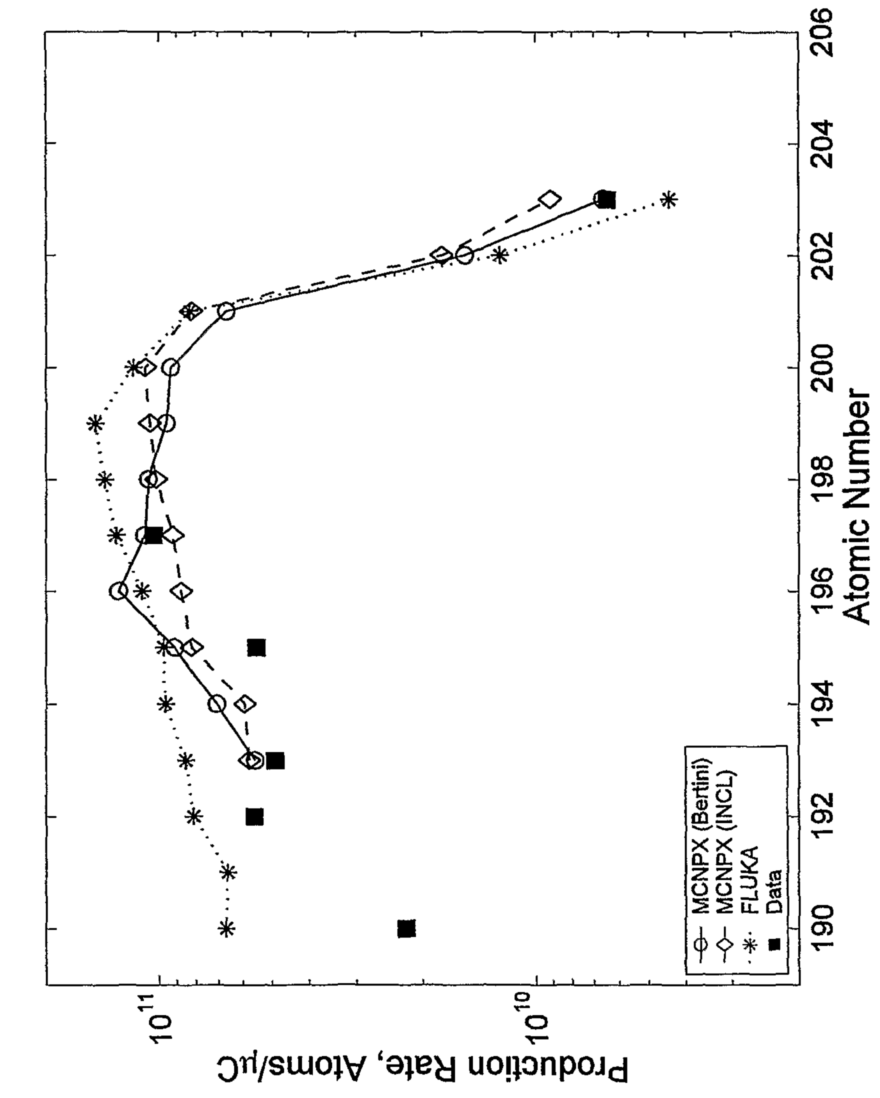

FIG. 10: Production rates for Hg isotopes. Measured points (black squares) are compared with calculations: open circles: MCNPX (Bertini/Dresner model combination); diamonds: MCNPX (INCL4/ABLA); stars: FLUKA.

Figure 11:
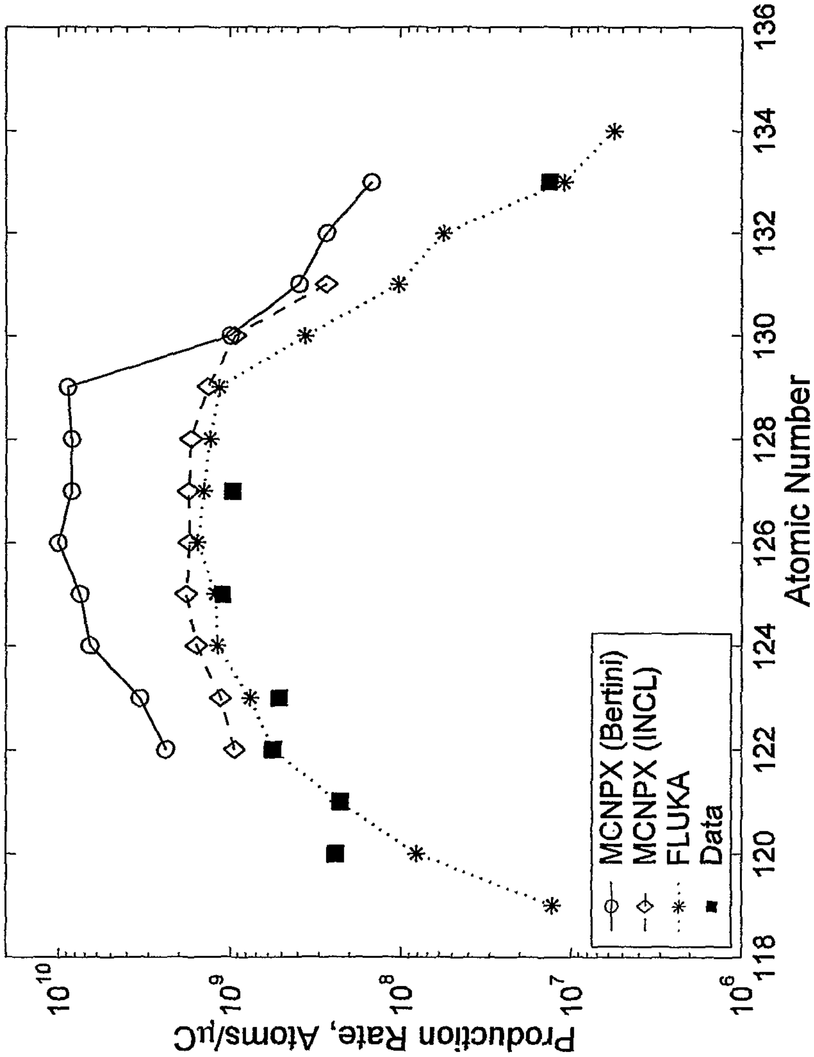

FIG. 11: Production rates for Xe isotopes. Measured points (black squares) are compared with calculations: open circles: MCNPX (Bertini/Dresner model combination); diamonds: MCNPX (INCL4/ABLA); stars: FLUKA.

Figure 12:
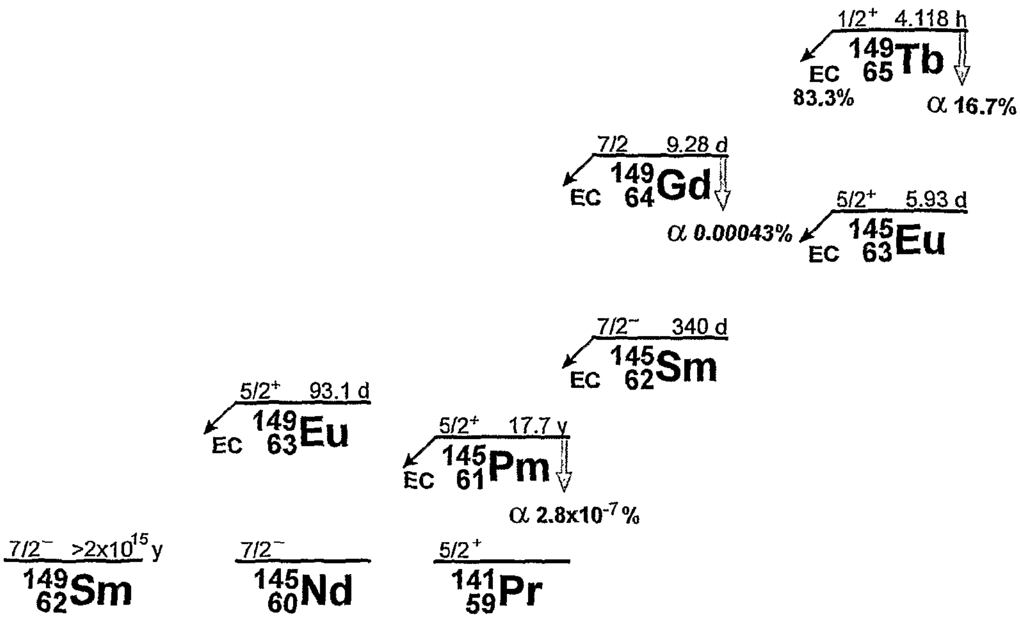

FIG. 12: Simplified decay scheme of $^{149}$Tb and the list of the most relevant gamma-transitions (adopted from [Firestone R B. Table of Isotopes. Eight Edition, New York: Wiley-Interscience, 1996]). Note, the decay of the $^{149}$Tb itself as well as the first daughter products is accompanied with relatively intense gamma emission, while the longer-lived daughter products of the second and third generation show very little gamma contributions.

Figure 13:
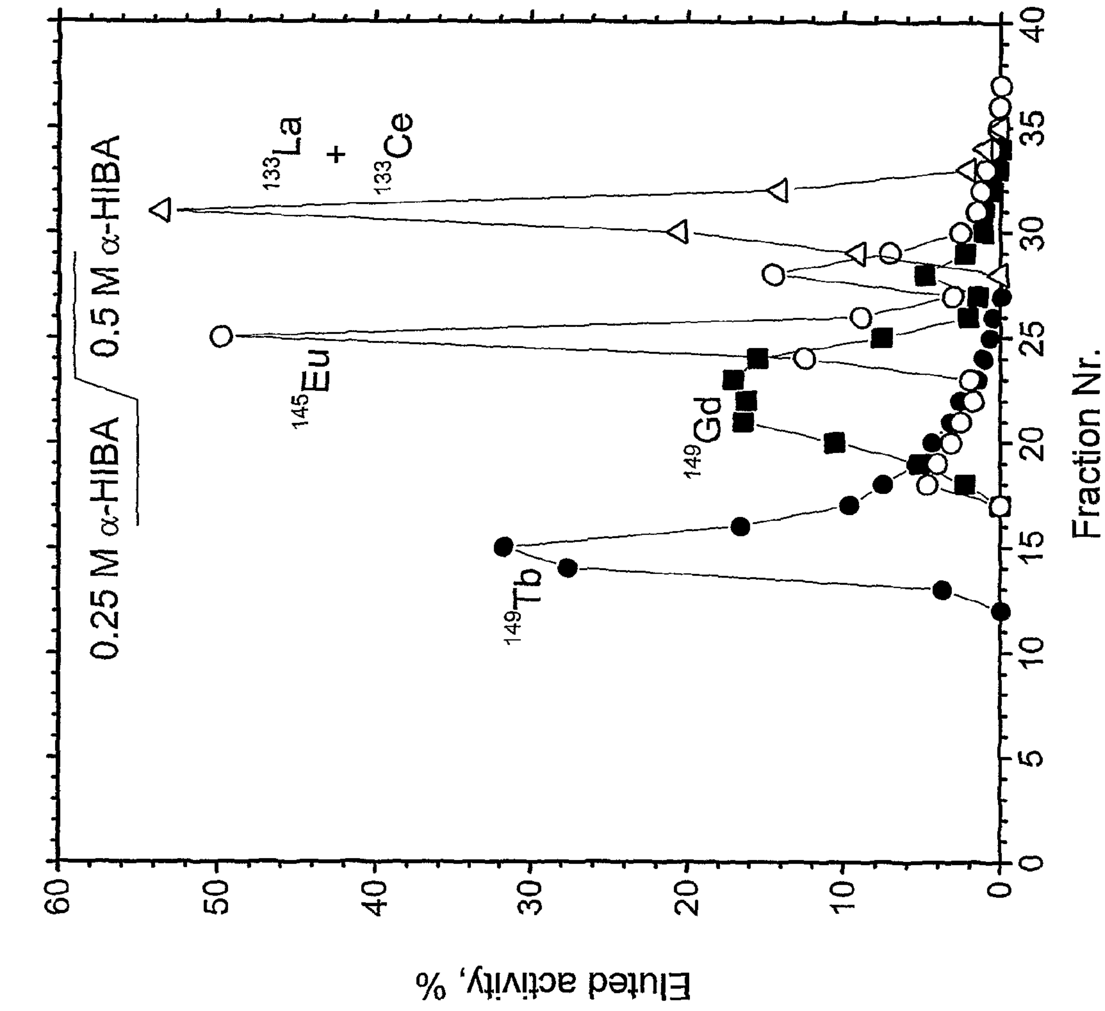

FIG. 13: Separation of the A=149 isobars obtained in the on line isotope separation process at ISOLDE by using cation exchange chromatography. Column: Aminex A 5 in $NH_4^+$-form, 3×60 mm$^2$, eluent: α-HIBA, elution speed: 100 μl/min, (one drop=35 μl=one fraction). The isotopic content of each fraction has been determined by high-resolution gamma ray-spectrometry.

Figure 14:
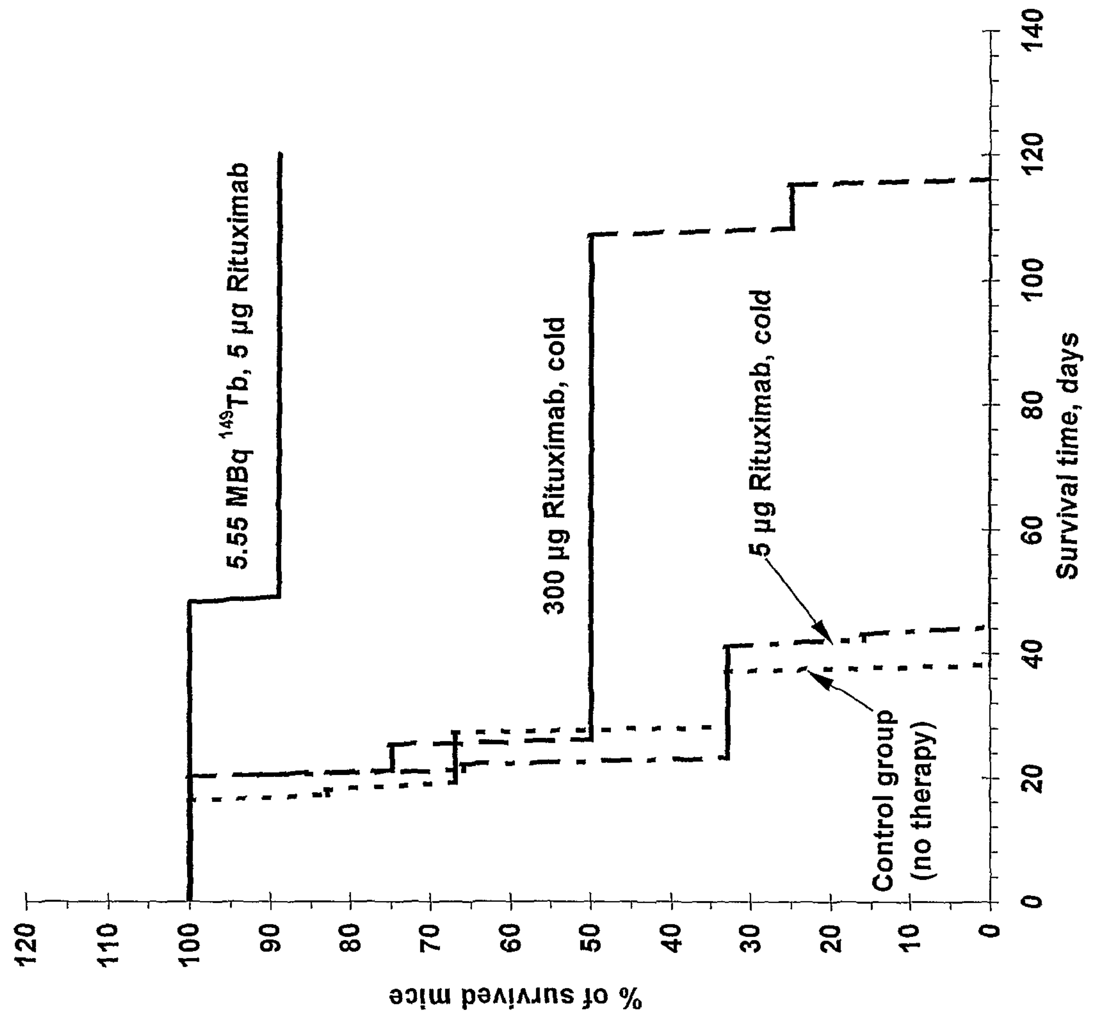

FIG. 14: Survival graph of SCID mice grafted with $5 \cdot 10^6$ Daudi cells i.v., followed by different i.v. treatments two days after xenotransplantation (for details see third preferred aspect and Example 3)

FIG. 15:

a Dissected mouse from the control group with clearly visible large tumor in the abdomen (indicated by arrow);

b Dissected mouse grafted with Daudi cells and treated by $^{149}$Tb-CHX-A-DTPA-Rituximab after 120 days, without any visible signs of a disease.

Figure 16:
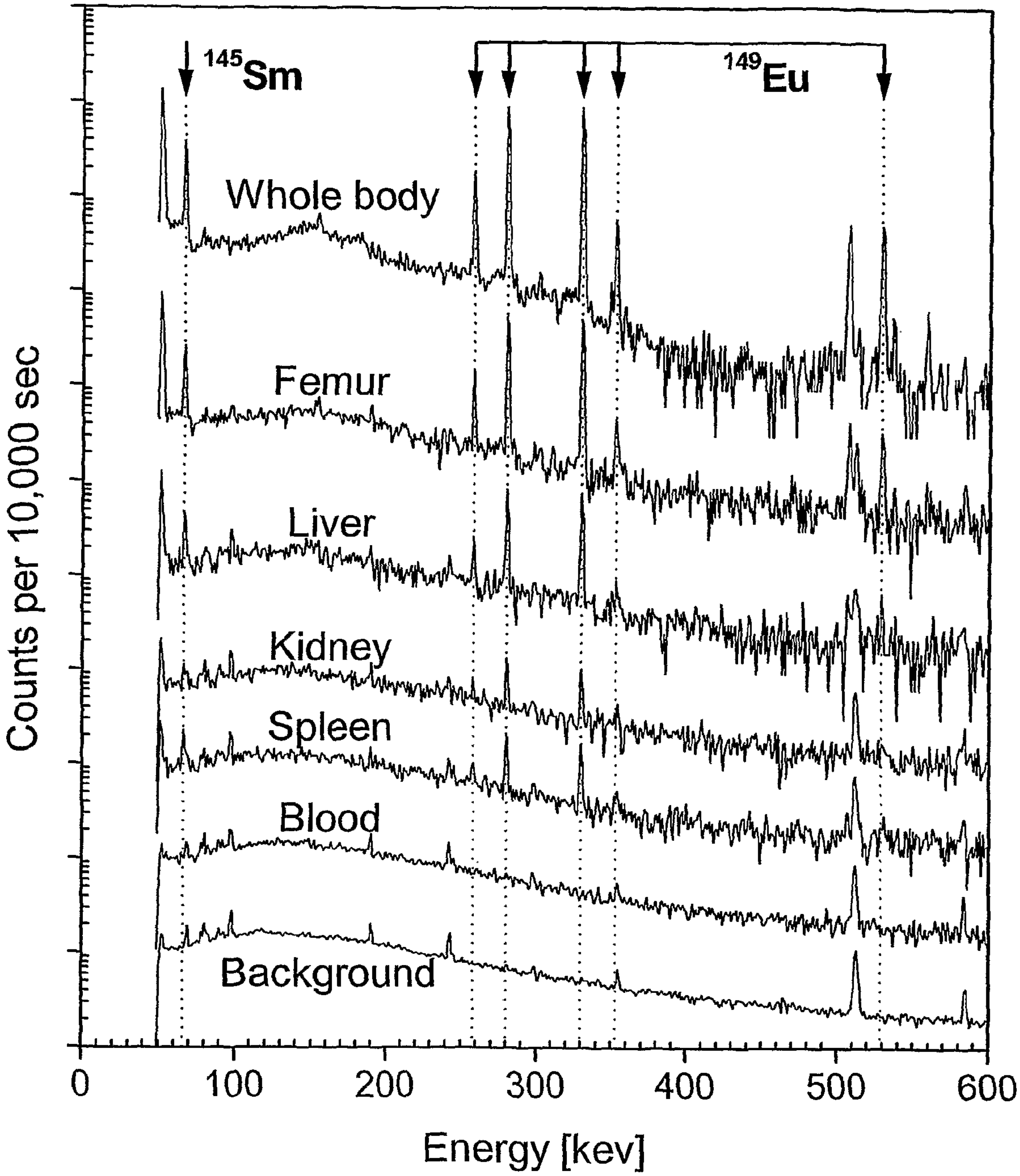

FIG. 16: Typical γ-spectra of retained daughter radioactivity in organs taken 120 days after injecting the radioimmunoconjugate into the mice.

PREFERRED EMBODIMENTS OF THE INVENTION

The following embodiments utilize the previously defined unit operations of the method of the present invention, i.e. preferred combinations, selections, sequences and/or optimizations thereof. However, the person of skill in the art will be able to define und utilize other suitable combinations, selections, sequences and/or optimizations of these unit operations depending on the desired radioisotope(s) to be produced.

For better understanding, the respective utilized unit operations are marked in brackets, e.g. {unit 1}.

Embodiment I

On- or Off-Line Extraction of Radioisotopes from a High Power Liquid Metal Target 1. Application:

High power liquid metal targets are presently being built, planned or proposed for a series of facilities: spallation neutron sources, ADS (accelerator driven systems), as neutron converter for high power ISOL facilities, as meson production target for "superbeams", neutrino factories or muon collider. As a by-product, in the liquid metal target large amounts of radioisotopes are produced by spallation, fragmentation and high energy fission. Generally this radioactivity production is rather considered as a problem since the buildup to a high radioactivity inventory poses tight constraints on the safety of the facility. The inventors provide here a series of methods to continuously extract a good fraction of the produced activity. This serves two purposes: a reduction of the radioactive inventory in the hot target area and the liquid metal loop as a safety measure, and an exploitation of the retrieved radioisotopes for life sciences.

Figure 1A:
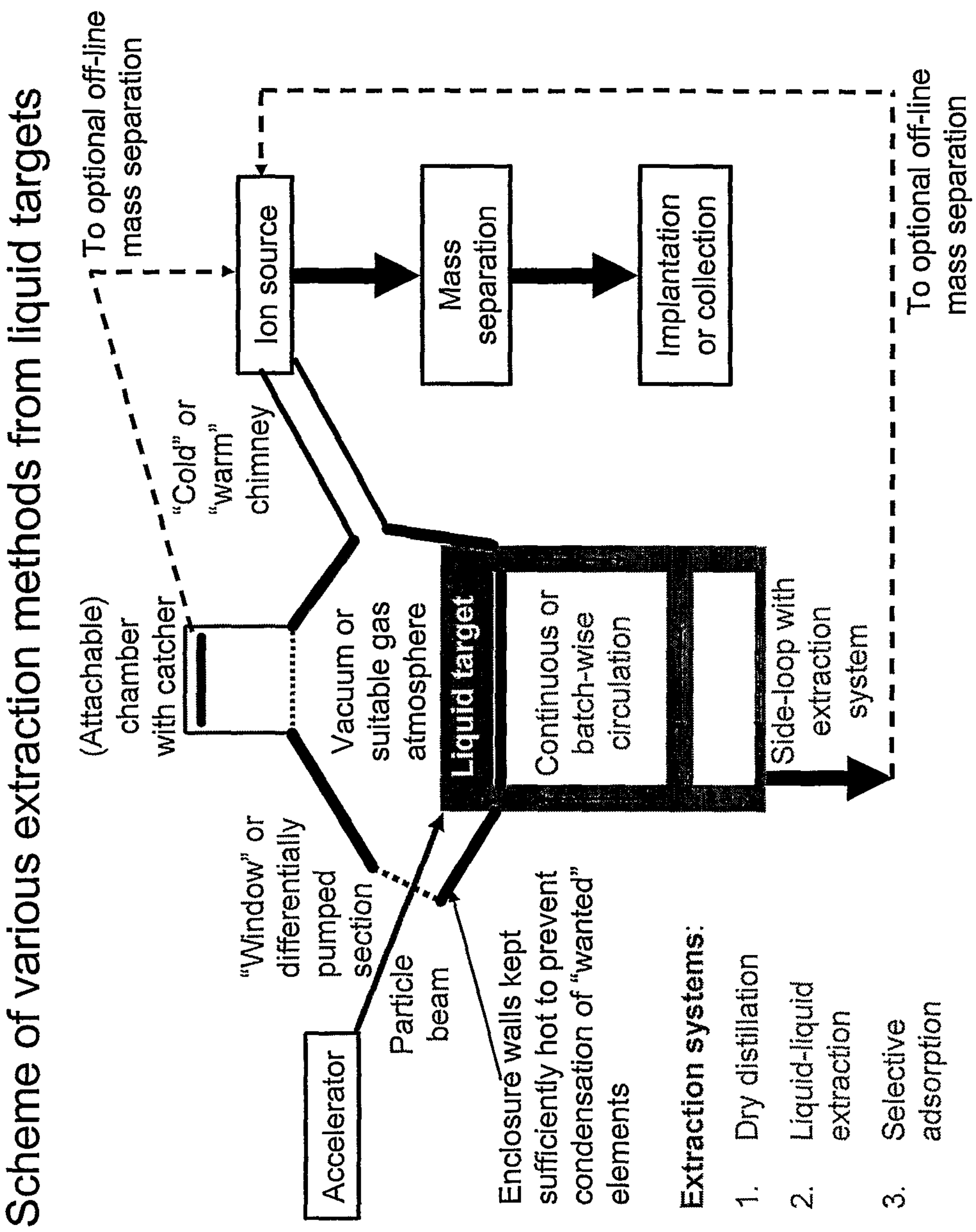
FIGS. 1A and 1B illustrate the different ways to extract radioisotopes from a liquid metal target, either continuously (A) or batch-wise (B).
Figure 1B:
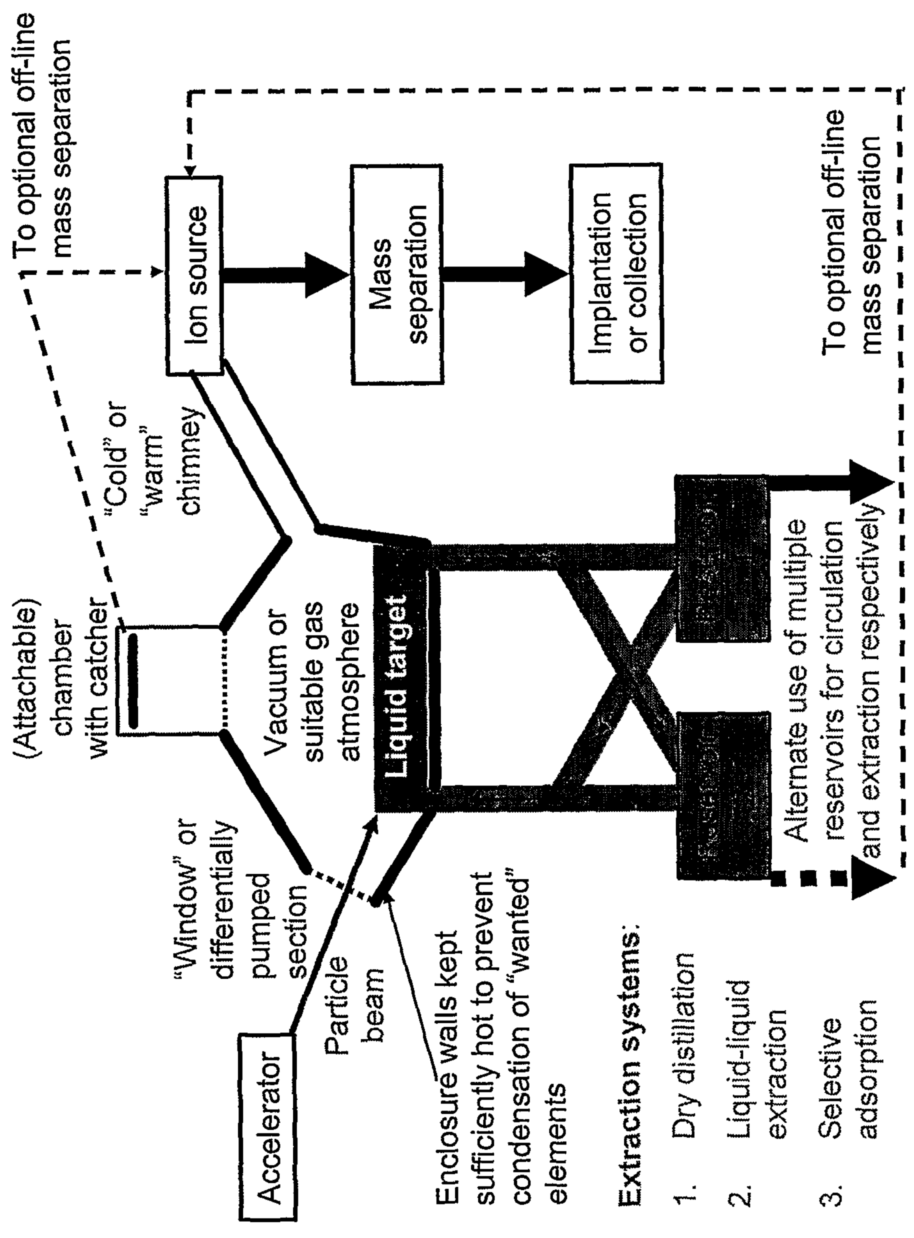

FIGS. 1A and 1B illustrate the different ways to extract radioisotopes from a liquid metal target, either continuously (FIG. 1A) or batch-wise (FIG. 1B). The detailed steps are discussed in the following.

2. Method:

A molten metal target (Hg, Pb, Bi or alloys containing at least one of these elements) is irradiated with high energy particles of >100 MeV energy {unit 1}. With an intermediate energy of few 100 MeV mainly close spallation products (evaporation of 10-30 nucleons) as well as little fission and fragmentation products are generated. With increasing energy of the incident beam (around 1 GeV and above) also deep spallation products (evaporation of 30-60 nucleons) and more fission and fragmentation products are generated. Hence nearly all radioisotopes ranging from $^3$H up to two elements beyond the target element are generated and can be extracted.

Depending on the chemical nature of the elements to be extracted, different variants have to be applied for the extraction:

A. Noble Gases

Noble gases will diffuse to the surface of the liquid target material {unit 2} and be released from it into the target enclosure. The effusing {unit 3} radioisotopes can then be transported by vacuum diffusion or by a flow of inert gas (He, Ar, . . . ) {unit 7} to a plasma ion source where they are ionized {unit 11}. The ions are extracted from the ion source, accelerated to typically several tens of keV {unit 12} and separated in a magnetic sector field according to the mass/charge ratio {unit 13}. The ions are implanted into e.g. a metallic catcher {unit 14}. Alternatively the ions are directly implanted into nanoparticles, etc. {unit 14} for labelling of the latter. For purification, a cold trap can be placed between the target and ion source to retain elements and molecules, which are less volatile than the noble gases of interest.

Thus, method A utilizes a combination of units 1, 2, 3, 7, 11, 12, 13 and 14.

B. Halogens, Mercury, Thallium

{units 1 and 2 as in A}

The halogens and mercury are relatively volatile and are released {unit 3} at the typical operation temperature of targets made from Pb, Bi or alloys containing these elements, e.g. Pb/Bi (this method is not applicable for Hg targets which are operated at lower temperatures). At an enhanced temperature (>600° C.) also thallium is released. These elements will adsorb easily on the walls of the target enclosure if the latter are kept at room temperature. The inventors provide therefore to heat the walls of the target enclosure, and insert a dedicated catcher, which is held at lower temperature {unit 8}. In case of combination with the on-line extraction of noble gases for mass separation, the cold trap will act as catcher for halogens, Hg and Tl.

Thus, method B utilizes a combination of units 1, 2, 3 and 8.

Variant with on-line mass separation: The effusing {unit 3} radioisotopes of halogens, Hg and optionally Tl can be transported {unit 7} together with the noble gases by vacuum diffusion or by a flow of inert gas (He, Ar, . . . ) to an ion source where they are ionized {unit 11}. The ions are extracted from the ion source, accelerated to typically several tens of keV {unit 12} and separated in a magnetic sector field according to the mass/charge ratio {unit 13}. The ions are implanted into e.g. a metallic catcher {unit 14}. Alternatively the ions are directly implanted into nanoparticles, etc. {unit 14} for labelling of the latter.

Thus, this variant of method B utilizes a combination of units 1, 2, 3, 7, 11, 12, 13 and 14.

C. Elements with Lower Volatility than the Target Elements

{units 1 and 2 as in A}

Part of the liquid target material is removed from the area where the beam interacts with it. If the target material is circulated, this can be done e.g. continuously via a side loop. This will help to harvest some radioisotopes, but will not contribute much to a reduction of the overall radioactive inventory in the target area. Therefore, the system is instead made to operate in a push-pull-mode between two batches of liquid target material. While the second batch has come in operation, the first one is available for extraction of the interesting nuclei or for general reduction of its inventory. The recovery of the wanted species can be done in one of the following non-destructive ways that leave the Hg intact and ready for immediate reuse:

1) Dry Distillation {Unit 4}

The target material is removed by evaporation under vacuum or inert atmosphere leaving the less volatile elements in the residue. The wanted nuclei can be recovered from the residue with a variety of methods depending on the element.

2) Liquid-Liquid Extraction

Liquid Hg can be mixed with a suitable solvent, e.g. citric acid. Shaking the mixture for a certain time, e.g. half an hour, allows to transfer a good fraction of the radiolanthanides (valence 3 elements) to the solvent. The solvent is easily separated from the mercury, which will due to its high density and surface tension rapidly coagulate at the bottom of the recipient.

3) Harvesting by Selective Adsorption {Unit 5}

The liquid target metal can be brought in contact with a surface which strongly adsorbs the lanthanides and transition metals that are known to have the lowest solubility, at least in Hg. This can be stable impurities added or dissolved from the steel plumbing like Ni, Mn and Cr that segregate out as oxides floating on the surface of Hg. They act as scavengers for the radioisotopes of the other transition metals and the rare earths so that they can be recovered by simple wiping them of the Hg surface.

In all cases the solvent or residue containing the radioisotopes is either used as stock solution for any conventional radiochemical separation method or evaporated to dryness {unit 8} and inserted into an oven {unit 10} connected to an ion source (surface, laser or plasma ionization). The oven is heated to allow the radioisotopes effuse to the ion source {unit 11} where they are ionized. The ions are extracted from the ion source, accelerated to typically several tens of keV {unit 12} and separated in a magnetic sector field according to the mass/charge ratio {unit 13}. The ions are implanted into e.g. a suitable catcher {unit 14} that facilitates the labeling of the radiopharmaceutical. Alternatively the ions are directly implanted into nanoparticles, etc. {unit 14} for labelling of the latter.

Thus, method C utilizes a combination of units 1, 2, (4 or 5), 8, 10, 11, 12, 13 and 14.

Particular Advantages Include:

The inventors describe for the first time the details of implementation of an extraction plant for radioactive isotopes from irradiated liquid metal targets. The inventors provide for each class of elements the preferred method of extraction. The inventors have performed a demonstration for the on-line production of mass-separated noble gas beams from a Pb target as well as from a Pb/Bi target irradiated with 1.4 GeV protons ("proof-of-principle"). The inventors have performed a demonstration of the on-line production of mass-separated mercury isotopes from a Pb/Bi target irradiated with 1.4 GeV protons ("proof-of-principle"). Particularly strong undissociable bonds to nanoparticles can be obtained by the ion-implantation labelling. The continuous, automated production without manual operation steps ideally suited for industrial production is demonstrated. The inventors provide this method to keep the radioactive inventory in the target area and the liquid metal loop small, an important factor in the safety of high power facilities. The inventors provide a new, simple way to obtain a $^{62}Zn/^{62}Cu$ generator.

In summary, the methods provided within this embodiment comprise the following features:

This universal method works basically for all radionuclides between $^{3}H$ and two elements beyond the target element. In particular the following radionuclides have dedicated relevance: $^{28}Mg$, $^{26}Al$, $^{32}Si$, $^{32}P$, $^{33}P$, $^{42}Ar$, $^{42}K$, $^{43}K$, $^{45}Ca$, $^{47}Ca$, $^{44}Sc$, $^{44m}Sc$, $^{46}Sc$, $^{47}Sc$, $^{44}Ti$, $^{52}Mn$, $^{54}Mn$, $^{56}Mn$, $^{52}Fe$, $^{55}Fe$, $^{59}Fe$, $^{55}Co$, $^{56}Co$, $^{62}Cu$, $^{64}Cu$, $^{67}Cu$, $^{62}Zn$, $^{68}Ga$, $^{68}Ge$, $^{72}As$, $^{72}Se$, $^{73}Se$, $^{75}Se$, $^{75}Br$, $^{76}Br$, $^{77}Br$, $^{75}Kr$, $^{76}Kr$, $^{77}Kr$, $^{81}Rb$, $^{82}Rb$, $^{82}Sr$, $^{83}Sr$, $^{85}Sr$, $^{89}Sr$, $^{85}Y$, $^{86}Y$, $^{87}Y$, $^{88}Y$, $^{89}Zr$, $^{90}Nb$, $^{97}Ru$, $^{103}Pd$, $^{103}Cd$, $^{111}Ag$, $^{113}Sn$, $^{117m}Sn$, $^{119}Sb$, $^{121m}Te$, $^{121}I$, $^{122}I$, $^{123}I$, $^{124}I$, $^{125}I$, $^{126}I$, $^{130}I$, $^{121}Xe$, $^{122}Xe$, $^{123}Xe$, $^{125}Xe$, $^{127}Xe$, $^{129m}Xe$, $^{131m}Xe$, $^{131m,g}Xe$, $^{134}Ce/La$, $^{137}Ce$, $^{139}Ce$, $^{141}Ce$, $^{143}Pr$, $^{138}N/Pr$, $^{140}Nd/Pr$, $^{147}Nd$, $^{149}Pm$, $^{142}Sm/Pm$, $^{153}Sm$, $^{155}Eu$, $^{147}Gd$, $^{148}Gd$, $^{149}Gd$, $^{149}Tb$, $^{152}Tb$, $^{155}Tb$, $^{161}Tb$, $^{157}Dy$, $^{159}Dy$, $^{166}Ho$, $^{165}Er$, $^{169}Er$, $^{165}Tm$, $^{167}Tm$, $^{169}Yb$, $^{177}Yb$, $^{172}Lu$, $^{177}Lu$, $^{172}Hf$, $^{175}Hf$, $^{178}Ta$, $^{178}W$, $^{188}W$, $^{186}Re$, $^{188}Re$, $^{192}Ir$, $^{195}Au$, $^{198}Au$, $^{194}Hg$, $^{194}Hg$, $^{197}Hg$, $^{201}Tl$, $^{202}Tl$, and $^{202}Tl$.

A liquid metal target made from pure Hg, Pb, Bi or an alloy containing at least one of these elements is used.

For producing the elements Ba and lighter additionally to the target materials mentioned above a liquid target made from pure lanthanides or an alloy containing at least one lanthanide element can be used.

For producing the elements Sb and lighter additionally to the target materials mentioned above a liquid target made from pure tins or an alloy containing tin can be used.

For producing the elements As and lighter additionally to the target materials mentioned above a liquid target made from pure germanium or an alloy containing germanium can be used.

Of particular interest here is the possibility to separate a pure $^{62}Zn$ beam, which can be implanted into a suitable matrix and serve as generator for the daughter isotope $^{62}Cu$.

Since there are no other long-lived zinc isotopes decaying to radioactive copper isotopes, such a generator can even be produced without ionization and mass separation, by just catching the zinc fraction released from a liquid germanium target kept at a suitable temperature (>1000° C.). After few hours most of the short-lived zinc isotopes (mainly $^{63}Zn$) have decayed and from now for the next 1-2 days a $^{62}Cu/^{65}Cu$ mixture with >10% $^{62}Cu$ content is obtained by extracting repeatedly the Cu fraction by conventional radiochemical separation methods.

During irradiation the target is kept above the melting point. The temperature is controlled by heating/cooling the target vessel and/or heating/cooling the target material when the latter is flowing in a circuit.

The liquid target material can be standing as a bath in a container, be a free-standing jet or a flow enclosed on one or more sides by a wall.

The incident beam with >100 MeV energy is provided by a particle accelerator (cyclotron, LINAC, synchrotron, etc.).

The incident proton beam can be replaced by energetic light ions (d, $^{3}He$, $^{4}He$, . . . ), heavy ions, neutrons, electrons or photons.

The proton beam can enter the target enclosure via a window or via a differentially pumped section.

The target material can be kept in motion by pumping, mechanical shaking, electromagnetic agitation, etc. to assure a better temperature homogeneity and thus allow for higher beam currents without the risk of local overheating.

A chimney or baffles can be used to condense evaporating target material before it reaches the catcher or ion source.

The radioisotopes will diffuse to the surface of the liquid target material.

Radioisotopes of elements with higher volatility than the target material can be released from the target surface into the target enclosure.

The effusing radioisotopes can then be transported by vacuum diffusion or by a flow of inert gas (He, Ar, . . . ) to an ion source where they are ionized.

The target is connected to the ion source in a way that no other escape path is available for the radioisotopes.

Optionally the flow of effusing volatile radioisotopes can be directed towards the ion source with a turbomolecular pump.

The entire target enclosure and all surfaces which the released radioisotopes can encounter, except the catcher, is kept at a sufficiently high temperature to avoid a condensation of halogens, mercury and thallium at places other than the catcher.

The ions are extracted from the ion source, accelerated to typically several tens of keV and separated in a magnetic sector field according to the mass/charge ratio.

The ions are implanted into e.g. a metallic catcher.

Alternatively the ions are directly implanted into nanoparticles, etc. for labelling of the latter. For purification, a cold trap can be placed between the target and ion source to retain elements and molecules, which are less volatile than the noble gases of interest.

Radioisotopes can be extracted on-line without disturbing the target irradiation if part of the liquid target material is removed from the area where the beam interacts with it.

If the target material is circulated, this can be done e.g. continuously via a side loop.

To reduce the overall radioactive inventory in the target area, the system can be made to operate in a push-pull-mode between two batches of liquid target material. While the second batch has come in operation, the first one is available for extraction of the interesting nuclei or for general reduction of its inventory.

The recovery of the wanted species can be done in one of the following non-destructive ways that leave the Hg intact and ready for immediate reuse:

A) Dry distillation: The target material is removed by evaporation under vacuum or inert atmosphere leaving the less volatile elements in the residue. The wanted nuclei can be recovered from the residue with a variety of methods depending on the element.

B) Liquid-liquid extraction: Liquid Hg can be mixed with a suitable solvent, e.g. citric acid. Shaking the mixture for a certain time, e.g. half an hour, allows to transfer a good fraction of the radiolanthanides (valence 3 elements) to the solvent. The solvent is easily separated from the mercury, which will due to its high density and surface tension rapidly coagulate at the bottom of the recipient.

C) Harvesting by selective adsorption: The liquid target metal can be brought in contact with a surface which strongly adsorbs the lanthanides and transition metals that are known to have the lowest solubility, at least in Hg. This can be stable impurities added or dissolved from the steel plumbing like Ni, Mn and Cr that segregate out as oxides floating on the surface of Hg. They act as scavengers for the radioisotopes of the other transition metals and the rare earths so that they can be recovered by simple wiping them of the Hg surface.

In all cases (A, B or C) the solvent or residue containing the radioisotopes is either used as stock solution for any conventional radiochemical separation method or evaporated to dryness and inserted into an oven connected to an ion source (surface, laser or plasma ionization).

The oven is heated. The effusing radioisotopes can then be transported by vacuum diffusion or by a flow of inert gas (He, Ar, . . . ) to an ion source where they are ionized.

The oven is connected to the ion source in a way that no other escape path is available for the radioisotopes.

The inert gas can be replaced by any other gas if the latter is compatible with the integrity of the target, the enclosure and the catcher surface.

Several chambers with catchers can be attached to the target chamber and connected/disconnected from the latter without interruption of the irradiation for a significant time.

Variant: instead of on-line separation, the irradiation can be performed at a reduced target temperature. The target is then heated afterwards when needed to release the elements of interest.

The target, oven, walls, ion source, etc. are heated by any suitable mean (Ohmic heating, electron bombardment, radiofrequency, infrared heating, laser heating, energy loss of the incident beam, etc.) or any combination of these methods.

The effusing radioisotopes can be transported by a flow of inert gas (He, Ar, . . . ) to the ion source instead of being transported by vacuum diffusion.

The mass separation can be performed with any mass-selective device, e.g. a Wien-filter, a radio-frequency quadrupole, etc. instead of the magnetic sector field.

Often several isotopes of the same element, or isobars with comparable masses are produced in the same system. In this case a mass-selective device is of advantage, which allows to collect simultaneously several masses.

The mass-separated ion beam is implanted into a salt layer.

The salt layer containing the radioisotopes is subsequently dissolved in a small volume of water or the eluting agent.

The salt cover of the backings can be replaced by many other water-soluble substances (sugar, . . . ) or by a thin ice layer (frozen water or other liquid). Instead of dissolving, the latter is subsequently melted by heating with any suitable method (Ohmic heating, infrared heating, radio-frequency heating, . . . ).

Instead of a soluble matrix, the ion beam can also be implanted into any other solid matrix, e.g. a metal foil. In this case one needs additionally a chemical separation of the desired isotope from the matrix material that usually disturbs the chromatographic process.

In all cases (i.e. elution from the catcher, dissolving of salt, etc. layer, melting of ice layer) the product fraction is usually obtained in a small volume and can be directly used for the labelling procedure of bio-conjugates or be directly injected into a chromatographic system for further purification.

A particularly simple separation that allows to obtain many of the described elements in gaseous form can be achieved by thermal release from a refractory matrix.

Any of the classical radio-chemical and radio-chromatographical processes (precipitation, electrochemical separations, extraction, cation exchange chromatography, anion exchange chromatography, extraction chromatography, thermo chromatography, gas chromatography, etc.) suitable for the separation of astatine can be applied for the separation of the desired product from isobars and pseudo-isobars (stemming from molecular sidebands like oxides or fluorides appearing at the same mass settings), from daughter products generated by the radioactive decay of the collected radioisotopes during collection and processing and from other impurities.

Ligands used for the chemical separation process are eventually remaining with the product fraction and need to be eliminated before further labelling procedures. Evaporation is the most suitable way for many cases.

Nano- or micro-particles, macro-molecules, microspheres, macro-aggregates, ion exchange resins or other matrices used in chromatographic systems can be labelled directly by implanting the radioactive ion beam into them. For cases where the radioisotopic purity is already sufficient or for implantation into ion exchange resins or other matrices used in chromatographic systems, this can be done directly on-line. Else, after the standard purification steps (radio-chromatographic separation of isobars) the product is again injected into an ion source, ionized, accelerated and implanted.

The so obtained products are carrier-free and isotopically pure.

The process can be operated with all the technological steps of the chain as described. However, one can reduce freely the number of steps in many cases to adapt to the required purity of the respective application.

The inventors provide the separation of the noble gas isotopes $^{75,76,77}$Kr as a new production method of their respective decay daughters $^{75,76,77}$Br.

The inventors provide the separation of the noble gas isotopes $^{121,122,123,125}$Xe as a new production method of their respective decay daughters $^{121,122,123,125}$I.

Embodiment II

Production of Radioisotopes Relevant for Targeted Alpha Therapy (TAT) Via Continuous or Batch-Mode Extraction from Actinide Targets 1. Application:

The alpha emitters $^{212}$Bi, $^{213}$Bi, $^{223}$Ra, $^{224}$Ra and $^{225}$Ac and the in vivo generator isotope Pb are promising candidates for targeted alpha therapy.

2. Method:

The inventors provide the following new methods:

A. Spallation production of $^{225}$Ac

A target made from metallic $^{232}$Th or a compound or alloy containing $^{232}$Th is irradiated by high energy (>50 MeV) particles {unit 1}. Alternatively a target made from natural uranium or $^{238}$U partially or fully depleted in $^{235}$U or a compound or alloy containing these isotopes is irradiated by high energy (>80 MeV) particles {unit 1}. $^{225}$Ac is produced by the spallation reaction $^{232}$Th(p,2p6n) or $^{238}$U(p,4p10n) respectively. After a suitable cooling period to let short-lived isotopes decay, Ac is separated from the target and the mixture of spallation and fission products by a conventional radiochemical separation method. The resulting Ac fraction contains a mixture of $^{225}$Ac and $^{227}$Ac with an activity ratio of the order of 100 to 1000 in favor of $^{225}$Ac. Optionally, the isotopic purity of $^{225}$Ac can be further enhanced by evaporating the Ac fraction to dryness {unit 8} and inserting it into an oven {unit 10} connected to an ion source (surface, laser or plasma ionization) {unit 11}. The oven is heated to allow the radioisotopes effuse {unit 7} to the ion source where they are ionized. The ions are extracted from the ion source, accelerated to typically several tens of keV {unit 12} and separated in a magnetic sector field according to the mass/charge ratio {unit 13}. The ions are implanted into e.g. a suitable catcher {unit 14} that facilitates the labeling of the radiopharmaceutical or directly into a column of a $^{225}$Ac/$^{213}$Bi generator {unit 14} Alternatively the ions are directly implanted into nanoparticles, etc. {unit 14} for labelling of the latter.

$^{227}$Ac can be collected simultaneously and serve as generator for $^{223}$Ra production.

Thus, method A utilizes a combination of units 1, 7, 8, 10, 11, 12, 13 and 14.

B. Spallation Production and Dry, Non-Target-Destructive Extraction of $^{225}$Ac Method A has still the drawback that the target is destroyed during the Ac extraction process and that liquid chemical waste is produced. The following variant omits these problems: A target made from metallic $^{232}$Th or a compound or alloy containing $^{232}$Th is irradiated by high energy (>50 MeV) particles {unit 1}. The Th foils/fibers/spheres/foam/ etc. can be mixed with spacers made from a refractory metal (Ta, W, Re, Ir, . . . ) which maintain the geometric arrangement during heating. The target is heated to sufficiently high temperature (80-100% of the melting temperature) to make Ac diffuse {unit 2} to the surface from where it can desorb {unit 3}. As in method 1, chemical and mass separations {units 10-14} can be used to achieve the desired isotopic purity. The target can be used continuously over longer time or batch-wise (irradiating/extracting/irradiating/ . . . ) for several times.

Thus, method B utilizes a combination of units 1, 2, 3, 10, 11, 12, 13 and 14.

C. Production of Isotopically Pure $^{223,224,225}$Ra Samples

A target made from metallic $^{232}$Th or a compound or alloy containing $^{232}$Th is irradiated by high energy (>50 MeV) particles {unit 1}. Alternatively, a target made from natural uranium or $^{238}$U partially or fully depleted in $^{235}$U or a compound or alloy containing these isotopes is irradiated by high energy (>80 MeV) particles {unit 1}. The isotopes $^{223,224,225}$Ra are produced by the spallation reaction $^{232}$Th(p,3p5-7n) or $^{238}$U(p,5p9-11n) respectively. The target is heated to sufficiently high temperature (70-100% of the melting temperature) to make Ra diffuse to the surface {unit 2} from where it can desorb {unit 3}. Ra desorption is favored {unit 6} by addition of halogens or a volatile halogenated compound. The Ra isotopes are escaping from the target material and transported in vacuum or under gas flow {unit 7} to the ion source {unit 11}, where they are ionised into single positively charged ions using any kind of ionisation principles (surface ionisation, resonant laser ionisation or plasma ionisation). The ions are extracted from the ion source, accelerated to typically several tens of keV {unit 12} and separated in a magnetic sector field according to the mass/charge ratios into isobars {13}. The ions are implanted into e.g. a suitable catcher {unit 14} that facilitates the labeling of the radiopharmaceutical or directly into a column {unit 14} of a $^{224}$Ra/$^{212}$Bi generator or $^{225}$Ra/$^{213}$Bi generator respectively. Alternatively the ions are directly implanted into nanoparticles, etc. {unit 14} for labelling of the latter. After mass separation $^{223}$Ra, $^{224}$Ra and $^{225}$Ra can be collected simultaneously for different applications. Thus, method C utilizes a combination of units 1, 2, 3, 6, 7, 11, 12, 13 and 14.

D. Indirect On-Line Production of Pure $^{212,213}$Bi Samples

In a variant of method C the target and/or ion source is kept at a lower temperature {units 1-3, 7, 11-13 as before}. Thus very pure beams of francium isotopes can be produced. The mass-separated $^{220}$Fr beam is collected {unit 14} and decays to a pure $^{212}$Bi sample. Simultaneously the mass-separated $^{221}$Fr beam can be collected {unit 14}, which decays to a pure $^{213}$Bi sample. Thus, method D utilizes a combination of units 1, 2, 3, 7, 11, 12, 13 and 14.

E. Indirect On-Line Production of Pure $^{212,213}$Bi Samples

In a variant of method C the target is connected via a cold trap to a plasma ion source {units 1-3, 7, 11-13 as before}. Thus very pure beams of radon isotopes can be produced. The mass-separated $^{220}$Rn beam is collected {unit 14} and decays to a pure $^{212}Pb/^{212}Bi$ sample. Simultaneously the mass-separated $^{221}Rn$ beam can be collected {unit 14}, which decays to a pure $^{213}Bi$ sample.

Thus, method E utilizes a combination of units 1, 2, 3, 7, 11, 12, 13 and 14.

A New, Dry $^{225}Ac/^{213}Bi$ generator

Making use of the fact that actinides form rather stable carbides, $^{225}Ac$ can be bound in a graphite matrix. Heating the latter to temperatures around 1400-2000° C., Ac will remain in the matrix, while the decay daughters $^{221}Fr$, $^{217}At$ and $^{213}Bi$ are easily released {units 2,3}. They can be condensed {unit 8} on a cooler surface which acts as catcher of the $^{213}Bi$ product. Instead of a graphite matrix, $^{225}Ac$ can also be adsorbed, implanted or alloyed onto/into a suitable metallic matrix.

A New, Dry $^{228}Th/^{224}Ra$ Generator

Also $^{228}Th$ can be bound in a graphite or metallic matrix. Heating this matrix to temperatures around 1600-2200° C., Th will remain in the matrix, while the decay daughter Ra is released {units 2,3}. It can be condensed {unit 8} on a cooler surface and extracted.

A New, Dry $^{224}Ra/^{212}Pb/^{212}Bi$ Generator $^{224}Ra$ is bound in a porous matrix of e.g. a fatty acid salt, a metal hydroxide or oxide. Emanation of the decay daughter $^{220}Rn$ occurs at room temperature and can be accelerated by heating the matrix {units 2,3}. The emanating $^{220}Rn$ is condensed {unit 8} on a cold surface which acts as catcher of the $^{212}Pb/^{212}Bi$ product or collected electrostatically from the gas phase.

A longer-lived generator can be obtained by replacing the $^{224}Ra$ with $^{228}Th$ or by a combination with the methods 7. and 8. (i.e. the dry $^{228}Th/^{224}Ra$ generator and the dry $^{224}Ra/^{212}Pb/^{212}Bi$ generator), by keeping the 228Th generator at a temperature where 224Ra is not released, but 220Rn emanates.

A New, Dry $^{227}Ac/^{227}Th/^{213}Ra$ Generator $^{225}Ac$ can be bound in a graphite matrix which will also bind the decay daughter $^{227}Th$. Heating the matrix to temperatures around 1600-2000° C., Ac and Th will remain in the matrix, while the decay daughters $^{223}Fr$ and $^{223}Ra$ are easily released {units 2,3}. They can be condensed {unit 8} on a cooler surface which acts as catcher of the $^{223}Ra$ product.

Instead of a graphite matrix, $^{225}Ac$ can also be adsorbed, implanted or alloyed onto/into a suitable metallic matrix.

Particular Advantages Include:

The inventors provide a new general method of $^{225}Ac$ production. The inventor's production methods can start from natural or depleted uranium and natural thorium targets. These are cheaper and easier to handle than the normally necessary $^{226}Ra$, $^{228}Th$, $^{229}Th$, etc. The inventors provide to collect mass-separated Fr or Rn isotopes, which decay then to isotopically pure Bi or Pb samples. The inventors have performed a demonstration for the on-line production of isotopically pure $^{212}Bi$ samples as decay product of mass-separated $^{220}Fr$ ion beams ("proof-of-principle"). The inventors provide new types of dry generators, which avoid wet chemical waste and surpass the activity limitations of conventional ion exchange generators, which are subject to radiation damage. Selecting the implantation energy one can choose freely between a radioactive source, which is "closed" or "open" for the release of daughter recoils. Particularly strong undissociable bonds to nanoparticles can be obtained by the ion-implantation labelling. The continuous, automated production without manual operation steps, ideally suited for industrial production, is demonstrated.

In summary, the methods provided within this embodiment comprise the following features:

This approach works for the isotopes $^{212}Pb$, $^{212}Bi$, $^{213}Bi$, $^{223}Ra$, $^{224}Ra$, $^{225}Ra$ and $^{225}Ac$ which are alpha emitters or decay parents of alpha emitters.

A target made from metallic $^{232}Th$ or a compound or alloy containing $^{232}Th$ is irradiated by medium or high energy (>50 MeV) particles.

A target made from natural uranium or $^{238}U$ partially or fully depleted in $^{235}U$ or a compound or alloy containing these isotopes is irradiated by medium or high energy (>80 MeV) particles.

Some of the target materials can be in form of foils, wires, powder, foam, etc.

The wanted products close the target are produced by spallation by a medium or high energy (>80 MeV) particle beam provided by a particle accelerator (cyclotron, LINAC, synchrotron, etc.).

Combined with conventional radiochemical separation from the target $^{225}Ac$ samples are obtained containing 0.1-1% relative activity $^{227}Ac$.

Non target-destructive extraction of $^{225}Ac$ samples with 0.1-1% $^{227}Ac$ are obtained by dry high-temperature separation of the nuclear reaction products from the target material combined with conventional radio chemistry.

During or after the irradiation the target is kept at a temperature of >1200° C.

The entire target enclosure and all surfaces which the released Ac can encounter, except a catcher, is kept at a sufficiently high temperature to avoid condensation of Ac at places other than the cooled Ac catcher.

This non-destructive batch-mode operation has the advantage that the same target unit can be used many times and the amount of liquid waste is reduced.

Monoisotopic $^{225}Ac$ samples are obtained by removing the $^{227}Ac$ from the purified Ac batch using mass separation.

The mass separation can be performed with any mass-selective device, e.g. a Wien-filter, a radio-frequency quadrupole, etc. instead of the magnetic sector field.

The Ac containing oven for feeding the ion source and ion source are heated by any suitable mean (Ohmic heating, electron bombardment, radio-frequency, infrared heating, laser heating, energy loss of the incident beam, etc.) or any combination of these methods.

The effusing radioisotopes can be transported by a flow of inert gas (He, Ar, . . . ) to the ion source instead of the transport by vacuum diffusion.

The target is connected to the ion source in a way that no other escape path is available for the radioisotopes.

The desorption and transport of Ac to the catcher or the ion source can be accelerated by chemical evaporation, adding a small amount of suitable agent (halogens or volatile halogenated compounds).

Surface or plasma ionisation of Fr, Ra and Ac can be used as well as resonant laser ionisation with laser light generated from dye lasers, Ti:sapphire lasers or any other type of wavelength tunable light sources (OPO, . . . ) which are pumped by solid state lasers (Nd:YAG, Nd:YLF, Nd:YVO, diode, . . . ) or gas lasers (copper vapour lasers, etc.).

The wanted $^{223,224,225}Ra$ isotopes are produced in a continuous on-line or discontinuous but still fully automated method in which the target is connected directly to the ion source of a mass separator.

Pure $^{212}Pb$ and $^{212,213}Bi$ samples too are produced in a continuous on-line fully automated method in which the target is connected directly to the ion source of a mass separator and the ion source type and target temperature are selected and or adjusted to make beams of their Fr or Rn precursors.

The availability of the wanted alpha emitters in ion beam form allows to label nanoparticles, other substrates or chemical compounds that facilitates the labeling of bioconjugates.

By selecting the implantation energy, the implantation depth can be adjusted that alpha-recoils can either be ejected and emanate (implantation energy typically <100 keV leads to a low implantation depth), thus representing an open source, or that alpha-recoils cannot leave the matrix (implantation energy typically >150 keV leads to a deeper implantation depth), hence representing a closed source.

Implantation can be performed through a suitable thin cover layer into the collection matrix. Thus the source can be transported as "closed". The end user can easily remove the cover layer by dissolving, evaporating, burning, mechanically removing, etc. to obtain an open source with well-defined depth profile.

A number of new dry isotope-generators can be made by either incorporating the purified precursor isotopes chemically or directly by ion implantation in a suitable substrate.

New, dry forms of isotope generators $^{228}Th/^{224}Ra$, $^{224}Ra/^{212}Pb/^{212}Bi$, $^{228}Th/^{212}Pb/^{212}Bi$ $^{225}Ac/^{213}Bi$ and $^{227}Ac/^{227}Th/^{223}Ra$ are described. They are all based on the fact that the mother isotope(s) is/are bound in the matrix while the daughter isotopes can emanate at the given temperature and are collected on a suitable catcher.

Embodiment III

On-Line Production of Carrier-Free $^{211}At$ for In Vivo Application

1. Method:

A molten Bi target is irradiated with alpha particles of ca. 28 MeV energy {unit 1}. $^{211}At$ is produced in the $^{209}Bi$(alpha, 2n) reaction (a higher alpha energy would open the $^{209}Bi$ (alpha,3n) channel to the undesired $^{210}At$). The target is kept during irradiation in a temperature range between the melting point (e.g. 271° C. for pure Bi and 183° C. for eutectic Pb/Bi alloy) and <500° C.

Astatine is released {units 2,3} and is transported either under vacuum or in inert gas {unit 7} to a suitable catcher surface {unit 8}, e.g. silver. No polonium is released for temperatures below 500° C.; this prevents a contamination of the final product with $^{210}Po$ which is produced in the given energy range by the $^{209}Bi$(alpha,t) reaction.

The catcher is mounted in a way to be easily changeable once the desired amount of $^{211}At$ has been collected on it.

Thus, here a combination of at least units 1, 2, 3, 7 and 8 is utilized.

Particular Advantages Include:

The inventor's method allows to use or reuse the target for long time. Continuous automated production without manual operation steps ideally suited for large scale industrial application is demonstrated. The frequent (manual) interventions to remove and handle the target are omitted. Since liquid Bi here also functions as an efficient heat transfer medium, the inventor's target is adaptable to any beam current, thus surpassing the intrinsic limitation of the existing technology. Due to the on-line chemical separation the decay losses inherent to the off-line process (during irradiation and separation) are avoided. Hence a larger fraction of the produced $^{211}At$ is extracted. The provided procedure is ideally suited to be integrated into the upcoming dedicated "alpha-emitter-producing-cyclotron-facilities".

In summary, the methods provided within this embodiment comprise the following features:

A pure Bi metallic target or a Bi containing alloy is used as target.

During irradiation the target is kept in a temperature range between the melting point and ca. 500° C. The temperature is controlled by heating/cooling the target vessel and/or heating/cooling the target material when the latter is flowing in a circuit.

The liquid target material can be standing as a bath in a container, be a free-standing jet or a jet enclosed on one or more sides by a wall.

Variant: the target temperature can exceed 500° C. the then also released Po can be separated from the At in a subsequent standard radiochemical separation.

The incident alpha beam with maximum 27.5-30 MeV energy is provided by a particle accelerator (cyclotron, LINAC, etc.). An alpha beam with slightly higher energy can be used by reducing its energy with a suitable degrader to ≤(27.5-30) MeV before interacting with the target.

The exact choice of the energy in the interval 27.5-30 MeV is determined by the requirements towards radioisotopic purity: lower energies give lower $^{211}At$ yield and no $^{210}At$ contamination, higher energies give higher $^{211}At$ yield with increasing $^{210}At$ contamination.

For applications where a significant contamination with $^{210}At$ is acceptable (e.g. certain in vitro studies), an alpha beam energy higher than 30 MeV can be used, leading to further increased production of $^{211}At$.

The alpha beam can be vertically incident onto the target, or preferentially under a flat angle to reduce the local power deposition. The beam can be swept over part or the entire surface of the target.

The alpha beam can enter the target enclosure via a window or via a differentially pumped section.

The target material can be kept in motion by pumping, mechanical shaking, electromagnetic agitation, etc. to assure a better temperature homogeneity and thus allow for higher beam currents without the risk of local overheating.

The gas stream can be used to cool the surface of the irradiated target.

The inert gas can be replaced by any other gas if the latter is compatible with the integrity of the target, the enclosure and the catcher surface.

A chimney or baffles can be used to condense evaporating target material before it reaches the catcher.

The entire target enclosure and all surfaces which the released astatine can encounter, except the catcher, is kept at a sufficiently high temperature to avoid a condensation of astatine at places other than the catcher.

Any of the known catchers can be used: e.g. Ag, silica gel or cooled surfaces of plastic, quartz, etc. or water or other solvents.

Several chambers with catchers can be attached to the target chamber and connected/disconnected from the latter without interruption of the irradiation for a significant time.

Variant: instead of on-line separation, the irradiation can be performed with a reduced target temperature. The target is then heated afterwards when needed to release the astatine. This non-destructive batch-mode operation has still the advantage that the same target unit can be used many times.

Embodiment IV

On-Line Production of Carrier-Free $^{204\text{-}210}$At and Application for In Vitro or In Vivo Biodistribution Studies or Dosimetry Via PET, Gamma-Spectrometry or SPECT 1. Application:

$^{211}$At is a very promising isotope for targeted alpha therapy (TAT), but it does not emit positrons. Therefore this isotope is not useful for imaging via PET (positron emission tomography). The provided astatine isotopes $^{204\text{-}207}$At allow for the first time to use this powerful technique for diagnostics in vitro (development of new At-labelled compounds) and in vivo (individual dosimetry to adapt the dose of a $^{211}$At-TAT). Moreover the gamma emission with high branching ratios of $^{204\text{-}210}$At allows to use the latter as convenient radiotracers for biodistribution studies or even for in vitro or in vivo dosimetry with SPECT (single photon emission computerized tomography).

2. Method:

1a) On-Line Production of a Cocktail of Different At Isotopes

A molten Bi target is irradiated with protons of >140 MeV energy {unit 1}. $^{210\text{-}x}$At isotopes are produced by $^{209}$Bi(p,pi$^{-}$ xn) double charge-exchange reactions as well as by secondary $^{209}$Bi(alpha,xn) and $^{209}$Bi($^{3}$He,xn) reactions with the alpha and $^{3}$He produced in (p,alpha) and (p,$^{3}$He) reactions respectively. Astatine is released {units 2,3} and is transported either under vacuum or in inert gas {unit 7} to a suitable catcher {unit 8} surface, e.g. silver. No polonium is released for temperatures below 500° C. The catcher is mounted in a way to be easily changeable once the desired amount of At has been collected on it. This method will produce a mixture of astatine isotopes which can be used as gamma-emitting radiotracers, e.g. for biodistribution studies.

Thus, method 1a) utilizes a combination of units 1, 2, 3, 7 and 8.

1b) Off-Line Separation of Individual At Isotopes.

Optionally isotopically pure samples can be produced by inserting the catcher containing the At isotopes (produced according to 1a, {units 1-3, 7, 8}) into an oven {unit 10} attached or integrated into an ion source. Heating the catcher will release the At which is transported either under vacuum or in inert gas flow {unit 7} to a plasma ion source {unit 11} where At is single positively ionized. The ions are extracted from the ion source, accelerated to typically several tens of keV {unit 12} and separated in a magnetic sector field according to the mass/charge ratio {unit 13}. The ions are collected {unit 14} on backings covered with a thin film of salt which is later dissolved and used to label a bio-conjugate, or a refractory material {unit 14} from where the At can be released in gaseous form by dry distillation. Alternatively the ions are directly implanted into nanoparticles, etc. {unit 14} for labelling of the latter.

Thus, method 1b) utilizes a combination of units 1, 2, 3, 7, 8, 10, 11, 12, 13 and 14.

2) On-Line Production and Separation of Individual At Isotopes

A molten Bi target is irradiated with protons of >140 MeV energy {unit 1}. $^{210\text{-}x}$At isotopes are produced by $^{209}$Bi(p,pi$^{-}$ xn) double charge-exchange reactions as well as by secondary $^{209}$Bi(alpha,xn) and $^{209}$Bi($^{3}$He,xn) reactions with the alpha and $^{3}$He produced in (p,alpha) and (p,$^{3}$He) reactions respectively. Astatine is released {units 2,3} and is transported either under vacuum or in inert gas flow {unit 7} to a plasma ion source {unit 11} where At is single positively ionized. The ions are extracted from the ion source, accelerated to typically several ten keV {unit 12} and separated in a magnetic sector field according to the mass/charge ratio {unit 13}. The ions are collected on backings {unit 14} covered preferably with a thin film of salt which is later dissolved and used to label a bio-conjugate. Alternatively the ions are directly implanted into nanoparticles, etc. {unit 14} for labelling of the latter.

Thus, method 2) utilizes a combination of units 1, 2, 3, 7, 11, 12, 13 and 14.

Particular Advantages Include:

No astatine isotope has so far been used for PET imaging. The inventors provide astatine isotopes for PET imaging and as convenient gamma emitters for biodistribution studies and/or in vitro or in vivo dosimetry. Due to the higher branching ratio for gamma emission compared to $^{211}$At, the ratio "signal to radiotoxicity" is improved by a big factor (orders of magnitude). The inventors have performed a demonstration of the on-line production of mass-separated astatine beams from a Pb/Bi target irradiated with 1.4 GeV protons ("proof-of-principle"). The inventor's method allows to collect the At isotopes parasitically from any liquid Bi containing target irradiated with high energy particles, e.g. from Pb/Bi targets used in spallation neutron sources, ADS, etc. Particularly strong undissociable bonds to nanoparticles can be obtained by the ion-implantation labelling. The continuous, automated production without manual operation steps ideally suited for industrial production is demonstrated.

In summary, the methods provided within this embodiment comprise the following features:

A pure Bi metallic target or a Bi containing alloy is used as target.

During irradiation the target is kept in a temperature range between the melting point and ca. 500° C. The temperature is controlled by heating/cooling the target vessel and/or heating/cooling the target material when the latter is flowing in a circuit.

The liquid target material can be standing as a bath in a container, be a free-standing jet or a flow enclosed on one or more sides by a wall.

Variant: the target temperature can exceed 500° C. if the then also released Po is separated from the At in a subsequent standard radiochemical separation or left in the radioisotope product if it is not considered as disturbing for the application.

The incident proton beam with >140 MeV energy is provided by a particle accelerator (cyclotron, LINAC, synchrotron, etc.).

The proton beam can enter the target enclosure via a window or via a differentially pumped section.

The proton beam can be replaced by a beam of light or heavy ions (d, $^{3}$He, alpha, etc.).

The target material can be kept in motion by pumping, mechanical shaking, electromagnetic agitation, etc. to assure a better temperature homogeneity and thus allow for higher beam currents without the risk of local overheating.

The inert gas can be replaced by any other gas if the latter is compatible with the integrity of the target, the enclosure and the catcher surface.

A chimney or baffles can be used to condense evaporating target material before it reaches the catcher or ion source.

The entire target enclosure and all surfaces which the released astatine can encounter, except the catcher, is kept at a sufficiently high temperature to avoid a condensation of astatine at places other than the catcher.

Any of the known catchers can be used: e.g. Ag, silica gel or cooled surfaces of plastic, quartz, etc. or water or other solvents.

Several chambers with catchers can be attached to the target chamber and connected/disconnected from the latter without interruption of the irradiation for a significant time.

Variant: instead of on-line separation, the irradiation can be performed at a reduced target temperature. The target is then heated afterwards when needed to release the astatine.

The target (and ion source respectively) are heated by any suitable mean (Ohmic heating, electron bombardment, radio-frequency, infrared heating, laser heating, energy loss of the incident beam, etc.) or any combination of these methods.

The target is connected to the ion source in a way that no other escape path is available for the radioisotopes.

The effusing radioisotopes can be transported by a flow of inert gas (He, Ar, . . . ) to the ion source instead of being transported by vacuum diffusion.

The mass separation can be performed with any mass-selective device, e.g. a Wien-filter, a radio-frequency quadrupole, etc. instead of the magnetic sector field.

The mass-separated ion beam is implanted into a salt layer.

The salt layer containing the radioisotopes is subsequently dissolved in a small volume of water or the eluting agent.

The salt cover of the backings can be replaced by many other water-soluble substances (sugar, . . . ) or by a thin ice layer (frozen water or other liquid). Instead of dissolving, the latter is subsequently melted by heating with any suitable method (Ohmic heating, infrared heating, radio-frequency heating, . . . ).

Instead of a soluble matrix, the ion beam can also be implanted into any other solid matrix, e.g. a metal foil. In this case one needs additionally a chemical separation of the desired isotope from the matrix material that usually disturbs the chromatographic process.

In all cases (i.e. elution from the catcher, dissolving of salt, etc. layer, melting of ice layer) the product fraction is usually obtained in a small volume and can be directly used for the labelling procedure of bio-conjugates or be directly injected into a chromatographic system for further purification.

A particularly simple separation that allows to obtain At in gaseous form can be achieved by thermal release from a refractory matrix.

Any of the classical radio-chemical and radio-chromatographical processes (precipitation, electrochemical separations, extraction, cation exchange chromatography, anion exchange chromatography, extraction chromatography, thermo chromatography, gas chromatography, etc.) suitable for the separation of astatine can be applied for the separation of the desired product from isobars and pseudo-isobars (stemming from molecular sidebands like oxides or fluorides appearing at the same mass settings), from daughter products generated by the radioactive decay of the collected radioisotopes during collection and processing and from other impurities.

Ligands used for the chemical separation process are eventually remaining with the product fraction and need to be eliminated before further labelling procedures. Evaporation is the most suitable way for many cases.

Nanoparticles, macro-molecules, microspheres, macroaggregates, ion exchange resins or other matrices used in chromatographic systems can be labelled directly by implanting the radioactive ion beam into them. For cases where the radioisotopic purity is already sufficient or for implantation into ion exchange resins or other matrices used in chromatographic systems, this can be done directly on-line. Else, after the standard purification steps (radio-chromatographic separation of isobars) the product is again injected into an ion source, ionized, accelerated and implanted.

The so obtained products are carrier-free and isotopically pure.

The process can be operated with all the technological steps of the chain as described. However, one can reduce freely the number of steps in many cases to adapt to the required purity of the respective application.

Embodiment V

Production of Carrier-Free Radioisotopes of the Rare Earth Elements as Well as Certain Other Elements and Use for In Vivo Application 1. Method:

The universal method will be outlined in the following preferred examples:

First Variant Production of Carrier-Free $^{149}$Tb and Use for In Vivo Application The radionuclide $^{149}$Tb ($T_{1/2}$=4.118 h) has a 16.7% branching ratio for alpha-emission. It is the most promising lanthanide isotope for targeted alpha therapy (TAT). A very high specific activity is crucial for the success of TAT.

The isotope ($^{149}$Tb as example) is generated (among many other isotopes) by irradiating a Ta-foil target kept at a temperature above 2000° C. with energetic particles, e.g. high energy protons (E>100 MeV) {unit 1}. The generated rare earth isotopes are escaping {units 2,3} from the target material and transported in vacuum {unit 7} to the ion source, where they are ionised into single positively charged ions using any kind of ionisation principles (surface ionisation, resonant laser ionisation or plasma ionisation) {unit 11}. The ions are extracted from the ion source, accelerated to typically several tens of keV {unit 12} and separated in a magnetic sector field according to the mass/charge ratios into isobars {unit 13}. The isobars are collected {unit 14} on backings covered preferably with a thin film of a salt.

Thus, the first variant utilizes a combination of units 1, 2, 3, 7, 11, 12, 13 and 14.

In the following the "application unit" is utilized:

By dissolving the layer in a small volume of clean water (typically 50-100 μl) the carrier free isotope solution is transferred to the top of a column for isobaric separation by means of any of the radio-chromatography processes. The carrier free $^{149}$Tb in mass separated form is obtained in a volume of ~200 μl, if alpha-hydroxisobutyric acid (alpha-HIBA) and cation exchange resin is used for the chromatography.

The ligand used for the chromatographic separation is removed by evaporation and the remaining $^{149}$Tb is dissolved in a suitable small volume of 50 mM HCl-solution. This solution is directly used for the labelling procedure of bio-conjugates. Bio-conjugates in this context are any protein (monoclonal antibodies, their fragments, HAS=Human serum albumin, microspheres or macro-aggregates made from HAS, other protein molecules, peptides and oligonucleotides that are conjugated with chelating groups through or without linking molecules. The labelling procedure is fast (less than 10 minutes at room temperature) and quantitative. The obtained labelled bio-conjugate does not need any further purification, as it is usually needed in other protocols.

The labelled bio-conjugate can be directly injected into patients for diagnostic procedures or therapeutic protocols.

The radio-bio-conjugates obtained in this way are used for diagnostic imaging procedures as SPECT (single photon emission computerized tomography), quantitative PET (positron emission tomography) imaging for individual in vivo dosimetry, or for targeted beta (using beta emitting isotopes), targeted alpha therapy (TAT) (using the alpha emitting $^{149}$Tb) or the Auger-therapy (using the Auger electron emitters).

Second Variant Production of high-purity $^{82}$Sr for $^{82}$Sr/$^{82}$Rb generators The radionuclide $^{82}$Sr ($T_{1/2}$=25.3 d) decays via the EC process generating the short-lived positron emitting daughter nuclide $^{82}$Rb with 76.4 s half-life. This short-lived isotope is used in nuclear cardiology as myocardial perfusion tracer using positron emission tomography (PET). For this purpose special dedicated $^{82}$Sr/$^{82}$Rb generator systems have been developed, where the main generator column can be replaced frequently.

Today the $^{82}$Sr is produced either via spallation reaction using Nb or Mo as target material or by the $^{85}$Rb(p,4n)$^{82}$Sr process using metallic Rb targets that are exposed to intense proton beams with en energy >70 MeV. The drawback of the existing technology is that $^{85}$Sr ($T_{1/2}$=64.8 d) is unavoidable generated in an amount that is 3-5 times higher. Thus, the obtained $^{82}$Sr preparation is "contaminated" by a factor 3 to 5 larger amount of a longer lived Sr isotope, that generates 514 keV gamma radiation in its EC decay. This large $^{85}$Sr contribution causes larger shielding efforts for the transport and reduces the shelf-time of the generator in the routine clinical use. In addition the production process is accompanied with relatively large quantities of liquid radioactive waste.

The inventors provide a non-destructive technique, that allows to produce the $^{82}$Sr without generating liquid radioactive waste and optional in isotopically clean form without the large $^{85}$Sr contamination.

Version A

Non-target-destructive off-line production of $^{82}$Sr without mass separation

- configure a target {unit 1} consisting of 0.2-1 mm thick plates or foils or wires made from Zr or related alloys
- keep the target in vacuum or inert atmosphere
- irradiate with high energy particles (E>76 MeV, preferable protons) to generate the $^{82}$Sr {unit 1}, that is initially homogenously distributed in the target matrix
- heat the target under vacuum (or inert gas conditions) up to 1100-1300° C.
- during 10-60 min the $^{82}$Sr diffuses {unit 2} to the target surface, evaporates {unit 3} into the vacuum and becomes adsorbed at another metal surface used as catcher {unit 8} foil (metals of the group 5, 6, 7 and 8, preferable Ta, Nb or W), kept at a temperature below 1200
- cool the system down and remove the catcher foil, extract the Sr in a conventional chemical way As option one can use an inert gas flow to transport {unit 7} the Sr from the target unit into a catcher cavity, where the Sr is adsorbed at any cold surface provided for further chemical treatment.

The original target can be reused for the next irradiation cycle.

Thus, version A of the second variant utilizes a combination of units 1, 2, 3, 7 and 8.

Version B

Non-target-destructive production of high purity $^{82}$Sr with mass separation in off-line or on-line mode

- target unit according to version A {unit 1}
- the Sr released {units 2,3} from the target material is here ionised using a suitable ion source (e.g. surface ionisation) {unit 11}
- single positively charged $Sr^+$ ions are extracted from the target ion source unit {unit 12}

The extracted ions can be collected on a catcher {unit 14} before or after passing through a mass-selective device {unit 13}.

The process can be operated on-line (irradiation and separation simultaneously) or off-line (long irradiation and time to time a short mass separation)

High purity $^{82}$Sr is obtained

Thus, version B of the second variant utilizes a combination of units 1, 2, 3, 11, 12, 13 and 14.

3. Variant: New Type of $^{44}$Ti/$^{44}$Sc Generator

The radionuclide $^{44}$Sc ($T_{1/2}$=3.9 h) is a suitable positron emitter (beta$^+$ branching ratio of 94.34%) and has as such a great future potential in nuclear medical functional imaging using positron emission tomography (PET). Presently new approaches for systemic radionuclide therapy are under development, that are based on bio-selective molecules, liposomes or nanoparticles, that are used as carrier vehicle to transport therapeutic radionuclides into tumor cells or tumor tissue.

The quantitative information of the bio-distribution will be accessed using PET imaging based on positron emitting radionuclides of elements that are homologues of the element used for the therapy. Thus, metallic position emitting radionuclides with a half-life of few hours are most suitable to perform this kind of studies and are demanded. $^{44}$Sc is most suitable for this kind of studies, but by far not available today and not in the required quantity. $^{44}$Sc can be made available from the decay of the mother isotope $^{44}$Ti (half-life 60 years).

The inventors provide a new type of $^{44}$Ti/$^{44}$Sc generator principle. Due to the long half-life the well known principle used in the $^{99}$Mo/$^{99m}$Tc generator cannot be applied here.

Ti in form of pure metal or alloy will be irradiated {unit 1} with medium or high energy (E>20 MeV) charged (e.g. protons) or neutral particles to generate in a non-selective way the radionuclide $^{44}$Ti inside the target matrix. In addition other isotopes are formed, mainly of the elements Sc, Ca, K and Ar. After a certain cooling period (to let the short-lived isotopes decay) the Ti-target will be annealed at a temperature ≥1000° C., in order to release most of the remaining radioactivity except the $^{44}$Ti.

The inventors have studied extensively the transport processes of tracer elements inside the Ti-matrix and determined the corresponding diffusion coefficients {unit 2}. In this systematic studies the inventors learnt, that the tracer elements are released from Ti-matrix in the following order:

Sc>Ca>K>Ar.

The diffusion {unit 2} of Sc is fastest and already at relatively low temperatures one can separate Sc from a thick Ti-matrix within relatively short time.

The adsorption enthalpy of Sc at the Ti surface is low, consequently Sc is evaporated {unit 3} from Ti at relatively low temperatures. On the other hand the adsorption enthalpy of Sc on the surface of most noble or refractory metals (i.e. Ta, W, Re, Pt, Au, . . . ) is high. Consequently Sc is adsorbed {unit 8} to those surfaces at the same temperature where it is released from the Ti-matrix.

The annealing procedure with the transport of the Sc from the Ti target to the adsorbing surface can be performed in vacuum or in an inert gas atmosphere {unit 7}.

The $^{44}$Sc adsorbed at the metal surfaces is then removed by any of the known techniques (dissolution, electrochemical, desorption) and conditioned for the use in tracer molecule labelling.

The process can be repeated without limitations, since the half-life of the $^{44}$Ti is very long and the Ti matrix does not change its behaviour.

Thus, the third variant utilizes a combination of units 1, 2, 3, 7 and 8.

Particular Advantages Include:

The inventors have shown for the first time by an in vivo experiment that $^{149}$Th can be successfully applied for TAT ("proof of principle"). The quality of the radioisotope product generated according to the inventor's method allows the application of primary-labelled bioconjugates without further treatment or purification (usually required in alternative production routes). Many of the listed radioisotopes of interest which will become available with the inventor's method are provided for the first time for application in life science research and medical application. In most of the provided variants the target is reusable many times, which is not the case in standard methods where the irradiated target is destroyed by dissolution, giving large amounts of liquid waste. For the first time the inventors provide the direct labelling of nanoparticles, macro-molecules, etc. by radioactive ion implantation. This yields in many cases a stronger undissociable bond than presently used methods. For the first time the inventors provide the production of mass-separated $^{82}$Sr which can serve for improved $^{82}$Sr/$^{82}$Rb generators and have shown the parameter range where Sr is released ("proof of principle"). For the first time the inventors provide a dry $^{44}$Ti/$^{44}$Sc generator and have shown the parameter range where Sc is released ("proof of principle"). The inventors provide that the so produced $^{44}$Sc is used as PET isotope e.g. as representative tracer for quantitative biodistribution studies of radiolanthanide labelled bio-selective molecules, lyposomes, nanoparticles, etc. The method is ideally suited for large scale industrial production since it has been demonstrated that it is continuous and automated with few manual operation steps.

In summary, the methods provided within this embodiment comprise the following features:

This approach works for $^{28}$Mg, $^{42}$K, $^{43}$K, $^{45}$Ca, $^{47}$Ca, $^{81}$Rb, $^{82}$Sr, $^{83}$Sr, $^{85}$Sr, $^{89}$Sr, $^{172}$Hf, $^{175}$Hf and all radionuclides of the rare earth elements out of which the following have dedicated relevance: $^{44}$Sc, $^{44m}$Sc, $^{46}$Sc, $^{47}$Sc, $^{85}$Y, $^{86}$Y, $^{87}$Y, $^{88}$Y, $^{134}$Ce/La, $^{137}$Ce, $^{139}$Ce, $^{141}$Ce, $^{143}$Pr, $^{138}$Nd/Pr, $^{140}$Nd/pr, $^{147}$Nd, $^{149}$Pm, $^{142}$Sm/Pm, $^{153}$Sm, $^{155}$Eu, $^{147}$Gd, $^{149}$Gd, $^{149}$Tb, $^{152}$Tb, $^{155}$Th, $^{161}$Tb, $^{157}$Dy, $^{159}$Dy, $^{166}$Ho, $^{165}$Er, $^{169}$Er, $^{165}$Tm, $^{167}$Tm, $^{169}$Yb, $^{177}$Yb, $^{172}$Lu, $^{177}$Lu.

The Ta target can be replaced by Hf, W, Re, Ir or alloys or compounds containing any of these metals. This material can be used in pure form or mixed with other materials.

For producing radioisotopes of the lighter elements Mg, K, Ca, Sc, Rb, Sr, Y also targets made from Zr, Nb, Mo, Ru, Rh or alloys or compounds containing these elements can be used, in addition to the ones mentioned above.

For producing radioisotopes of the lighter elements Mg, K, Ca, Sc also targets made from Ti or V or alloys or compounds containing these elements can be used, in addition to the ones mentioned above.

For producing $^{28}$Mg also targets made from Si or alloys or compounds containing Si can be used, in addition to the ones mentioned above.

The target can be replaced by the distillation residue from previously irradiated targets of Hg, Pb, Bi or an alloy containing any of these elements.

The target material can be in form of foils, wires, powder, foam, etc.

The target material, the target enclosure, the ion source and all surfaces the effusing radioisotopes might interact with, are held at high temperature. "High" means of the order of 60-90% or preferably 60-95% of the melting point of the material.

The target is connected to the ion source in a way that no other escape path is available for the radioisotopes.

The incident proton beam can be replaced by energetic light ions (d, $^{3}$He, $^{4}$He, . . . ), heavy ions, neutrons, electrons or photons.

The target and ion source are heated by any suitable mean (Ohmic heating, electron bombardment, radio-frequency, infrared heating, laser heating, energy loss of the incident beam, etc.) or any combination of these methods.

Variant: The target can also be kept at lower temperatures during irradiation, then being heated off-line for the release of the radioisotopes. After release of a sufficient amount of the radioisotopes the target is again irradiated, heated, irradiated, . . . (batch-mode operation).

Variant: In cases where the isotope produced during irradiation is long-lived and decays to a daughter radioisotope of interest, the once irradiated target can be used as a dry generator by heating it to a temperature where the daughter radioisotope is released while the long-lived radioisotope remains in the target matrix. A particular application of this method provides a new type of dry $^{44}$Ti/$^{44}$Sc generator.

dry $^{44}$Ti/$^{44}$Sc generator: Ti in form of pure metal or alloy is irradiated with medium or high energy (E>20 MeV) charged (e.g. protons) or neutral particles to generate in a non-selective way the radionuclide $^{44}$Ti inside the target matrix. In addition other isotopes are formed, mainly of the elements Sc, Ca, K and Ar. After a certain cooling period and waiting period (to let the short-lived isotopes decay) the Ti-target will be annealed at a temperature ≥1000° C., in order to release most of the remaining radioactivity except the $^{44}$Ti. The diffusion of Sc is fastest and already at relatively low temperatures one can separate Sc from a thick Ti-matrix within relatively short time. The adsorption enthalpy of Sc at the Ti surface is low, consequently Sc is evaporated from Ti at relatively low temperatures. On the other hand the adsorption enthalpy of Sc on the surface of most noble or refractory metals (i.e. Ta, W, Re, Pt, Au, . . . ) is high. Consequently Sc is adsorbed to those surfaces at the same temperature where it is released from the Ti-matrix. The annealing procedure with the transport of the Sc from the Ti target to the adsorbing surface can be performed in vacuum or in an inert gas atmosphere. The $^{44}$Sc adsorbed at the metal surfaces is then removed by any of the known techniques (dissolution, electrochemical, desorption) and conditioned for the use in tracer molecule labelling. The process can be repeated without limitations, since the half-life of the $^{44}$Ti is very long and the Ti matrix does not change its behaviour. In this particular process isotopically pure $^{44}$Sc is obtained even without mass separation since no other Sc isotope is produced as daughter of a long-lived mother isotope remaining in the Ti matrix.

The effusing radioisotopes can be transported by a flow of inert gas (He, Ar, . . . ) to the ion source instead of the transport by vacuum diffusion.

The target is connected to the ion source in a way that no other escape path is available for the radioisotopes.

The desorption and transport to the ion source can be accelerated by chemical evaporation, adding a small amount of suitable agent (halogens or volatile halogenated compounds).

Resonant laser ionisation can be performed with laser light generated from dye lasers, Ti:sapphire lasers or any other type of wavelength tunable light sources (OPO, . . . ) which are pumped by solid state lasers (Nd:YAG, Nd:YLF, Nd:YVO, diode, . . . ) or gas lasers (copper vapour lasers, etc.).

Resonant laser ionization is particularly efficient if several or all thermally populated low-lying atomic states of the element to be ionized are simultaneously resonantly excited.

This applies e.g. to the element terbium where several of the atomic states $4f^9\ 6s^2\ {}^6H^o_{15/2}$, $4f^8(^7F)5d6s^2\ {}^8G_{13/2}$, $4f^8(^7F)5d6s^2\ {}^8G_{15/2}$, $4f^8(^7F)5d6s^2\ {}^8G_{11/2}$ have to be resonantly excited simultaneously with separate laser beams to the corresponding excited states and from there (via an optional intermediate step) to the continuum or to an autoionizing state.

The mass separation can be performed with any mass-selective device, e.g. a Wien-filter, a radio-frequency quadrupole, etc. instead of the magnetic sector field.

Often several isotopes of the same element, or isobars with comparable masses are produced in the same system. In this case a mass-selective device is of advantage, which allows to collect simultaneously several masses.

The mass separation process is of particular importance if another radioisotope of the element in question is produced in such quantities that it causes a high radiation dose rate (problems of handling), e.g. in the case of $^{82}Sr$ which is disturbed by the co-production of $^{85}Sr$.

The mass-separated ion-beam is implanted into a salt layer.

The salt layer containing the radioisotopes is subsequently dissolved in a small volume of water or the eluting agent and as such directly injected into the chromatographic system.

The salt cover of the backings can be replaced by many other water-soluble substances (sugar, . . . ) or by a thin ice layer (frozen water or other liquid). Instead of dissolving, the latter is subsequently melted by heating with any suitable method (Ohmic heating, infrared-heating, radio-frequency heating, . . . ).

Instead of a soluble matrix, the ion beam can also be implanted into any other solid matrix, e.g. a metal foil. In this case one needs additionally a chemical separation of the desired isotope from the matrix material that usually disturbs the chromatographic process.

Any of the conventional radio-chemical and radio-chromatographical processes (precipitation, electrochemical separations, extraction, cation exchange chromatography, anion exchange chromatography, extraction chromatography, thermo chromatography, gas chromatography, etc.) suitable for the separation of rare-earth elements can be applied for the separation of the desired product from isobars and pseudo-isobars (stemming from molecular sidebands like oxides or fluorides appearing at the same mass settings), from daughter products generated by the radioactive decay of the collected radioisotopes during collection and processing and from other impurities.

A particularly simple and efficient separation from the implantation substrate can be achieved by thermal release from a refractory matrix.

The product fraction is usually obtained in a small volume.

Ligands used for the chemical separation process are eventually remaining with the product fraction and need to be eliminated before further labelling procedures. Evaporation is the most suitable way for many cases, e.g. for alpha-HIBA.

The remaining product is dissolved in a small volume of solution suitable for direct labelling, e.g. 50-100 mM HCl.

The obtained solution is directly used for the labelling procedure of bio-conjugates.

Bio-conjugates in this context are any protein (monoclonal antibodies, their fragments, HAS=Human serum albumin, microspheres or macro-aggregates made from HAS, other protein molecules, peptides and oligonucleotides that are conjugated with chelating groups (e.g. pure or derivatives of DTPA, DOTA or any similar type) through or without linking molecules.

The labelling procedure is fast (less than 10 minutes at room temperature) and quantitative.

The obtained labelled bio-conjugate does not need any further purification, as it is usually needed in other protocols.

The labelled bio-conjugate can be directly injected into patients for diagnostic procedures: SPECT=single photon emission computerized tomography (e.g. $^{157}Dy$), quantitative PET=positron emission tomography imaging for individual in vivo dosimetry (e.g. $^{83}Sr$, $^{138}Nb$, $^{142}Sm$, etc.) or for therapeutic protocols: radio-immuno-therapy (RIT) using beta emitting isotopes (e.g. $^{169}Er$), targeted alpha therapy (TAT) using the alpha emitting $^{149}Tb$, or Auger-therapy using the Auger electron emitters (e.g. $^{165}Er$).

Nanoparticles, macro-molecules, micro-spheres, macro-aggregates, ion exchange resins or other matrices used in chromatographic systems can be labelled directly by implanting the radioactive ion beam into them. For cases where the radioisotopic purity is already sufficient or for implantation into ion exchange resins or other matrices used in chromatographic systems, this can be done directly on-line. Else, after the standard purification steps (radio-chromatographic separation of isobars) the product is again injected into an ion source, ionized, accelerated and implanted.

The so obtained products are carrier-free and isotopically pure.

The process can be operated with all of the technological steps in the chain as described. However, one can reduce freely the number of steps in many cases without disturbing the final quality of the labelled product for in vivo application.

Embodiment VI

Fission Production of Neutron-Rich Lanthanide and Tin Isotopes

1. Application:

The radionuclide $^{153}Sm$ ($T_{1/2}$=46.3 h) is a beta-emitting isotope with great potential in endo-radionuclide therapy. It is mainly used today in EDTMP solution for palliative treatment of bone cancer. Monoclonal antibody conjugates can be labelled as well, while, on the other hand the use for peptide labelling is hampered due to the insufficient specific activity. $^{153}Sm$ is produced today generally via the $^{152}Sm$(n,gamma) $^{153}Sm$ process using enriched $^{152}Sm$ as target material.

2. Method:

For the production of neutron-rich lanthanide isotopes the inventors provide the following methods, outlined at the example of $^{153}Sm$:

$^{153}Sm$ can be found among the products of thermal neutron induced fission of $^{235}U$ in reasonable quantities (0.15% cumulative yield). High-energy fission (e.g. induced by high energy protons) increases this yield significantly and moreover removes the restriction to the fissile target nuclides (as $^{235}U$ or $^{239}Pu$) and $^{238}U$ or $^{232}Th$ become also useful as target. The separation of the Sm-fraction from the fission product mixture provides a $^{153}Sm$ preparation in non carrier added quality, with a much higher specific activity than via the classical $^{152}Sm$(n,gamma)$^{153}Sm$ process.

Version 1: Classical Chemical Separation of $^{153}Sm$ from Fission Products

- fission target: any fissile isotope as well as Th and U in natural composition or depleted $^{238}U$, in any possible chemical form: metallic, carbide, oxide, sulphide, etc.
- irradiate with thermal or fast neutrons, charged particles, electrons or photons for initiating the fission process {unit 1}
- conventional (wet-chemical) process for separation of the Sm fraction, the Sm-fraction will contain only $^{153}Sm$ and traces of $^{151}Sm$ (93 year half-life) and small fission produced quantities of stable Sm-isotopes. The $^{153}Sm/^{151}Sm$ ratio can be optimized by reducing the time between start of irradiation and Sm separation.

Version 2: Method Described in Version 1, Combined with Off-Line Mass Separation insert the obtained (along version 1) Sm fraction {unit 9} into a dedicated ion source cavity (=oven) {unit 10} of amass separator evaporate the Sm {unit 10} and ionise it by using surface ionisation, laser ionisation or plasma discharge ionisation {unit 11} to obtain $Sm^+$ ions that are extracted, accelerated {unit 12} and separated using a dedicated mass-dispersive device {unit 13}

$^{153}Sm$ samples produced along the $^{152}Sm$(n,gamma)$^{153}Sm$ process can be transformed by the same method into carrier free quality preparations as well.

Thus, version 2 utilizes a combination of units 1, 9, 10, 11, 12 and 13.

Version 3: Non-Target-Destructive On- or Off-Line Separation of $^{153}Sm$ target material in the chemical form of carbide or carbide diluted in excess graphite create fission via one of the mentioned nuclear reactions {unit 1} heat the target during or after irradiation to temperatures above 2000° C.

Sm generated in the fission process is released {units 2,3} from the target material and transported to the ion source under vacuum or inert gas flow {unit 7}

Sm is ionised via surface ionisation or/and laser ionisation or plasma ionisation {unit 11} the single charged positive Sm ions are than extracted from the target ion source unit, accelerated {unit 12} and separated by passing through a mass-selective device {unit 13} carrier free $^{153}Sm$ is obtained in atomic form or in a molecular sideband (oxide, halide {unit 9})

Thus, version 3 utilizes a combination of units 1, 2, 3, 7, 9, 11, 12 and 13.

Variant:

With the methods of versions 2 and 3 also non-carrier added $^{117m}Sn$ can be produced. With high-energy fission {unit 1} $^{117m}Sn$ is directly populated (low-energy fission populates mainly the lower-Z mass-117 isobars which decay mainly to $^{117g}Sn$) and the isomeric ratio $^{117m}Sn/^{117g}Sn$ is strongly enhanced. Using resonant laser ionization {unit 11} the ratio $^{117m}Sn/^{117g}Sn$ can be enhanced further, by either using the selection rules between magnetic substrates (more transitions possible for atoms with high total spin F) or by tuning a small-bandwidth laser to selectively ionize $^{117m}Sn$ via its hyperfine structure differing from that of $^{117g}Sn$.

Particular Advantages Include:

The inventors have performed a demonstration for the on-line production of mass-separated $^{117m}Sn$, $^{153}Sm$, $^{166}Ho$, $^{169}Er$, etc. beams from a $UC_x$ target irradiated with 1.4 GeV protons ("proof-of-principle"). The inventors provide a completely new production process (fission), which provides intrinsically higher specific activities. Non-carrier added samples of $^{117m}Sn$ can be obtained where the $^{117m}Sn/^{117g}Sn$ ratio is improved by several orders of magnitude compared to the conventional production via $^{116}Sn$(n,gamma). The continuous, automated production without manual operation steps ideally suited for industrial production is demonstrated. Particularly strong undissociable bonds to nanoparticles can be obtained by the ion-implantation labelling.

In summary, the methods provided within this embodiment comprise the following features:

Any fissile isotope as well as Th and U in natural composition or depleted $^{238}U$, in any possible chemical form: metallic, carbide, oxide, sulphide, etc. can be used as target.

Some of the target materials can be in form of foils, wires, powder, foam, etc.

The target is irradiated with thermal or fast neutrons, charged particles, electrons or photons for initiating the fission process.

After irradiation a suitable conventional (wet-chemical) process is used for separation of the Sm fraction.

The Sm-fraction will contain only $^{153}Sm$ and traces of $^{151}Sm$ (93 year half-life) and small fission produced quantities of stable Sm-isotopes. The $^{153}SM/^{151}Sm$ ratio can be optimized by reducing the time between start of irradiation and Sm separation.

The Sm-fraction produced as described above is inserted into an oven connected to an ion source.

Evaporation, ionisation, off-line mass separation and collection as described above in Embodiment V for on-line lanthanide separation.

The wanted isotope can be separated as atomic ion or as molecular ion in the corresponding sideband (oxide, fluoride, . . . ).

With the described mass separation process $^{153}Sm$ samples produced along the $^{152}Sm$(n,gamma)$^{153}Sm$ process can be transformed into carrier free quality preparations as well.

With the same methods 1-3 also other beta-emitting radioisotopes, e.g. $^{141}Ce$, $^{143}Pr$, $^{147}Nd$, $^{149}Pm$, $^{161}Th$, $^{166}Ho$ and $^{169}Er$ can be produced. The latter three require fast or high-energy fission to obtain a reasonable yield.

Using high-energy fission, also non-carrier added $^{117m}Sn$ can be produced along the same methods.

Using resonant laser ionization the ratio $^{117m}Sn/^{117g}Sn$ can be enhanced further, by either using the selection rules between magnetic substates (more transitions possible for atoms with high total spin F) or by tuning a small-bandwidth laser to selectively ionize $^{117m}Sn$ via its hyperfine structure differing from that of $^{117g}Sn$.

The described selective ionization of isomers can also be used in the separation process of other isomers, e.g. to improve the $^{177g}Lu/^{177m}Lu$ ratio.

Further Preferred Aspects of the Invention

1. Preferred Aspect: Investigation of Evaporation Characteristics of Po from Liquid Pb—Bi-eutecticum In a first preferred aspect of the present invention, the invention relates to an investigation of evaporation characteristics of polonium from liquid Pb—Bi-eutecticum The evaporation behaviour of polonium and its lighter homologues selenium and tellurium dissolved in liquid Pb—Bi-eutecticum (LBE) has been studied at various temperatures in the range from 482 K up to 1330 K under $Ar/H_2$ and $Ar/H_2O$-atmospheres using F-ray spectroscopy. Polonium release in the temperature range of interest for technical applications is slow. Within short term (1 h) experiments measurable amounts of polonium are evaporated only at temperatures above 973 K. Long term experiments reveal that a slow evaporation of polonium occurs at temperatures around 873 K resulting in a fractional polonium loss of the melt around 1% per day. Evaporation rates of selenium and tellurium are smaller than those of polonium. The presence of $H_2O$ does not enhance the evaporation within the error limits of the inventor's experiments. The thermodynamics and possible reaction pathways involved in polonium release from LBE are discussed.

a. Introduction

Liquid Lead-Bismuth eutecticum (LBE) is proposed to be used as target material in spallation neutron sources [Salvatores, M., Bauer, G. S., Heusener, G.: *The MEGAPIE Initiative*, PSI-Report Nr. 00-05, Paul Scherrer Institut, Villigen, Switzerland, 2000] as well as in Accelerator Driven Systems (ADS) for the transmutation of long-lived nuclear waste [Gromov, B. F., Belomitlev, Yu. S., Efimov, E. I., Leonchuk, M. P., Martinov, P. N. Orlov, Yu. I., Pankratov, D. V., Pashkin, Yu. G., Toshinsky, G. I., Chenukov, V. V., Shmatko, B. A., Stepankov, V. S.: Use of Lead-Bismuth Coolant in Nuclear Reactors and Accelerator-Driven Systems. *Nuclear Engineering and Design* 173, 207 (1997).]. In these systems polonium is formed as a product of (p,xn) and (n,γ)-reactions according to the following processes:

$$^{209}Bi \xrightarrow{(p,xn)} {}^{208,209}Po \qquad (1)$$

$$^{209}Bi \xrightarrow{(n,\gamma)} {}^{210}Bi \xrightarrow{\beta-} {}^{210}Po \qquad (2)$$

Within one year of operation employing a proton beam current of 1 mA around 2 g of polonium are produced in this manner [Atchison, F.: Nuclide Production in the SINQ Target, Report SINQ/816/AFN-702, Paul Scherrer Institute, Villigen, Switzerland, 1997]. Because of the high radiotoxicity of polonium its behaviour is of utmost importance with respect to the safe operation and post-irradiation handling of the target systems and materials as well as for an assessment of the potential risk of accident scenarios.

While the rates of evaporation and transport are of interest for an evaluation of the risk of contamination and incorporation in case of an accident, the development of suitable techniques for the fixation of polonium requires a fundamental knowledge of the chemical mechanisms of the release process.

Previous thermal evaporation studies on polonium from molten Bi and Pb—Bi-eutecticum dealt with the preparation of polonium by neutron irradiation of bismuth and subsequent separation by distillation [Gmelin's Handbook of Inorganic and Organometallic Chemistry, 8$^{th}$ Edition, Polonium, Supplement Vol. 1, Springer-Verlag, Berlin, 1990, p. 421. Jennings, A. S., Proctor, J. F., Fernandez, L. P.: The Large Scale Separation of Polonium-210 from Bismuth. Du Pont Rep., Large Scale Production and Applications of Radioisoptes, DP-1066, 3, Du Pont de Nemour and Co, Aiken, S C, Savannah River Lab, *Vacuum* 17, 584 (1967).] and hazards related to the technical use of LBE in nuclear devices [Tupper, R. B., Minushkin, B., Peters, F. E., Kardos, Z. L.: Polonium Hazards Associated with Lead Bismuth Used as a Reactor Coolant. *Proc. of the Intern. Conf on Fast Reactors and Related Fuel Cycles*, Oct. 28-Nov. 1, 1991, Kyoto, Japan, Vol. 4, p. 5.6-1. Pankratov, D. V., Yefimov, E. I., Burgreev, M. I.: Polonium Problem in Lead-Bismuth Flow Target. Proc. of the Intern. Workshop on the Technology and Thermal Hydraulics of Heavy Liquid Metals, Mar. 25-28, 1996, Schruns, Austria, p. 9.23. Furrer, M., Steinemann, M., Leupi, P.: Dampfdruck von Polonium-210 über einer eutektischen Blei-/Wismut-Schmelze bei 350° C. TM-43-91-08, Paul Scherrer Institut, Villigen, Switzerland, 1991]. The thermodynamics of polonium release from molten LBE at temperatures between 673 and 823 K is investigated in [Buongiomo, J., Larson, C., Czerwinski, K. R.: Speciation of polonium released from molten lead bismuth. *Radiochim.* Acta 91, 153 (2003).]. Additionally, calculations of the polonium release rate based on a Langmuir-type formalism are reported [Yefimov, E. I., Pankratov, D. V.: Polonium and volatile radionuclides output from liquid metal target into ion guide and gas system. *Proc. of the* 2. *Intern. Conf. on Accelerator-Driven Transmutation Technologies and Applications*, Jun. 3-7, 1996, Kalmar, Sweden, p. 1121. Levanov, V. I., Pankratov, D. V., Yefimov, E. I.: The estimation of Radiation Danger of Gaseous and Volatile Radionuclides in Accelerator Driven System with Pb—Bi Coolant. *Proc. of the* 3. *Intern. Conf. on Accelerator-Driven Transmutation Technologies and Applications*, Jun. 7-11, 1999, Prague, Czech Republic, http://www.fjfi.cvut.cz/con_adtt99/. Fischer, W. E.: Dampfdruck und Aktivierung flüchtiger Spallationsprodukte aus dem SINQ-Target, Report SINQ/821/FIN-716, Schweizerisches Institut für Nuklearforschung, Villigen, Switzerland, 1987. Li, N., Yefimov, E., Pankratov, D.: Polonium Release from an ATW Burner System with Liquid Lead-Bismuth Coolant, Report LA-UR-98-1995, Los Alamos National Laboratory, U.S.A., 1998.].

The chemical mechanism of the release of volatiles can be influenced by the composition of the vapour phase. Hydrogen will be formed by spallation reactions in the operating target. Therefore, a certain amount of $H_2O$ will be present in the system, where the vapour pressure of $H_2O$ depends on the oxide content of the liquid alloy. In case of an accident, the alloy can be exposed to air.

In this embodiment the inventors study the thermal release of polonium and its lighter homologues selenium and tellurium from LBE in an inert gas/hydrogen atmosphere. Some additional experiments employing an inert gas/water atmosphere were also conducted.

For a suitable experimental setup, see Example 1.

b. Results and Discussion

The results of the short-term evaporation experiments are shown in FIGS. 2-4. A comparison of the release behaviour of selenium, tellurium and polonium from LBE (1 h experiments) in an Ar/7%-$H_2$ atmosphere at temperatures between 482 and 1330 K is shown in FIG. 2. Measurable amounts of the chalcogens are released at temperatures starting from 973 K. The volatility increases in the order Se<Te<Po. Accordingly, the temperatures at which 50% of the total amount of chalcogen is released decrease from 1300 K (Se) to 1270 (Te) and 1200 K (Po). In the temperature range of interest for technical applications like liquid metal spallation targets (473-723 K) no release has been observed within the experimental errors indicated as error bars in the figures. FIG. 3 shows a comparison of the release behaviour of polonium in Ar/7%-$H_2$ and water saturated Ar atmosphere. The presence of water does not lead to a pronounced increase of the volatility of polonium between 498 and 873 K. The sample investigated at 1108 K suffered from oxidation in the water-containing atmosphere and had reacted with water and the quartz tissue within an hour to form presumably a Pb/Bi-silicate glass. However, these chemical reactions do not lead to a significant increase or decrease of the polonium evaporation rate.

FIG. 4 shows a comparison of the fractional release of polonium from LBE samples of different sizes as a function of temperature. For both sample sizes a measurable release of polonium occurs only at temperatures above 973 K. However, above this temperature the release of polonium from 0.14 g samples is about twice as fast as from 0.65 g samples. From an evaluation of the surface to volume ratios and the radius ratios of the two sample sizes no clear conclusion can be drawn with respect to a desorption- or diffusion-controlled process. However, a detailed evaluation of the mechanism of the release process is beyond the scope of this work.

The results of the inventor's long-term experiments are presented in FIGS. 5 and 6. FIG. 5 shows the fractional release of polonium from LBE measured in an Ar/7%-$H_2$ atmosphere at different temperatures as a function of time for periods up to 28 days. At 646 and 721 K, which are temperatures considered for the operation of liquid metal spallation targets using LBE as the target material, no release is observed within the limits of the experimental errors. At 867 K polonium evaporates slowly with an evaporation rate of the order of 1% per day. Even at temperatures as high as 968 K it takes about 12 days to remove 85% of the present polonium. Therefore, a large concentration of polonium in the cover-gas system of a LBE spallation target due to evaporation processes seems unlikely. However, for such a system the release of polonium by other processes like sputtering or the formation of aerosols and dusts has to be taken into account as well.

A comparison of tellurium and polonium release from LBE in an Ar/7%-$H_2$ atmosphere at 968 K is presented in FIG. 6. As already indicated by the results of short-term experiments the evaporation of Te from LBE is significantly slower than Po-evaporation.

In general, the results of long-term experiments show that the mechanism of the evaporation process does not change over long periods of time, i.e. no change of the reaction path is indicated. For the time dependency an approximate linear relation to the square root of release time is observed (FIG. 7) as generally known for release processes.

To assign or exclude possible reaction pathways the inventors evaluated some thermochemical properties of the main species that might be involved in such an evaporation process. The main gas phase species considered are monoatomic chalcogens Q, diatomic $Q_2$ molecules, dioxides $QO_2$, hydrides $H_2Q$, hydroxides $Q(OH)_2$ and the gaseous diatomic molecules PbQ and BiQ (Q=Se, Te, Po). From these species, the dioxides can be excluded because they will be reduced in the presence of hydrogen and metals such as lead. Equilibrium constants calculated from thermodynamic data [Barin, I.: *Thermochemical Data of Pure Substances*, VCH, Weinheim, 1995] for reactions such as $$QO_2+2H_2 \leftrightarrows Q+2H_2O \quad (3)$$

and $$QO_2+2Pb \leftrightarrows 2PbO+Q \quad (4)$$

indicate that the equilibrium is clearly dominated by the product side. This tendency is additionally increased by a stabilizing metal-chalcogen interaction ("coupled reduction") in solution [Neuhausen, J., Eichler, B.: Extension of Miedema's Macroscopic Atom Model to the Elements of Group 16 (O, S, Se, Te, Po), PSI-Report 03-13, Paul Scherrer Institute, Villigen, Switzerland, September 2003].

Thermodynamic data for reactions of metal chalcogenides with hydrogen and water such as $$PbQ+H_2 \leftrightarrows Pb+H_2Q \quad (5)$$

and $$PbQ+H_2O \leftrightarrows PbO+H_2Q \quad (6)$$

show that the formation of chalcogen hydrides is not favoured. Experimental investigations indicate that polonium hydride is thermally unstable. It is possibly formed only under the presence of nascent hydrogen [Gmelin's Handbook of Inorganic and Organometallic Chemistry, 8th Edition, Polonium, Supplement Vol 1, Springer-Verlag, Berlin, 1990, p. 421]. Within this work the inventors focus on monoatomic and diatomic chalcogens and diatomic lead and bismuth chalcogenides as gas phase species. For the volatilisation process the following pathways have to be considered:

1) evaporation of the chalcogen Q from LBE in form of single atoms according to $$Q(solv) \rightarrow Q(g) \quad (7)$$

Approximate values for the accompanying enthalpy of evaporation can be calculated by subtracting the partial molar enthalpy of solution of the chalcogen in the liquid metal $\Delta\overline{H}^{solv}_{Q\ in\ metal(l)}$ from the difference of the standard enthalpy of the gaseous monoatomic chalcogen ΔH Q(g) and its enthalpy of melting $\Delta H_m Q$:

$$\Delta\overline{H}^{v}_{Q}=(\Delta HQ(g)-\Delta H_m Q)-\Delta\overline{H}^{solv}_{Q\ in\ metal(l)} \quad (8)$$

Temperature dependency has been neglected and the enthalpy of melting at the melting point has been used as an approximation for $\Delta H_m Q$.

2) evaporation as diatomic chalcogen molecules according to $$2Q(solv) \rightarrow Q_2(g) \quad (9)$$

In analogy to monoatomic evaporation the enthalpy for this process can be expressed as the difference between standard enthalpy of the gaseous diatomic chalcogen minus twice the melting enthalpy of the chalcogen and the enthalpy associated with the solution of two atoms of Q in the liquid metal, hence:

$$\Delta\overline{H}^{v}_{Q_2}=(\Delta HQ_2(g)-2\Delta H_m Q)-2\Delta\overline{H}^{solv}_{Q\ in\ metal(l)} \quad (10)$$

3) evaporation in form of diatomic metal chalcogenides MQ (M=Pb, Bi; Q=Se, Te, Po)

$$Q(solv)+M(1) \rightarrow MQ(g) \quad (11)$$

The associated enthalpy can be calculated from the enthalpy values of the monoatomic species M and Q, their enthalpies of melting, the partial molar enthalpy of solution of the chalcogen Q in the liquid metal M and the dissociation enthalpy of the diatomic molecules MQ using the following equation:

$$\Delta\overline{H}_{MQ}=(\Delta HQ(g)-\Delta H_m Q)+(\Delta HM(g)-\Delta H_m M)-\Delta\overline{H}^{solv}_{Q\ in\ metal(l)}-\Delta H^{diss}MQ(g) \quad (12)$$

The inventors have calculated enthalpies of evaporation for these processes using available thermochemical data for ΔHQ(g), ΔHM(g), $\Delta H_m Q$, $\Delta H_m M$ and $\Delta HQ_2(g)$ from [Barin, I.: *Thermochemical Data of Pure Substances*, VCH, Weinheim, 1995] (Se, Te) and [Eichler, B.: Die Flüchtigkeitseigenschaften des Poloniums, PSI-Report 02-12, Paul Scherrer Institute, Villigen, Switzerland, June 2002] (Po). Values for $\Delta\overline{H}^{solv}_{Q\ in\ metal(l)}$ have been calculated using Miedema's Macroscopic Atom Model [de Boer, F. R., Boom, R., Mattens, W. C. M., Miedema, A. R., Niessen, A. K.: *Cohesion in Metals, Transition Metal Alloys*, North-Holland, Amsterdam 1988]. Details of the parameterisation of the model and the calculation procedure can be found in [Neuhausen, J., Eichler, B.: Extension of Miedema's Macroscopic Atom Model to the Elements of Group 16 (O, S, Se, Te, Po), PSI-Report 03-13, Paul Scherrer Institute, Villigen, Switzerland, September 2003]. The values for $\Delta\overline{H}^{solv}_{Q\ in\ metal(l)}$ calculated in this way are very similar for the chalcogens in liquid Pb and Bi, respectively. Furthermore, LBE does not deviate to far from ideal behaviour. Therefore, the inventors give mean values for $\Delta\overline{H}^{solv}_{Q\ in\ metal(l)}$ calculated for lead and bismuth below.

Values for the dissociation enthalpies of diatomic molecules $\Delta H^{diss}MQ(g)$ are estimated using a method described in [Miedema, A. R., Gingerich, K. A.: On the enthalpy of formation of diatomic intermetallic molecules. J. Phys. B:

*Atom. Molec. Phys*. Vol. 12, 2255, (1979)]. The values for dissociation enthalpies of homonuclear diatomic molecules $M_2$ and $Q_2$ required for these calculations have been taken from [Barin, I.: *Thermochemical Data of Pure Substances*, VCH, Weinheim, 1995, Eichler, B.: Die Flüchtigkeitseigenschaften des Poloniums, PSI-Report 02-12, Paul Scherrer Institute, Villigen, Switzerland, June 2002].

The results of these calculations are compiled in Table 1. From these values it can be concluded that evaporation of chalcogens from LBE in the form of lead chalcogenide molecules seems to be the least probable reaction path from a thermochemical point of view. For a discussion on the remaining possibilities the inventors discuss the release process as three possible series of successive reactions as shown in FIG. 8.

For each of these reaction sequences the rate of release and hence the observed sequence of release rates (experimentally: Se<Te<Po) will be determined by the reaction step involving the highest energy of activation. Thus, if the release process is diffusion controlled the sequence of release rates will be determined by the sequence of activation energies of diffusion. Nevertheless, the actual species released could still be either of the three possibilities Q, $Q_2$ or MQ. No literature data are available for diffusion of chalcogens in LBE. Therefore, the inventors have to rely on estimations for evaluating the corresponding activation energies. The energy of activation for the process of self-diffusion in liquid lead is 18.6 kJ/mole [Leymonie, C.: *Radioactive Tracers in Physical Metallurgy*, Chapman and Hall, London 1963, p. 112]. For diffusion of lead and bismuth in LBE activation energies of 9.6 and 7.7 kJ/mole, respectively, have been estimated from molecular dynamics calculations [Celino, M. Conversano, R., Rosato, V.: Atomistic simulation of liquid lead and lead-bismuth eutectic. *J. Nucl. Materials* 301, 64 (2002).]. Experimental values vary in the range from 11.6 to 40 kJ/mole [Landolt-Börnstein Zahlenwerte und Funktionen aus Physik, Chemie, Astronomie, Geophysik und Technik, 6. Auflage, II. Band, 5. Teil B, Springer, Berlin 1968]. For diffusion of selenium in liquid tin an activation energy of 13.4 kJ/mole has been determined [Landolt-Börnstein Zahlenwerte und Funktionen aus Physik, Chemie, Astronomie, Geophysik und Technik, 6. Auflage, II. Band, 5. Teil B, Springer, Berlin 1968]. Assuming similar or even somewhat larger values for chalcogen diffusion in LBE it still seems unlikely that diffusion is the rate determining step since activation energies for the evaporation step are expected to be in the order of magnitude of the enthalpies of evaporation compiled in Table 1.

The enthalpy values for the evaporation of monoatomic chalcogens are in agreement with the experimentally observed sequence of evaporation rates. Assuming that the corresponding activation energy values are similar, this could be interpreted as a supporting fact for the release in the form of monoatomic chalcogens. However, if there is a high enough concentration of chalcogen in the liquid alloy to facilitate the formation of $Q_2$ molecules, the evaporation in form of $Q_2$ species should be favoured compared to the release as monoatomic chalcogens. This has to be mainly taken into account for selenium and tellurium. Chemical analysis of the LBE used in the inventor's experiments show that the concentration of these elements are below the detection limits (<2 ppm, ICP-OES), but still these elements can be present as inactive impurities with much higher concentrations than those of the radioactive tracer determined by γ-ray spectroscopy. Polonium however is present in the inventor's samples in a carrier-free state. Therefore, the formation of $Po_2$ is very unlikely. Considering the approximate character of the inventor's calculations the evaporation in form of BiQ molecules is possible as well. In particular, relatively small values for the enthalpies of evaporation of BiQ have been calculated for Q=Se and Po. Thus, no certain decision can be made based on the results of the inventor's calculations. Finally, it is also possible that the release process for selenium, tellurium and polonium is not identical. Definitely, the evaporation in form of BiQ molecules is much more likely than evaporation as PbQ.

For further clarification of the reaction pathway, concentration dependent evaporation experiments should be performed to investigate $Q/Q_2$-problem. For selenium and tellurium this can be achieved by the addition of inactive chalcogen as a carrier, which also reflects the operating conditions of a LBE spallation target, i.e. higher concentrations of spallation products.

Furthermore, larger scale experiments in a flow system with varying gas phase composition and with the addition of suitable representatives for spallation products would be useful to establish a deeper understanding of the processes occurring in such a target. The interaction of polonium with other spallation products such as electropositive metals will most likely lead to a decrease of its evaporation rate [Neuhausen, J., Eichler, B.: Extension of Miedema's Macroscopic Atom Model to the Elements of Group 16 (O, S, Se, Te, Po), PSI-Report 03-13, Paul Scherrer Institute, Villigen, Switzerland, September 2003].

Finally, a study of segregation effects of polonium in solid LBE is of interest with respect to the storage of a spallation target after decommissioning. Given the fact that LBE melts at 398 K relatively high diffusion rates can be expected within the target material after freezing and decommissioning. Results of calculations of approximate partial molar enthalpies of segregation of polonium in lead and bismuth [Neuhausen, J., Eichler, B.: Extension of Miedema's Macroscopic Atom Model to the Elements of Group 16 (O, S, Se, Te, Po), PSI-Report 03-13, Paul Scherrer Institute, Villigen, Switzerland, September 2003] indicate that a segregation of chalcogens in solid lead and bismuth is not highly probable, but cannot be ruled out as well. Indeed, in the inventor's evaporation experiments the inventors have observed small segregation effects for the selenium samples that manifested themselves in the count rates of the lowest energy γ-lines (as a consequence, these lines were excluded from release evaluations).

2. Preferred Aspect: Volatile Elements Production Rates in a 1.4 GeV Proton-Irradiated Molten Pb—Bi Target In a second preferred aspect of the present invention, the invention relates to volatile elements production rates in a 1.4 GeV proton-irradiated molten lead-bismuth target a. Introduction Production rates of volatile elements following spallation reaction of 1.4 GeV protons on a liquid Pb/Bi target have been measured. The experiment was performed at the ISOLDE facility at CERN. These data are of interest for the developments of targets for accelerator driven systems such as MEGAPIE. Additional data have been taken on a liquid Pb target. Calculations were performed using the FLUKA and MCNPX Monte Carlo codes coupled with the evolution codes ORIHET3 and FISPACT using different options for the intra-nuclear cascades and evaporation models. Preliminary results from the data analysis show good comparison with calculations for Hg and for noble gases. For other elements such as I it is apparent that only a fraction of the produced isotopes is released. The agreement with the experimental data varies depending on the model combination used. The best results are obtained using MCNPX with the INCL4/ABLA models and with FLUKA. Discrepancies are found for some isotopes produced by fission using the MCNPX with the Bertini intranuclear cascade model coupled with the Dresner evaporation model.

In the development of key experiments in the frame of the research on Accelerator Driven System (ADS) for the nuclear waste transmutation (The European Technical Working Group on ADS, *A European Roadmap for Developing Accelerator Driven Systems (ADS) for Nuclear Waste Incineration*, ENEA, Roma, 2001), many issues arise which require dedicated experiments. One example is the development of an ADS target, where the isotope production following the interaction of an intense proton beam with a liquid target is of fundamental importance for safety reasons. In the European roadmap for developing accelerator driven systems for nuclear waste incineration, the key experiment for the target development is MEGAPIE (G. S. Bauer, et al., *Journal of Nuclear Materials* 296, 17 (2001).).

The aim of the MEGAPIE (MEGAWatt PIlot Experiment) project is to demonstrate the feasibility of a liquid lead bismuth eutectic (LBE) target for spallation facilities at a beam power level of about 1 MW. During the design phase of such an innovative system, many safety aspects must be considered. One of them concerns the production of volatile elements during operation. This is important for several reasons: i) some stable gases, and in particular $^{4}$He and H, are expected to be produced in relatively large quantity (in the case of MEGAPIE, about 1 liter NTP per month) and a system must be designed to handle safely the gases and avoid excessive pressure buildups. Moreover, it is important to know the production of these light elements to estimate possible damage to structural materials. ii) the production of radioactive elements is of concern for safety reason. The long-lived elements are of major concern, but short-lived elements are also of interest in case of an accident.

In the last years a great research effort was devoted in basic nuclear studies of interest for ADS (accelerator driven systems) applications. This has resulted in a renovated interest in the study of isotope production following spallation reactions in heavy materials (Yu. E. Titarenko et al., *Phys. Rev. C* 65, 064610 (2002), R. Michel et al., *Nucl Instrum. Methods B* 129, 153 (1997).). Experiments performed in inverse kinematics have allowed the investigation over large mass regions of production cross sections in thin targets (T. Enqvist et al., *Nucl. Phys. A* 686, 481 (2001).). These experiments, in combination with the further development of Monte Carlo transport codes, have led to a deeper understanding of the spallation process and to the development of new theoretical models (A. Boudard et al., *Phys. Rev. C* 66, 044615 (2002).).

In the case of an ADS target, where production of isotopes originates in a large volume of LBE, it is important to consider not only the production of volatile elements, but also their release rate out of the LBE volume. In the case of MEGAPIE, a cover gas system has been designed to properly handle the gas produced (W. Wagner et al., in *Proceedings of the MEGAPIE Technical Review Meeting*, Nantes, France 2004). A verification of the production rates estimated by the codes used during the design of the cover gas system is therefore important.

The inventors chose to perform a dedicated experiment to study the production rates of stable and radioactive volatile elements in a LBE target irradiated by a proton beam of the energy of the order of the energy of the SINQ synchrotron (590 MeV).

For a suitable experimental setup, see Example 2.

A selection of the data is presented in this invention, with emphasis on the γ-spectroscopy data.

Online Measurements

The time-dependent releases of volatile elements were measured with the online measuring techniques of the tape station and the Faraday cup. Release curves of volatile elements have specific shapes typical for each element; in most of the cases the decay part can be fitted with the sum of two exponentials (U. Köster, *Ausbeuten und Spektroskopie radioaktiver Isotope bei LOHENGRIN und ISOLDE*, PhD thesis, Technische Universität München, and references therein (2000).).

The online measurement with the tape station allows correction for partial decay of produced isotopes inside the target, before the release. In fact, since the release is dependent on the chemical properties of a given element, it is possible for instance to fit the release functions of $^{6}$He (measured with the tape station) and $^{4}$He (measured with the Faraday cup) and correct for the partial decay of the $^{6}$He.

During the first measurement, with the LBE target, it was found that the short term component exhibited discontinuities probably related to splashing effects in the target which reduced for a few tens of ms the ionization efficiency of the ion source. While this affects only slightly the absolute release, which is dominated by the long component, it makes it more difficult to fit the release curve. No such effect was observed during the second measurement, with the Pb target, where the proton beam intensity was reduced to $1.5\times10^{12}$ protons/pulse.

In FIG. 9 the $^{4}$He current measured by a Faraday cup for 6 s after the arrival of the proton beam on the Pb target is shown.

The ionization and transmission efficiency from the ion source to the Faraday cup was measured to be 0.05% for $^{3}$He. Assuming the same transmission efficiency for $^{4}$He, the production rate for $^{4}$He is 0.77 atoms/p, with a systematic uncertainty of about 20%. This value is in good agreement with calculations with MCNPX with the Bertini/Dresner models, giving 0.84 atoms/p.

Offline Measurements

Collection measurements were performed for a number of isotopes. The inventors investigated the release of Ne, Ar, Kr, Xe, Br, Cd, Te, I, Hg, Po, and At radioisotopes. During the first measurement run more attention was concentrated on those isotopes which are critical for the operation of an ADS target such as MEGAPIE.

For a given isotope, the measured yield has two components, one from direct production from the target and one from the decay of parents. Isotopes were collected in an order chosen so that the first ones to be measured were the first reaching equilibrium, having parents with shorter half-lives. In this way most of the measured isotopes were in equilibrium with their parents, with only a few exceptions.

In FIG. 10 the measured cumulative production rates for radioactive Hg isotopes are presented. Longer-lived Hg isotopes are expected to be completely released at the temperature of 600° C. The ionization efficiency was not measured for Hg, as it was only measured for noble gases. In this case only indicative results can be extracted: based on previous results from R. Kirchner (*Nucl. Instrum. Methods B* 126, 125 (1996)), the inventors considered an efficiency of a factor 1.5 higher than the measured Xe efficiency of 3.7(11) %.

The measured values are in line with expected cumulative production rates calculated using the Monte Carlo transport codes FLUKA (A. Fassò et al., in Proceedings of the Monte Carlo 2000 conference, Lisbon, A. Kling, F. Barao, M. Nakagawa, L. Tavora, P. Vaz eds., Sprinter-Verlag Berlin, p. 159

(2001)) and MCNPX (L. S. Waters et al., *MCNPX Users's Manual Version* 2.4.0, LA-CP-02-408 (2002).). The two codes were coupled with the evolution codes ORIHET3 (F. Atchison and H. Schaal, *Orihet* 3—*Version* 1.12, *A guide for users*, March 2001) and SP-FISPACT (C. Petrovich, SP-FISPACT, *A computer code for activation and decay calculations for intermediate energies. A connection of FISPACT and MCNPX*, RT/ERG/2001/10, ENEA, Bologna (2001).), respectively. In the case of MCNPX, results are shown here with two different model combinations for the intranuclear cascade and evaporation models. The circles represent results from using the Bertini intranuclear cascade model with the Dresner evaporation code. The diamonds are obtained using the recently implemented INCL4/ABLA (A. Boudard et al., *Phys. Rev. C* 66, 044615 (2002).) model combination. The trend observed in the data as a function of the atomic mass is well reproduced by the three calculations. One should note that for $^{193}$Hg, $^{195}$Hg and $^{197}$Hg, there are isomeric states of 11.1 h, 40 h and 23.8 h half-lives, respectively. For these three isotopes, equilibrium was not achieved between formation and decay of the respective isomeric states, a process which is difficult to properly calculate with existing Monte Carlo codes. Overall these results confirm the expected production rates of Hg isotopes in a thick LBE target.

Results for Xe isotopes, also measured with the LBE target at T=600° C., are shown in FIG. 11. In this case there is a clear disagreement between the values calculated with MCNPX with Bertini/Dresner, and the results from the other two calculations. The data, with an ionization efficiency of 3.7% for Xe isotopes seem to favor the other two calculation results, thus confirming recent experimental findings (T. Enqvist et al., *Nucl. Phys. A* 686, 481 (2001).).

Similar results are obtained for the iodine isotopes. However, I is not completely released and observed production rates at 600° C. are a factor 10 lower than the calculated FLUKA and MCNPX (INCL4/ABLA) values.

While production of Hg isotopes from Pb/Bi target is due to direct spallation, the Xe and I isotopes are the results from a later stage of the spallation process, the fission of highly excited spallation fragments, or as a two-step process due to neutron induced fission from high energy spallation neutrons. Thus the evaporation models, the Dresner and ABLA, are probably most responsible for the differences observed in the calculations.

Among the other isotopes measured, it is of particular interest to discuss the Po and At. Production rates of $^{207,208,209,210}$At of the order of $10^7$ atoms/μC (assuming the same ionization efficiency as for Hg) were detected, with values an order of magnitude lower for $^{206}$At. Such production rates are not of concern for an ADS. On the other hand, it is the first observation of At beam from a Pb/Bi target and this constitutes an interesting result with possible applications. Production of At comes from several possible reactions of Bi, but the most likely, given the high proton energy, is $^{209}$Bi(p, π xn)$^{210-x}$At. The At decay is responsible for the observed small quantities of Po isotopes, which contrary to At is expected to be produced in large amounts. However, as found in Ref. 15, little or no Po should be released at 600° C.

Of the other isotopes measured in the first measurement, no release of Br was observed, while very little amounts of Cd isotopes were detected. For the Kr isotopes, some problems during the measurement rendered the analysis questionable and such measurement was repeated with the Pb target.

b. Conclusions

The first results from the measurements of production rates of volatile elements from irradiated LBE and Pb targets indicate that the results are consistent with the expectations from Monte Carlo calculations. Overall, these preliminary results confirm the expected production rates in an ADS target such as MEGAPIE, and therefore help in positively assessing such calculations, and the system designed to handle the released volatile elements.

3. Preferred Aspect: In Vivo TAT Application using $^{149}$Tb-Rituximab

In a third preferred aspect of the present invention, the invention relates to targeted alpha therapy (TAT) in vivo, showing direct evidence for single cancer cell kill using $^{149}$Tb-Rituximab.

a. Introduction

This part of the present invention demonstrates high efficiency sterilization of single cancer cells in a SCID mouse model of leukemia using Rituximab, a monoclonal antibody that targets CD20, labeled with 149-Terbium, an alpha-emitting radioisotope. Radioimmunotherapy with 5.5 MBq labeled antibody conjugate (1.11 GBq/mg) 2 days after an intravenous graft of $5\cdot10^6$ Daudi cells resulted in tumor free survival for >120 days in 89% of treated animals. In contrast, all control mice (no treatment or treated with 5 and 300 μg unlabeled Rituximab) developed lymphoma disease. At the end of the study period, 28.4±4% of the long-lived daughter activity remained in the body, out of which 91.1% was located in bone tissue and 6.3% in the liver. A relatively high daughter radioactivity concentration was found in the spleen (12±2%/g), suggesting that the killed cancer cells are mainly eliminated through the spleen. This promising preliminary in vivo study suggests that TAT with $^{149}$Tb is worthy of consideration as a new generation radioimmunotherapeutic approach.

Single cancer cells in circulation and small cancer cell clusters can be effectively targeted with radio-immunoconjugates that specifically bind to the cells and deliver the required dose. Alpha-emitting radioisotopes may be of great advantage in this kind of therapy because of their higher linear energy transfer (LET) value and consequently, the shorter penetration track compared to $\beta^-$- and γ-radiation [Hall E J. Radiobiology for the Radiologist. 4th ed. Philadelphia: Lippincott J B Comp 1994]. It has been shown that only a very few alpha-hits are sufficient to kill a cell [Maecklis R M, Lin J Y, Beresford B, Achter R W, Hines J J, Humm J L. Cellular kinetics, dosimetry, and radiobiology of alpha-particle radioimmunotherapy: inducing of apoptosis. *Radiat Res.* 1992; 130:220-226], and the short range of the alpha particles increases the safety profile of alpha-emitters because nonspecific irradiation of normal tissue (or plasma) around the target cells is greatly reduced or absent [McDevitt M R, Ma D, Simon J, Frank R K and Scheinberg D. Design of $^{225}$Ac-radiopharmaceuticals. *Appl Rad Isot.* 2002; 57:841-847]. Additionally, since single cancer cells in circulation are immediately accessible to the injected (i.v.) radioimmunoconjugate, the shorter half-lives of a few α-emitting radioisotopes may be advantageous [Allen B J, Blagojevic N. Alpha and beta emitting radiolanthanides in targeted cancer therapy: the potential role for Terbium-149. *Nucl Med Commun* 1996; 17:40-47]. Only few R-emitting radionuclides fulfill the requirements for this specific nuclear medical application: $^{255}$Fm, $^{225}$Ac, $^{224}$Ra, $^{223}$Ra, $^{213}$Bi, $^{212}$Bi, $^{211}$At and $^{149}$Tb. Especially the $^{213}$Bi and $^{211}$At have proven to be very promising candidates, because of the availability ($^{225}$Ac/$^{213}$Bi generator) and the convenient half-life of 7.2 h ($^{211}$At) (for example see Zalutsky M R, Vaidyanathan G. Astatine-211 labeled radiotherapeuticals: an emerging approach to targeted alpha particle therapy. *Current Pharm Design* 2000; 6:1433-1455, Huber R, Seidl C, Schmid E, Seidenschwang S, Becker K-F, Schuhmacher C, Apostolidis C, Nikula T, Kremmer E, Schwaiger M, Senekowitsch-Schmidtke. Locoregional alpha-radioimmunotherapy of intraperitoneal tumor celldissemination using a tumor-specific monoclonal antibody. *Clinical Cancer Research* 2003; 9:3922-3928]).

Today, new approaches in conjugation with chelating ligands allow the stable labeling of macromolecules (such as monoclonal antibodies) or peptides with metallic radionuclides. The first clinical proof-of-principle of targeted alpha therapy was observed using the HuM195 antibody labeled with the short-lived (46 min) $^{213}$Bi radionuclide [Jurcic J G, Larson S M, Sgouros G, McDevitt M R, Finn R D, Divgi C R, Ballangrud Å M, Hamacher K A, Ma D, Humm J L, Brechbiel M W, Molinet R, Scheinberg D A. Targeted alpha-particle immunotherapy for myeloid leukemia. *BLOOD* 2002; 100: 1233-1239], which is a daughter product in the decay chain of $^{225}$Ac (10 d). The mother nuclide, $^{225}$Ac, is itself considered as candidate for TAT, and corresponding studies are ongoing [McDevitt M R, Ma D, Simon J, Frank R K and Scheinberg D. Design of $^{225}$Ac-radiopharmaceuticals. *Appl Rad Isot.* 2002; 57:841-847, McDevitt M R, Sgouros G, Finn R D, Humm J L, Jurcic J G, Larson S M, Scheinberg D A. Radioimmunotherapy with alpha-emitting radionuclides. *Eur J Nucl Med* 1998; 25:1341-1351]. A potential drawback with use of $^{225}$Ac is the possibility that the short-lived alpha-emitting daughter nuclides in the decay chain will escape from the place of origin, leading to uncontrolled deposition of the radiation dose throughout the body.

The partial alpha-emitting nuclide $^{149}$Th ($T_{1/2}$=4.118 h, $E_\alpha$=3967 keV, range in tissue=28 μm), which belongs to the group of rare earth elements, has been proposed as a promising alpha-emitter for targeted alpha therapy (TAT) [Allen B J, Blagojevic N. Alpha and beta emitting radiolanthanides in targeted cancer therapy: the potential role for Terbium-149. *Nucl Med Commun* 1996; 17:40-47, Allen B J, Goozee G, Imam S, Sarkar S, Leigh J, Beyer G-J. Targeted cancer therapy: The potential role of terbium-149. 6th International Conference on Radiopharmaceutical Dosimetry, Gatlington, Tenn. (USA), May 7-10, 1996, CERN-PPE/96-127, 1996; Charlton D E, Utteridge T D, Allen B J. Theoretical treatment of human hemopoietic stem cell survival following irradiation by alpha particles. *Int J Radiat Biol* 1998; 74:111-118; Allen B J. Can alpha immunotherapy succeed where other modalities have failed? *Nucl Med Commun* 1999; 20:205-207]. Its chemical behaviour is very close to that of yttrium or lutetium, whose isotopes $^{90}$Y and $^{177}$Lu are currently the most predominant metallic radionuclides used in clinical radioimmunotherapy (RIT) [Wagner Jr H N, Wiseman G A. et al. Administration Guidelines for Radioimmunotherapy of Non-Hodgkin's Lymphoma with $^{90}$Y-Labeled Anti-CD20 Monoclonal Antibody. *J Nucl Med* 2002; 43:267-272]. Thus, existing approaches for labelling of chelated bioconjugates with these metallic radionuclides, as well as $^{166}$Ho, $^{153}$Sm, $^{213}$Bi or $^{225}$Ac, can be directly applied to $^{149}$Th. Previous in vitro studies have revealed certain advantages of $^{149}$Tb over $^{213}$Bi for treating single cells [Miederer M, Seidl C, Beyer G-J, Charlton D E, Vranješ-Durić S D, Čomor J J, Huber R, Nikula T, Apostolidis C, Schuhmacher C, Becker K-F, Senekowitsch-Schmidtke R. Comparison of the radiotoxicity of two alpha emitting immunoconjugates Terbium-149 and Bismuth-213 directed against a tumor-specific, exon 9 deleted (d9) E-cadherine adhesion protein. *Radiation Research* 2002; 159:612-620]. These advantages, which relate to the lower energy and higher LET of α-particles emitted by $^{149}$Tb, partially compensate for its lower alpha branching (17%, FIG. 12) [Vranješ S D, Miederer M, Čomor J J, Soloviev D, Beyer G-J and the ISOLDE collaboartion. Labeling of monoclonal antibodies with 149-Tb for targeted alpha therapy. *J Lab Comp Radiopharm* 2001; 44:718-720, Miederer M, Seidl C, Beyer G-J, Charlton D E, Vranješ-Durić S D, Čomor J J, Huber R, Nikula T, Apostolidis C, Schuhmacher C, Becker K-F, Senekowitsch-Schmidtke R. Comparison of the radiotoxicity of two alpha emitting immunoconjugates Terbium-149 and Bismuth-213 directed against a tumor-specific, exon 9 deleted (d9) E-cadherine adhesion protein. *Radiation Research* 2002; 159:612-620]. The longer half-life of $^{149}$Tb (4.12 h) compared to the $^{213}$Bi (46 min) represents a clear advantage, both at the level of bioconjugate preparation and administration to patients for tumor cell targeting. On the other hand, the fate of long-lived daughter products that appear during the decay of $^{149}$Tb would need to be considered carefully in the dosimetry (see FIG. 12.).

In this part of the present invention the inventors describe the first in vivo survival study using a $^{149}$Tb-based TAT approach in SCID (severe combined immuno-deficient) mice. SCID mice, being deficient in T and B cell immune defense, easily develop tumor masses after injection of cancer cells. Daudi cells, which are derived from a human Burkitt lymphoma, are one of several cell lines that can rapidly colonize these mice. Depending on the injection route, different tumor types can develop. As little as 100 injected (i.v.) Daudi cells are sufficient to kill SCID mice due to tumor development [Ghetie M A, Richardson J, Tucker T, Jones D, Uhr J W, Vitetta E S, Disseminated or localized growth of a human B-cell tumor (Daudi) in SCID mice. *Int J Cancer* 1990; 45:481-485]. Since Daudi cells express a high number of $CD_2O$ antigens Rituximab can target Daudi cells with high specificity. Thus, an early stage of this model, within three days of i.v. xenograft, before the formation of manifested tumor nodes, provides an ideal system to study the proposed advantages of $^{149}$Tb-based TAT.

The primary aim of this work was to examine the efficacy of $^{149}$Tb-labeled Rituximab to specifically kill circulating single cancer cells or small cell clusters in vivo. SCID mice following i.v. xenograft with Daudi cells represent a perfect model for leukemia [McDevitt M R, Ma D, Lai L T, Simon J, Borchardt P, Frank R K, Wu K, Pellegrini V, Curcio M J, Miederer M, Bander N H, Scheinberg D A. Tumor therapy with targeted atomic nanogenerators. *Science* 2001; 294 (5546):1537-40]. The inventor's experimental model involves TAT intervention within three days of i.v. xenograft, and hence before the formation of manifested tumor nodes, which the inventors did not intend to target in this study. According to the inventor's experimental hypothesis, mice xenotransplanted with a lethal number of Daudi cells will survive provided that a sufficient dose of $^{149}$Th was delivered via Rituximab to all tumor cells. Secondly, the inventors aimed to obtain information about the behavior of the daughter products generally formed in the radioactive decay chain. The 17% alpha decay mode of the $^{149}$Tb generates an isobar chain with the mass number A=145 with $^{145}$Eu ($T_{1/2}$=5.93 d), $^{145}$Sm ($T_{1/2}$=340 d) and $^{145}$Pm ($T_{1/2}$=17.7 a). The EC-process decay chain of $^{149}$Tb forms the stable $^{149}$Sm passing the $^{149}$Gd ($T_{1/2}$=9.25 d) and the $^{149}$Eu ($T_{1/2}$=93.1d) ([Firestone R B. Table of Isotopes. Eight Edition, New York: Wiley-Interscience, 1996], see FIG. 12). Most of these isotopes are easily detectable using high-resolution gamma spectroscopic techniques (see FIG. 12). In particular the inventors expected that differences in daughter isotope behaviour induced by the different decay modes (alpha versus EC) would be apparent.

For suitable materials and methods as well as results obtained applying them, see e.g. Example 3.

b. Discussion

Protection of Mice Treated with Labeled Rituximab

Here the inventors show that TAT with Rituximab labeled with the high purity alpha emitting radio-lanthanide $^{149}$Tb led to almost complete protection of xenografted mice over four months without detectable signs of toxicity, under conditions where all animals in the control groups had to be sacrificed during the observation period due to the development of tumor diseases. The efficacy of the radionuclide bioconjugate as opposed to the unconjugated tumor targeting antibody alone is underlined by the complete lack of protection in the control group which received 5 μg unlabeled Rituximab per animal, and the relatively poor protection afforded by the higher dose unlabeled Rituximab group (300 μg per animal). The degree of protection afforded by the $^{149}$Tb-labeled Rituximab indicates that TAT with $^{149}$Tb is, on the basis of its efficacy, worthy of further consideration as a novel radioimmunotherapeutic strategy.

Biodistribution of Label and Decay Products

From earlier studies the inventors have learnt that once the lanthanides are trapped in a tissue, like liver or bone, they are fixed quite stably [Beyer G-J, Offord R E, Künzi G, Jones R M L, Ravn U, Aleksandrova Y, Werlen R C, Mäcke H, Lindroos M, Jahn S, Tengblad O and the ISOLDE Collaboration. Biokinetics of monoclonal antibodies labeled with radio-lanthanides and 225-Ac in xenografted nude mice. *J Label Conzpd Radiopharm* 1995; 37:229-530, Beyer G-J, Münze R, Fromm W D, Franke W G, Henke E, Khalkin V A, Lebedev N A. Spallation produced 167-Tm for medical application. In: Medical Radionuclide Imaging 1980, Vienna: IAEA, 1981, Vol. 1, p. 587 (IAEA-SM-247/60) 1981]. The blood clearance for free radio-lanthanides or radiolanthanides injected in solutions containing chelate ligands (citrate, EDTMP, NTA, EDTA, DTPA and others) is fast (half-time <1 h) [Beyer G-J, Münze R, Fromm W D, Franke W G, Henke E, Khalkin V A, Lebedev N A. Spallation produced 167-Tm for medical application. In: Medical Radionuclide Imaging 1980, Vienna: IAEA, 1981, Vol. 1, p. 587 (IAEA-SM-247/60) 1981, Beyer G-J, Offord R, Künzi G, Aleksandrova Y, Ravn U, Jahn S, Backe J, Tengblad O, Lindroos M and the ISOLDE Collaboration. The influence of EDTMP-concentration on the biodistribution of radio-lanthanides and $^{225}$Ac in tumor bearing mice. *Nuclear Medicine and Biology* 1997; 24:367-372]. The radio-lanthanides are then present mainly in the bone matrix and the liver, with the liver uptake determined by the ionic radius of the lanthanide [Beyer G-J, Münze R, Fromm W D, Franke W G, Henke E, Khalkin V A, Lebedev N A. Spallation produced 167-Tm for medical application. In: Medical Radionuclide Imaging 1980, Vienna: IAEA, 1981, Vol. 1, p. 587 (IAEA-SM-247/60) 1981, Beyer G-J, Offord R, Künzi G, Aleksandrova Y, Ravn U, Jahn S, Backe J, Tengblad O, Lindroos M and the ISOLDE Collaboration. The influence of EDTMP-concentration on the biodistribution of radio-lanthanides and $^{225}$Ac in tumor bearing mice. *Nuclear Medicine and Biology* 1997; 24:367-372, Beyer G-J, Bergmann R, Schomäcker K, Rösch F, Schafer G, Kulikov E V, Novgorodov A F. Comparison of the Biodistribution of $^{225}$Ac and Radiolanthanides as Citrate Complexes. *Isotopenpraxis* 1990; 26:111-114]. In the case of macromolecules (like monoclonal antibodies) the blood clearance is slow (half-time ~1 day) [Beyer G-J, Offord R E, Künzi G, Jones R M L, Ravn U. Aleksandrova Y, Werlen R C, Mäcke H, Lindroos M, Jahn S, Tengblad O and the ISOLDE Collaboration. Biokinetics of monoclonal antibodies labeled with radio-lanthanides and 225-Ac in xenografted nude mice. *J Label Compd Radiopharm* 1995; 37:229-530]. Thus, most of the $^{149}$Tb will decay while the labeled bioconjugate is in circulation and the free daughter nuclides formed in the radioactive decay would follow the biodistribution known for free radiolanthanides. The biodistribution found 120 days after treatment corresponds to the distribution patterns known for the free radio-lanthanide: highest daughter nuclide accumulation in bone and liver (91.1% and 6.3% of the retained activity, respectively) [Beyer G-J, Münze R, Fromm W D, Franke W G, Henke E, Khalkin V A, Lebedev N A. Spallation produced 167-Tm for medical application. In: Medical Radionuclide Imaging 1980, Vienna: IAEA, 1981, Vol. 1, p. 587 (IAEA-SM-247/60) 1981, Beyer G-J, Offord R, Künzi G, Aleksandrova Y, Ravn U, Jahn S, Backe J, Tengblad O, Lindroos M and the ISOLDE Collaboration. The influence of EDTMP-concentration on the biodistribution of radio-lanthanides and $^{225}$Ac in tumor bearing mice. *Nuclear Medicine and Biology* 1997; 24:367-372]. The spleen shows a radioactivity concentration almost as high as bone and significantly higher compared to liver. The inventors interpret this result as evidence that the targeted and killed cancer cells are eliminated mainly through the spleen, where the remaining radioactive daughter atoms are then trapped.

The long-lived daughter products are formed along two main decay processes: the isobar chain with A=145 is generated via the alpha decay mode of the initial $^{149}$Th, while the isobar chain with A=149 is formed after the EC- or $\beta^+$-process. In case of an alpha decay the recoil energy of the $^{145}$Eu daughter nuclei (110 keV) exceeds significantly the chemical binding energy. Consequently, the original molecule, the antibody-construct, is destroyed and the daughter atom is initially stabilized as free $Eu^{3+}$ ion. In the case of the EC-decay mode, the bound rupture is induced due to the Auger electron emission forming free daughter species [Beyer G-J, Herrmann E and Khalkin V A. Chemical effects related to different radioctive decay processes of cerium isotopes chelated with different polyaminocarbonic acids Dubna: JINR P 12-7758, 1974. Beyer G-J, Hermann E. Chemical effects of nuclear transformations in lanthanide chelate complexes., in Proceedings of the COST Chemistry Action D18, Mid Term Evaluation Workshop on Lanthanide Chemistry for Diagnosis and Therapy, Heidelberg (Germany) Jul. 22-25, 2002, p. 26] with 100% efficiency. However, it cannot be assumed that the daughter species escapes from its place of origin; it could eventually be bound to other proteins in the immediate environment. Consequently, one may not necessarily expect identical behavior from daughter products generated in the two different pathways: alpha- or EC-process. Analysis of the γ-spectroscopic data revealed that there was no statistically significant difference in the ratio of retained $^{145}$Sm to $^{149}$Eu in the organs from that predicted by the branching ratio of $^{149}$Tb. Thus, the radioactive decay pathway does not influence the biodistribution or redistribution of the long-lived daughter lanthanides.

Extrapolation to Clinical Application

A preliminary dose estimation for patients injected with 5 GBq $^{149}$Tb-Rituximab was performed based on MIRDOSE 3.1 [Stabin M G. MIRDOSE: personal computer software for internal dose assessment in nuclear medicine. *J Nucl Med* 1996; 37:538-546]. Assuming total decay of $^{149}$Tb-Rituximab in circulation and 100% retention of daughter nuclides in the body with a bone uptake of 91%, the total equivalent dose to the bone marrow as the critical organ would be 540 mSv/5 GBq (108 mSv/GBq) (see also Table 4). $^{149}$Tb itself would contribute 66.7% of the bone marrow radiation dose (45.2% due to the alpha-radiation using an alpha-radiation weight factor of $W_R$=10) and 21.5% due to its gamma- and beta$^+$-radiation) while the daughter nuclides would contribute 33.3% only. The dose contribution from daughter nuclides estimated in this way represents a worst case estimation (assuming 100% retention), since only 28.4% of the long-lived daughter products were retained in mice 120 days p.i. Thus, injection of a potentially therapeutic activity, 5 GBq $^{149}$Tb- Rituximab in a 70 kg patient, would deliver a bone marrow radiation dose far below the critical level. This preliminary dose estimation is well compatible with considerations presented in the review by McDevitt et al. [McDevitt M R, Sgouros G, Finn R D, Humm J L, Jurcic J G, Larson S M, Scheinberg D A. Radioimmunotherapy with alpha-emitting radionuclides. *Eur J Nucl Med* 1998; 25:1341-1351].

For further reduction of the retention of the daughter nuclides one could apply single or multiple injections of chelating ligands like EDTA or DTPA during or shortly after the treatment. This approach is already practiced as a preventive action in treatments with $^{90}$Y- or $^{177}$Lu-DOTATOC [Beyer G-J, Ruth T J. The role of electromagnetic separators in the production of radiotracers for bio-medical research and nuclear medical applications. *NIM B* 2003; 204:694-700].

Time Constraints and Availability

Spallation reaction in combination with on line mass separator technology was used for the production of $^{149}$Tb for this study. The radiochemical separation and purification of the $^{149}$Th was relatively easy to perform in about 30 minutes in this specific case, since the inventors started from non-carrier added preparations. The final $^{149}$Tb preparation was obtained in very high purity and in a small volume, the labeling of the bioconjugate was fast (10 minutes) and almost quantitative. The administration of the preparation should be carried out as rapidly as possible after purification of the $^{149}$Tb, since levels of contamination with daughter nuclides will increase with time. For example, application of a fixed dose of the $^{149}$Tb-labeled bioconjugate 4 hours after the final purification of the isotope itself (EOS) leads to an increase of the long-lived daughter content by a factor of 2. According to the preliminary dose estimation one could define a shelf-life for the labelled $^{149}$Tb-labeled bioconjugate of about 4-6 hours. For a longer delay it would be advisable to repurify the $^{149}$Tb from the accumulated daughter products, a process that could be expected to require 30 minutes.

Several nuclear processes could be used to make this interesting alpha emitting isotope available on large scale: light particle (p, d, He) induced reactions on $^{152}$Gd as target material, heavy ion induced reactions on light lanthanide targets or spallation reaction on Ta as target [Beyer G-J, Čomor J J, Daković M, Soloviev D, Tamburella C, Hagebø E, Allan B, Dmitriev S N, Zaitseva N G, Starodub G Y, Molokanova L G, Vranješ S D, Miederer M and the ISOLDE Collaboration. Production routes of the alpha emitting 149-Tb for medical application. *Radiochim Acta* 2002; 90:247-252]. Off line and on line mass separation process may support a very high isotopic purity [Beyer G-J, Čomor J J, Daković M, Soloviev D, Tamburella C, Hagebø E, Allan B, Dmitriev S N, Zaitseva N G, Starodub G Y, Molokanova L G, Vranješ S D, Miederer M and the ISOLDE Collaboration. Production routes of the alpha emitting 149-Tb for medical application. *Radiochim Acta* 2002; 90:247-252, Beyer G-J, Ruth T J. The role of electromagnetic separators in the production of radiotracers for bio-medical research and nuclear medical applications. *NIM B* 2003; 204:694-700].

All the above-mentioned technologies are well-developed and available today. In summary, should $^{149}$Tb continue to show promise in further studies of TAT, then it would be technically feasible to make the isotope available in large-scale and on a routine basis.

EXAMPLES

Example 1

1. Experimental Setup

This experimental setup is e.g. suitable for the first preferred aspect of this invention.

Pieces of eutectic Pb/Bi-alloy (44.8 wt. % Pb, 55.2 wt. % Bi, Impag AG, Switzerland, impurities (ppm): Ag 11.4, Fe 0.78, Ni 0.42, Sn 13.3, Cd 2.89, Al 0.3, Cu 9.8, Zn 0.2, Se<2, Te<2) of dimensions approx. 10×10×1.5 mm$^3$ have been doped with $^{75}$Se, $^{121}$Te and $^{206}$Po by implantation of mass-separated radioactive ion beams at the on-line isotope separator ISOLDE at CERN.

$^{206}$Po was prepared indirectly, by implantation of the precursors $^{206}$Rn ($T_{1/2}$=2.7 min) and $^{210}$Fr ($T_{1/2}$=3.2 min) respectively. The $^{206}$Rn beams were produced by 1.4 GeV proton-induced spallation of a 50 g/cm$^2$ $^{238}UC_x$ target (x≈4) connected via a water-cooled transfer line to a FEBIAD ion source [U. Köster for the ISOLDE Collaboration: ISOLDE target and ion source chemistry. *Radiochimica Acta* 89, 749 (2001).]. The condensation of non-volatile isobars in the transfer line assures beams of high isotopic purity (>>99.9%). About 38% [Audi, G., Bersillon, O., Blachot, J. Wapstra, A. H.: The NUBASE evaluation of nuclear and decay properties. *Nuclear Physics A* 729, 3 (2003).] of the $^{206}$Rn decays via ($\beta^+$/EC)→$^{206}$At→($\beta^+$/EC) to $^{206}$Po, the remaining 62% populate $^{202g}$Pb and $^{198}$Pb/$^{198}$Tl, which do not contribute any measurable activity after some days of decay. The beam intensity was about $2\cdot10^8$ $^{206}Rn^+$ ions per s, allowing to collect 4 kBq $^{206}$Po per minute.

On another occasion a 50 g/cm$^2$ $^{238}UC_x$ target connected via a high temperature transfer line to a tungsten surface ionizer was used. All parts were kept above 2000° C. About 98% of the $^{210}$Fr decaus via EC/$\beta^+$→$^{210}$Rn→α→ or via α→$^{206}$At→EC/$\beta^+$→ to $^{206}$Po. Again the side branches of the decay chain do not contribute any measurable activity after some days of decay. The beam intensity of $^{210}$Fr of about $2\cdot10^8$ ions per s results in a production of 10 kBq $^{206}$Po per minute.

Also $^{121}$Te was produced indirectly by implantation of the precursors $^{121g+m}$Cs which decay by $\beta^+$/EC via $^{121}$Xe and $^{121}$I to $^{121}$Te. $^{121}$Cs was produced from the same $UC_x$ target as above by 1.4 GeV proton-induced spallation-fission and then surface ionised. Despite the unfavourable target and ion source combination (neutron-deficient nuclides are much better produced by spallation of a close-by target nucleus), a $^{121}$Cs beam intensity better than $3\cdot10^7$ ions per s allowed to collect about 1 kBq $^{121}$Te per minute.

$^{75}$Se was produced by 1.4 GeV proton-induced spallation of a 11 g/cm$^2$ zirconia fibre target connected via an unselective, hot transfer line to a FEBIAD ion source [Köster, U., Bergmann, U. C., Carminati, D., Catherall, R., Cederkäll, J., Correia, J. G., Crepieux, B., Dietrich, M., Elder, K., Fedoseyev, V. N., Fraile, L., Franchoo, S., Fynbo, H., Georg, U., Giles, T., Joinet, A., Jonsson, O. C., Kirchner, R., Lau, Ch., Lettry, J., Maier, H. J., Mishin, V. I., Oinonen, M., Peräjärvi, K., Ravn, H. L., Rinaldi, T., Santana-Leitner, M., Wahl, U., Weissman, L.: Oxide fiber targets at ISOLDE. *Nucl. Instr. Methods* B 204 (2003) 303]. The cumulative ion beam intensity of $^{75}Se^+$ plus precursors ($^{75}$Br, $^{75}$Kr, $^{75}$Rb) was about 5.108 ions per s, allowing to collect 2 kBq of $^{75}$Se within 1 minute.

The samples doped with $^{75}$Se, $^{121}$Te and $^{206}$Po were cut in pieces and afterwards melted and heated at 673 K for 1 hour together with additional LBE reduced under a hydrogen atmosphere to achieve homogeneous distribution of radionuclides as well as suitable sample sizes and activities suitable for measurement by γ-ray spectroscopy. No additional carrier was added.

For the long-term release studies LBE containing $^{205}Bi$ produced by neutron activation was used for diluting the samples in the same manner as described above. $^{205}Bi$ was used as an internal standard for the evaluation of γ-ray spectra to correct for changes in sample shape frequently occurring on melting. For short-term experiments $^{206}Bi$ produced by decay of $^{206}Po$ was used as standard.

The number of nuclei and concentrations of $^{75}Se$, $^{121}Te$ and $^{206}Po$ were determined from the peak areas of characteristic γ-rays of the respective nuclide ($^{75}Se$: 400.66 keV, $^{121}Te$: 573.14 keV, $^{206}Po$: 1032.26 keV) taking into account the detector efficiency and γ-branching [http://nucleardata.nuclear.lu.se/nucleardata/toi/]. Self-absorption effects were roughly estimated based on sample thickness and mass attenuation coefficients listed in [http://physics.nist.gov/PhysRefData/XrayMassCoef/tab3.html]. Estimated experimental errors of number of nuclei and concentrations are 40% for $^{75}Se$, 25% for $^{121}Te$ and 15% for $^{206}Po$ resulting mainly from the crude evaluation of self-absorption effects.

Typical numbers of nuclei were in the range of $4*10^8$ to $5*10^9$ for $^{121}Te$ and $^{206}Po$ containing LBE samples and $2*10^{10}$ to $5*10^{10}$ for 15Se containing LBE samples. Typical sample masses for short-term (1 hour) experiments were 2.5 g ($^{75}Se$ samples) and 0.13-0.88 g ($^{121}Te/^{206}Po$ samples), whereas for long term studies on the release of $^{121}Te$ and $^{206}Po$ larger samples (2.5-7.5 g) have been used. The resulting mole fractions at the start of the experiment were in the range of $3*10^{-13}$ to $2.5*10^{-12}$ for $^{121}Te/^{206}Po$ containing samples and 3.2 to $7.3*10^{-12}$ for $^{75}Se$ containing samples.

Figure 1C:
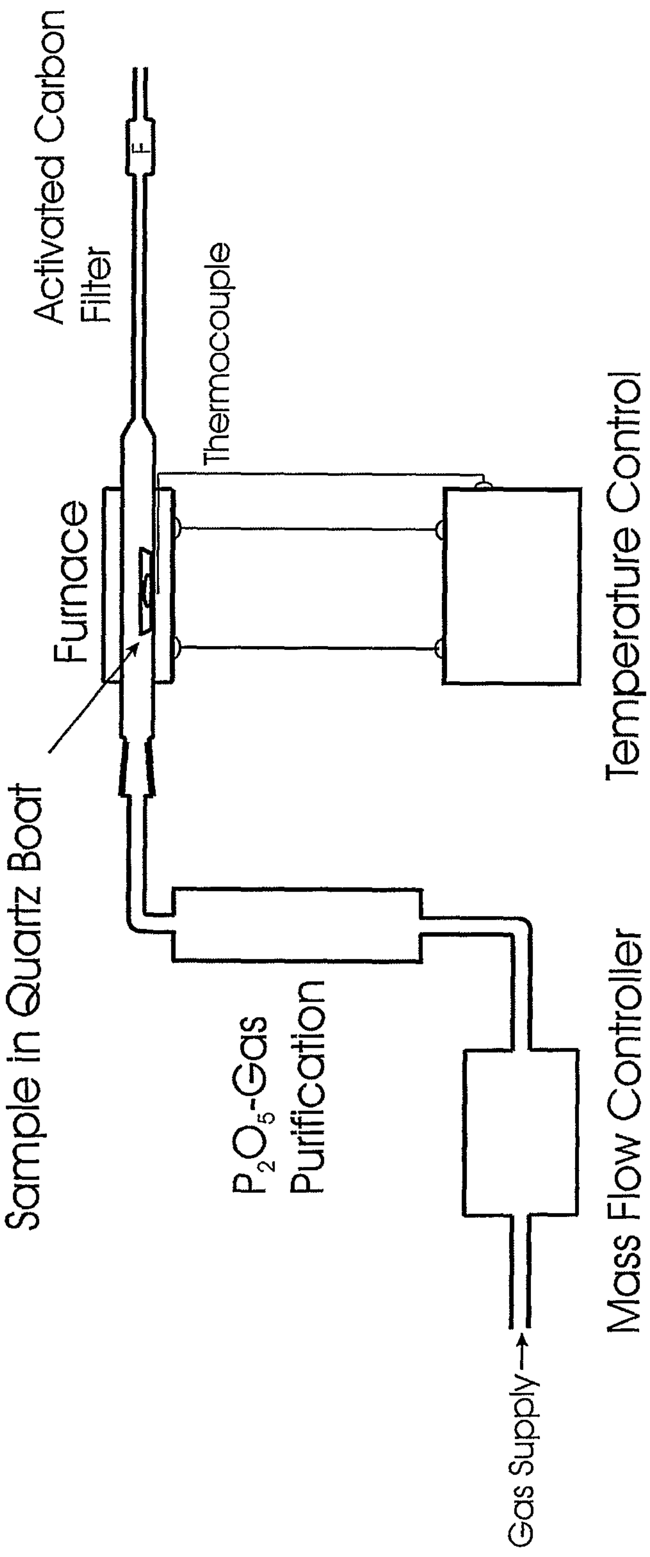
FIG. 1C shows schematic drawings of the experimental set-up of the first preferred aspect and Example 1.

Evaporation experiments (one experiment for each temperature setting) were performed using the experimental set-up illustrated in FIG. 1. Before the experiment, the samples were scratched to remove the surface oxide layer. The samples were then placed on a quartz tissue within a quartz boat, which was placed in a quartz tube. This tube was flushed with an Ar/7%-$H_2$ mixture (purity: $H_2$>99.993%, Ar>99.998%), which was previously run through a column containing a Pd-contact to facilitate the establishment of $O_2/H_2/H_2O$ equilibrium and Sicapent (with indicator, Merck, Germany) for removing moisture. A partial pressure of water of 3.7±1.7 hPa was determined using a Zr/$Y_2O_3$-solid electrolyte cell.

Some additional experiments were performed in a water saturated Ar atmosphere. For this, Ar (purity >99.998%) was bubbled though a washing bottle containing water at room temperature and the drying column was removed.

All experiments were performed using a continuous gas flow of 60 ml/min adjusted by a mass flow controller. The apparatus was flushed for approximately 20 min after the insertion of the sample to remove air contamination.

The tube was resistance-heated to the desired temperatures. Temperatures were measured and controlled using thermocouples and a thyristor controller. Two charcoal filters were placed at the end of the tube to prevent volatile radioactive species reaching the exhaust.

γ-ray spectroscopic measurements were performed using an HPGe-detector.

Short-term experiments: A γ-ray spectrum of the sample was recorded before each heating experiment. The sample was then placed into the evaporation apparatus, which was flushed with the appropriate gas mixture. After approximately 20 min, the apparatus was heated to the desired temperature within 10 min and kept at this temperature for 50 min. Subsequently, the sample was cooled to room temperature within 10 min using a fan. A γ-ray spectrum was recorded after the experiment (typical measuring time: 1 hour). The fractional release of the chalcogens was calculated comparing the integrated peak areas of the following characteristic γ-rays of the respective nuclides ($^{75}Se$: 264.66, 279.54, and 400.66 keV; $^{121}Te$: 507.59 and 573.14 keV; $^{206}Po$: 286.41, 311.56, 338.44, 522.47, 980.23 and 1032.26 keV [http://nucleardata.nuclear.lu.se/nucleardata/toi/]) before and after heating. The error bars given in the figures correspond to the standard errors of the mean values obtained by averaging the fractional release calculated for each characteristic γ-ray of the respective nuclide. Given the half-lives of the present nuclides ($^{75}Se$: 119.8 d; $^{121}Te$: 16.8 d; $^{206}Po$: 8.8 d [http://nucleardata.nuclear.lu.se/nucleardata/toi/]) a decay correction was omitted for these short-term experiments. However, $^{206}Bi$ ($t_{1/2}$=6.24 d [http://nucleardata.nuclear.lu.se/nucleardata/toi/]), which is formed by decay of $^{206}Po$, has been used as an internal standard to correct for geometry and self-absorption changes that may occur between the measurements before and after heating due to the melting process. For this purpose, the peak area ratios before and after heating for characteristic γ-rays of the internal standard lying energetically close to characteristic γ-rays of the investigated volatile nuclides were determined and the signals of the volatiles were corrected accordingly. No measurable evaporation of Bi was detected at temperatures below 1280 K. For the three samples heated at temperatures higher than 1280 K a small loss of Bi was observed giving rise to a small underestimation (about 1%) of the respective release values for the chalcogens.

Long-term experiments: In principle, the same experimental set-up was used as in the short-term experiments. However, the samples were kept in the apparatus for periods from 10 days up to several weeks with intermittent cooling-measuring-heating-up-cycles as described above. For the evaluation of these measurements a decay correction was applied to the integrated peak areas of the γ-ray signals of both volatile species and internal standard. $^{206}Bi$ could not be used as an internal standard because it is permanently produced by decay of $^{206}Po$. Therefore, $^{205}Bi$-containing LBE was used to dilute the samples and this isotope was used as standard.

Example 2

2. Experimental Setup

This experimental setup is e.g. suitable for the second preferred aspect of the present invention.

The experiment was performed at the ISOLDE facility (E. Kugler, *Hyperfine Interactions* 129, 23 (2000).). The spallation target consisted of a cylindrical tantalum container filled with liquid LBE. Protons pulses of 1.4 GeV and variable intensity (up to $10^{13}$ protons/pulse with a rate of one pulse every 16.8 s) impinged on the target. Following spallation reactions, the produced volatile elements exiting the liquid metal were ionized by means of a plasma ion source, then accelerated to 60 keV and sent to the magnetic mass separators and to the beam lines where the measuring stations were placed. An additional measurement was performed with a liquid Pb target.

Yields were measured using three different techniques of common use at ISOLDE. Online yields of stable isotopes and of some radioactive ones were measured by a Faraday cup inserted in the beam line. A special data acquisition system was developed to trigger the current measurement by a picoamperemeter with the arrival of the proton beam on target, thus allowing the measurement of the gas release curves, characteristic of each element. For short-lived β emitting isotopes, beams were directed to a dedicated tape station and yields were measured with a plastic scintillator detector.

A third measurement method was used for longer lived ($T_{1/2}$≥5 min) γ emitting radioisotopes; ion beams were implanted on thin Al foils, then after irradiation an offline γ detection was performed using a calibrated HPGe detector.

In order to obtain the absolute production rates from the measured yields, the efficiency of the ion source had to be measured. For this purpose, known amounts of different gas mixtures (consisting of Ar/Xe, He/Ne/Ar/Kr/Xe, and $^{3}$He/Ar/Xe mixtures) were leaked into the ion source, thus having the possibility to measure the efficiencies at any time during the experiment.

For the LBE target, the measurements were performed with the target at temperatures of 400° C. and 600° C. The Pb target was at a temperature of 520° C. These temperatures are in the range of the LBE temperature in MEGAPIE during operation, which varies from 300° C. to 400° C. depending on the position inside the target. Temperature differences within these ranges are not expected to affect the releases of the noble gases and of the Hg isotopes. On the other hand, differences are expected for some isotopes such as I, Cd and Po. Having performed the experiments at higher temperatures than in MEGAPIE will allow to conclude, in case the release of a specific isotope is not observed at 600° C., that no release should be observed in MEGAPIE for the same isotope at 300-400° C., even for longer irradiation times.

A selection of the data is presented in this invention (see the second preferred aspect above), with emphasis on the γ-spectroscopy data.

Example 3

The following Material and Methods are suitable for the third preferred aspect of the present invention.

1. Material and Methods

Cell Line:

Daudi cells (ATCC Nr. CCL-213) were used to simulate a leukemia model in mice. The cells were cultured in RPMI 1640 medium supplemented with 10% heat-inactivated fetal calf serum and 0.5% penicillin (10000 U/ml)/streptomycin (10 mg/ml) (Sigma-Aldrich). The cell suspension to be injected into mice was prepared by centrifuging the culture for 3 min at 1200 rpm, washing with PBS and re-suspending in PBS at 2.5-$10^{7}$ cells per ml.

Antibody Conjugate:

Rituximab antibody (Rituxan; IDEC Pharmaceuticals, San Diego, and Genentech Inc, San Francisco) is a chimeric version of anti CD-20 monoclonal antibody consisting of human IgG, constant region and murine variable region. The Rituximab antibody conjugated with SCN-CHX-A-DTPA (2-(4-isothiocyanatobenzyl)-cyclohexyl-dietylenetriamine pentaacetic acid), used in this study, was kindly provided by Dr. D. A. Scheinberg, Memorial Sloan Kettering Cancer Center, New York.

Radionuclide:

The $^{149}$Tb was produced using the on-line isotope separator facility ISOLDE at CERN (Geneva, Switzerland) [Kugler E. The ISOLDE Facility. *Hyperfine Interactions* 2000; 129: 23-42, Beyer G-J, Čomor J J, Daković M, Soloviev D, Tamburella C, Hagebø E, Allan B, Dmitriev S N, Zaitseva N G, Starodub G Y, Molokanova L G, Vranješ S D, Miederer M and the ISOLDE Collaboration. Production routes of the alpha emitting 149-Th for medical application. *Radiochim Acta* 2002; 90:247-252]. A tantalum-foil target (120 g/cm$^{2}$) was irradiated with 1.0 or 1.4 GeV protons delivered from the CERN PS-Booster accelerator. The radio-lanthanides generated in the spallation process are released from the target material, which is kept at about 2200° C., ionized by surface ionization and accelerated to 60 keV. From the obtained radioactive ion beams, the A=149 isobars ($^{149}$Dy, $^{149}$Tb and molecular ions $^{133}$CeO$^{+}$ and $^{133}$LaO$^{+}$) were implanted (60 keV) and thus collected in thin layers of $KNO_3$ (10 mg/cm$^{2}$) on aluminum backings. The $^{149}$Tb was separated from its daughters ($^{149}$Gd and $^{145}$Eu) and the pseudo-isobars $^{133}$Ce and $^{133}$La by cation exchange chromatography using Aminex A5 resin and α-hydroxyisobutyric acid as eluent. A typical elution chromatogram is presented in FIG. 13. The $^{149}$Tb-fraction (150-200 μl) was evaporated to dryness and re-dissolved in 50 μl of 100 mM HCl. The final $^{149}$Tb concentration was 2 GBq/ml (54 mCi/ml) at end of chromatographic separation (EOS).

Labeling Procedure:

25-40 μl of the $^{149}$Tb solution characterized above was used immediately for the labeling procedure. The pH was adjusted to 5.5 by adding 60 μl of 3 M $CH_3COONH_4$ solution, followed by the addition of 10 μl (40 mg/ml) ascorbic acid. After adding 5 μl of a stock solution of the chelated antibody in PBS (10 mg/ml) the mixture was incubated for 10 min at room temperature, before dilution to a final volume of 1.0 ml in PBS-1% human serum. The radiochemical purity of the labeled Rituximab was determined by ITLC (1.5×15 cm ITLC-SG strips, Gelman Instrument Company) using 0.1 M acetate buffer of pH 6 as a mobile phase and the linear analyzer (Berthold). The injection of the radioimmuno-conjugate into the mice was performed 1 h after EOS. The in vitro behavior of the labeled bioconjugate (immunoreactivity, cell binding, cell killing efficiency) has been described in a previous paper [Vranješ S D, Miederer M, Čomor J J, Soloviev D, Beyer G-J and the ISOLDE collaboartion. Labeling of monoclonal antibodies with 149-Th for targeted alpha therapy. *J Lab Comp Radiopharm* 2001; 44:718-720]. With the same antibody the inventors observed up to 55% cell binding without extrapolation to infinite antigen excess.

Mice Survival Studies:

The in vivo studies were performed using 26 female SCID mice (C.B.-17/ICR, Iffa Credo) under the authorization Nr: GE 31.1.1049/1879/11. The mice, which were 8 weeks old at the start of the experiment and weighed 20 g on average, were kept in sterile, ventilated boxes. Before injecting cells and antibodies, mice were anesthetized by i.p. (intra peritoneal) injection of 10 ml per kg (typically 0.2 ml) of an anesthetic (2.4 ml Ketasol 50, 0.8 ml Rompun, 6.8 ml 0.9% NaCi). Each mouse received 5-$10^{6}$ Daudi cells by injection of 0.2 ml cell suspension in PBS into the tail vein. Two days after xenotransplantation the mice were divided into four groups: the first group received 5 μg Rituximab in 0.1 ml PBS i.v.; the second group 300 μg Rituximab in 0.1 ml PBS i.v.; the third group 5.5 MBq $^{149}$Tb-CHX-A-DTPA-Rituximab radioimmunoconjugate (5 μg labeled Rituximab in 0.2 ml, i.v.), while the fourth group was left without any treatment. A summary of the in vivo study is presented in Table 2. According to the authorized protocol the mice were surveyed for 120 days: their behavior was logged each day, their condition was supervised once a week by a veterinarian, and they were weighed three times a week. At the appearance of obvious signs of paralysis, visible tumor masses, or a weight loss of >15%, the mice were sacrificed. One mouse was sacrificed shortly after injection (2 h p.i.) and kept deep-frozen for later analysis, in order to act as a reference for later quantification of the daughter radioactivity distribution.

Retention and Daughter Radioactivity Distribution:

Organ samples were taken from the sacrificed mice and the radioactivity concentration of the long-lived daughter products was determined by using high-resolution gamma spectroscopy (18% HP—Ge detector in combination with the Gamma spectrometer Genie 2000, Canberra). Whole, intact mice, as well as isolated organ samples were measured. Since the radioactivity content of the samples was essentially very low, long measuring times (between 1 and 24 hours) were applied.

Statistical Analysis:

The survival of animals until sacrifice because of disease development or the end of the experiment (no disease development) was compared between the different groups according a Kaplan Meier analysis using the Lee-Desu evaluation of the Unistat 3.0 statistical package (Megalon, Novato Calif., USA).

2. Results

Preparation of Labeled Rituximab:

Mass-separated and radiochemically pure $^{149}$Tb was obtained after chromatographic separation of the collected isobars with mass number A=149 at the on-line mass separator facility at CERN (FIG. 13). The overall time needed for the radiochemical separation and the labeling procedure was 1 hour. Radiolabeling of the Rituximab with this $^{149}$Tb-preparation was almost quantitative (>99%) within 10 minutes incubation time. The obtained preparation was thus ready for injection without further purification. The radioactivity concentration of the labeled antibody solution was 27.8 MBq/ml (0.75 mCi/ml), while the specific activity was 1.11 GBq/mg (30 mCi/mg) at the moment of injection.

Survival in a SCID Mouse Model of Leukemia:

The inventors set out to evaluate the efficacy of $^{149}$Tb-based TAT using a SCID mouse model of leukemia [16]. The inventor's experimental model involved the i.v. xenografting of lethal number of Daudi cells followed by TAT intervention at a time point when most of the Daudi cells would be expected to remain in circulation, and before the appearance of manifested tumors, which the inventors did not intend to target in this study. Survival data over a period of 4 months for treated mice and controls are shown in FIG. 14. All mice in the untreated control group developed clear signs of Burkitt lymphoma and were consequently sacrificed within 37 days. 50% of them developed visible macroscopic tumors while the others were sacrificed when they showed clear signs of paralysis or a weight loss >15% of the initial body weight (Table 2).

The injection of a single, low dose of Rituximab (5 μg/animal) did not show any therapeutic effect, and all mice in this group had to be sacrificed within 43 days. As can be seen from FIG. 14, the survival curves of this group and the control group (untreated mice) are almost identical. 83% of mice in this group expressed obvious signs of paralysis or weight loss of >3 g, while 17% of the mice developed visible macroscopic tumor masses.

A different survival pattern was observed after treatment with high dose of Rituximab (300 μg per animal, corresponding to 15 mg/kg). Although a single dose of 15 mg/kg Rituximab significantly increased the life expectancy—50% of mice in this group survived 100 days—ultimately, tumors developed in all animals (an example is shown in FIG. 15*a*) before the end of the observation period.

In contrast, the mice treated with the radioactive $^{149}$Tb-CHX-DTPA-Rituximab (5 μg Rituximab per animal) were almost completely protected over the entire observation period, with only one mouse in this group being lost after 48 days due to abdominal tumor growth.

Figure 15:

The remaining 8 mice (89%) showed normal behavior without any signs of disease for 4 months after grafting (FIG. 15*b*). All of these mice were sacrificed after 120 days and were found tumor free at dissection. Thus, a single injection of 5.5 MBq $^{149}$Tb-labeled Rituximab (5 μg MoAb), which corresponds to an injected dose of 280 MBq/kg body weight (7.5 mCi/kg), produced long-term survival without evidence of any disease at 120 days. The survival increase after the RIT compared to all control groups (no treatment, 5 μg and 300 μg unlabeled Rituximab) was highly significant in the statistical Lee-Desu comparisons (p<0.005).

Biodistribution of Labeled Rituximab and the Daughter Radionuclides:

In FIG. 16 the inventors present typical γ-spectra of retained activity in organs recorded 120 days after injecting the short-lived radioimmunoconjugate. The biodistribution of $^{149}$Th-CHX-A-DTPA-Rituximab radioimmunoconjugate shortly after injection was assessed using a single mouse sacrificed at 2 h. The retention of the long-lived daughter nuclides at 120 days after injection is presented in Table 3. After 2 h, the organs with high blood pool like spleen, heart and kidney (42, 41 and 24% ID/g), showed relatively high radioactivity concentration. High amounts of the radioimmunoconjugate was found in the liver at this time point (18±3% injected dose) confirming the results of earlier systematic studies [Beyer G-J, Offord R E, Künzi G, Jones R M L, Ravn U, Aleksandrova Y, Werlen R C, Mäcke H, Lindroos M, Jahn S, Tengblad O and the ISOLDE Collaboration. Biokinetics of monoclonal antibodies labeled with radio-lanthanides and 225-Ac in xenografted nude mice. *J Label Compd Radiopharm* 1995; 37:229-530]. The values in the other organs were relatively low. After 120 days, 71.6% of the primary injected radioactive atoms had been excreted from the mice. The retention of the daughter products was 28.4±4%, out of which 91.1% remained in the bone tissue and 6.3% in the liver.

Tables

TABLE 1

Calculated values for mean partial molar enthalpies of solution of the chalcogens Q (Q = Se, Te, Po) in liquid lead and bismuth ($\Delta\bar{H}^{solv}_{Q\ in\ Pb/Bi}(1)$) and mean partial molar enthalpies of evaporation from liquid lead and bismuth of the chalcogens Q in the monoatomic ($\Delta\bar{H}^{v}_{Q}$) and diatomic state ($\Delta\bar{H}^{v}_{Q2}$) and as diatomic metal chalcogenides molecules ($\Delta\bar{H}^{v}_{PbQ}$ and $\Delta\bar{H}^{v}_{BiQ}$).

| Chalcogen Q | $\Delta\bar{H}^{solv}_{Q\ in\ Pb/Bi}(1)$ [kJmol$^{-1}$] | $\Delta\bar{H}^{v}_{Q}$ [kJmol$^{-1}$] | $\Delta\bar{H}^{v}_{Q2}$ [kJmol$^{-1}$] | $\Delta\bar{H}^{v}_{PbQ}$ [kJmol$^{-1}$] | $\Delta\bar{H}^{v}_{BiQ}$ [kJmol$^{-1}$] |
|---|---|---|---|---|---|
| Se | −38.7 | 268.2 | 203.8 | 219.4 | 177.9 |
| Te | −11.2 | 205.4 | 147.8 | 218.0 | 164.5 |
| Po | −8.8 | 185.4 | 159.3 | 231.3 | 176.3 |

TABLE 2

Summary of the in vivo experiments on SCID mice xenotransplanted with Daudi cells and treated by immunotherapy or radioimmunotherapy with $^{149}$Tb-labeled Rituximab.

| | SCID mice groups | | | |
|---|---|---|---|---|
| | Group 1 | Group 2 | Group 3 | Group 4 (control group) |
| No. of mice per group | 6 | 4 | 9 | 6 |
| First i.v. injection | 5 · $10^6$ Daudi cells | | | |
| Second i.v. injection 2 days after Daudi cell inoculation | 5 µg Rituximab | 300 µg Rituximab | 5 µg $^{149}$Tb-labeled Rituximab (5.55 MBq) | NONE |
| Follow-up (120 days after the therapy) | 17% developed macroscopic tumors, 83% paralyzed, weight loss | 50% developed macroscopic tumors, 50% paralyzed, weight loss | 89% no pathologic changes, 11% paralyzed, abdominal tumor | 50% developed macroscopic tumors, 50% paralyzed, weight loss |

TABLE 3

Biodistribution of $^{149}$Tb-labeled Rituximab in SCID mice 2 h after i.v. injection (column 2 and 3) and of the remaining daughter radioactivity distribution 120 days after injection (column 3 and 4). Note, that both femurs and both kidneys were combined for the gamma spectroscopic measurements in order to increase the signal to background ratio.

| | 2 h p.i. | | 120 d p.i. | |
|---|---|---|---|---|
| Organ | [% i.d./Organ] | [%/g tissue] | [% i.d./Organ] | [%/g tissue] |
| Blood | n.a. | | <0.01 | |
| Liver | 18 ± 3 | 24 ± 4 | 1.8 ± 0.3 | 1.6 ± 0.2 |
| Bone*[1] | 13 ± 1 | 9.1 ± 0.7 | 26 ± 4 | 13 ± 2 |
| Spleen | 1.9 ± 0.2 | 42 ± 4 | 0.40 ± 0.06 | 12 ± 2 |
| Heart | 4.7 ± 0.7 | 41 ± 6 | <0.01 | |
| Lung | 2.4 ± 0.5 | 18 ± 4 | <0.01 | |
| Kidney*[2] | 6 ± 1 | 24 ± 4 | 0.2 ± 0.03 | 0.50 ± 0.08 |
| Muscles | | <0.2 | <0.02 | |
| Bladder*[3] | 0.12 ± 0.03 | 3.7 ± 0.9 | <0.01 | |
| Body total | 100 | | 28.4 ± 4 | |

*[1]Bone total was calculated as 9 × both femur activity

*[2]Both kidneys were measured together

*[3]Bladder measured with urine n.a. not done, not assessable

TABLE 4

Radioactivity level of long-lived daughter products retained in a patient after injection of 1 GBq $^{149}$Tb-Rituximab antibodies, assuming 100% retention of the long-lived daughter products (worst case). The retention has been measured to be only 28.4% independent on the decay mode (alpha or EC) (see Table 3), thus the real activity of daughter products would be nearly a factor 4 smaller. On the other hand, the injection of a $^{149}$Tb labeled bioconjugate 4 hours after the Tb purification would increase the activity of the daughter product be by a factor 2. In this way the numbers in this table can still be seen as upper limits.

| | $^{149}$Tb 4.12 h | $^{149}$Gd 9.28 d | $^{149}$Eu 93.1 d | $^{145}$Eu 5.93 d | $^{145}$Sm 340 d | $^{145}$Pm 17.7 y |
|---|---|---|---|---|---|---|
| $t_{inj}$ = 0 | 1.0 GBq | | | | | |
| 2 d | 310 kBq | 13 MBq | 0.2 MBq | 3.9 MBq | 18 kBq | |
| 5 d | | 11 MBq | 0.4 MBq | 2.7 MBq | 37 kBq | 43 Bq |
| 10 d | | 7.3 MBq | 0.7 MBq | 1.5 MBq | 57 kBq | 86 Bq |
| 100 d | | 8 kBq | 0.7 MBq | 41 Bq | 70 kBq | 0.8 kBq |
| 1 y | | | 0.1 MBq | | 41 kBq | 2.2 kBq |
| 10 y | | | 0 | | 50 Bq | 3.1 kBq |

The invention claimed is:

1. A method for the large scale production of a high-purity carrier-free or non-carrier added radioisotopes in a quantity suitable for medical applications comprising the following steps:

(a) activation of a target by a particle beam, (b) separation of the isotope from the irradiated target under vacuum or in an inert atmosphere, (c) ionisation of the separated isotope in an ion source, (d) extraction of the ionized isotope from the ion source in an ion beam and acceleration of the ion beam, (e) mass-separation of the isotope, and (f) collection of the isotope including implanting, the isotope in the mass-separated ion beam into an implantation substrate and separating the isotope from the implantation substrate containing the isotope, wherein separating the isotope from the implanation substrates includes dissolving the implantation substrate in a small volume of water or an eluting agent.

2. The method according to claim 1, wherein the mass separation process is controlled by mass marking.

3. The method according to claim 1, wherein before step (c) the isotope of interest is introduced into an oven from where a sample is fed into the ion source.

4. The method according to claim 1, wherein the ionisation in step (c) is surface ionisation, laser ionisation or plasma ionisation.

5. The method according to claim 1, wherein the mass separation of step (e) is an on-line or an off-line mass separation.

6. The method according to claim 1, wherein in step (f) the isotope of interest is collected by implantation into a prepared chemical substrate.

7. The method according to claim 1, wherein radioisotopes in carrier-free or non-carrier added form are produced.

8. The method according to claim 1, wherein an implantation energy is selected in order to adjust the implantation depth.

9. The method according to claim 1, wherein the implantation is performed through a thin cover layer into the implantation substrate.

10. The method according to claim 1, wherein the implantation substrate is a salt layer, a water-soluble substance, a thin ice layer of frozen water or another liquid, or a solid matrix.

11. A method for direct radioisotope-labelling of a bioconjugate, comprising (i) performing a method according to claim 1, (ii) obtaining the product fraction containing the radioisotope of interest in a small volume, and (iii) direct radioisotope-labelling of the bioconjugate and/or direct injection into a chromatographic system for further purification, wherein the bioconjugate is an immuno-conjugate, antibody, protein, peptide, nucleic acid, oligonucleotide, or fragment thereof.

12. The method according to claim 11, wherein the bioconjugate further comprises a nanoparticle, microsphere or macroaggregate that is conjugated with, or covalently or non-covalently attached to, said immuno-conjugate, antibody, protein, peptide, nucleic acid, oligonucleotide or a fragment thereof.

13. The method according to claim 1, wherein the implantation substrate is a nanoparticle, macromolecule, microsphere, macroaggregate, ion exchange resin, or other matrix used in a chromatographic system.

* * * * *